(12) United States Patent
Gao et al.

(10) Patent No.: US 12,384,796 B2
(45) Date of Patent: Aug. 12, 2025

(54) ELECTROACTIVE COMPOUNDS

(71) Applicant: LG Chem, Ltd., Seoul (KR)

(72) Inventors: Weiying Gao, Landenberg, PA (US); Giang Dong Vo, Wilmington, DE (US); Michael Henry Howard, Montchanin, DE (US); Weishi Wu, Landenberg, PA (US); Norman Herron, Newark, DE (US)

(73) Assignee: LG Chem, Ltd., Seoul (KR)

( * ) Notice: Subject to any disclaimer, the term of this patent is extended or adjusted under 35 U.S.C. 154(b) by 427 days.

(21) Appl. No.: 16/301,483

(22) PCT Filed: May 25, 2017

(86) PCT No.: PCT/US2017/034419
§ 371 (c)(1),
(2) Date: Nov. 14, 2018

(87) PCT Pub. No.: WO2017/210072
PCT Pub. Date: Dec. 7, 2017

(65) Prior Publication Data
US 2020/0013959 A1 Jan. 9, 2020

Related U.S. Application Data

(60) Provisional application No. 62/345,259, filed on Jun. 3, 2016.

(51) Int. Cl.
*C07D 307/92* (2006.01)
*C07D 493/04* (2006.01)
(Continued)

(52) U.S. Cl.
CPC ......... *C07D 493/14* (2013.01); *C07D 307/92* (2013.01); *C07D 493/04* (2013.01);
(Continued)

(58) Field of Classification Search
CPC .. C07D 493/04; C07D 495/04; C07D 517/04; C07D 307/92; H01L 51/0071;
(Continued)

(56) References Cited

U.S. PATENT DOCUMENTS 5,792,557 A * 8/1998 Nakaya ................. C07C 211/54
313/504
5,936,259 A 8/1999 Katz et al.
(Continued)

FOREIGN PATENT DOCUMENTS

CN 101407493 A 4/2009
CN 103421164 A 12/2013
(Continued)

OTHER PUBLICATIONS

Machine translation of CN 103664995 A obtained from WIPO (Year: 2014).*
(Continued)

*Primary Examiner* — Elizabeth M. Dahlburg
*Assistant Examiner* — Braelyn R Watson
(74) *Attorney, Agent, or Firm* — Lerner David LLP

(57) ABSTRACT

There is provided a compound having Formula I:

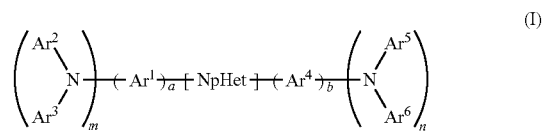

In the formula: NpHet is a naphthalene core having at least one fused 5-membered heteroaromatic ring, where the heteroaromatic ring has one heteroatom which is O, S, Se, or Te; $Ar^1$-$Ar^6$ are the same or different and are a hydrocarbon
(Continued)

aryl group, a heteroaryl group, or a deuterated analog thereof; a and b are the same or different and are 0 or 1; m and n are the same or different and are 0 or 1; with the proviso that a, b, m, and n are not all 0.

1 Claim, 2 Drawing Sheets

(51) Int. Cl.
*C07D 493/14* (2006.01)
*C09K 11/06* (2006.01)
*H10K 50/11* (2023.01)
*H10K 85/60* (2023.01)

(52) U.S. Cl.
CPC .............. *C09K 11/06* (2013.01); *H10K 50/11* (2023.02); *H10K 85/626* (2023.02); *H10K 85/633* (2023.02); *H10K 85/636* (2023.02); *H10K 85/657* (2023.02); *H10K 85/6574* (2023.02); *C09K 2211/1018* (2013.01)

(58) Field of Classification Search
CPC ............. H01L 51/0073; H01L 51/0074; H01L 51/0059; H01L 51/006; H01L 51/0061; H01L 51/0058; H01L 51/5012; C09K 2211/1018; C09K 11/06
See application file for complete search history.

(56) References Cited

U.S. PATENT DOCUMENTS

| | | | |
|---|---|---|---|
| 8,067,764 B2 | 11/2011 | Meng | |
| 8,212,239 B2 | 7/2012 | Meng | |
| 8,216,753 B2 | 7/2012 | Meng | |
| 8,247,810 B2 | 8/2012 | Meng | |
| 8,324,619 B2 | 12/2012 | Meng | |
| 8,471,251 B2 | 6/2013 | Meng | |
| 8,563,972 B2 | 10/2013 | Meng | |
| 8,816,100 B2 | 8/2014 | Takimiya | |
| 9,112,157 B2 | 8/2015 | Brown et al. | |
| 2003/0076032 A1* | 4/2003 | Suzuri .................. | H01L 51/006 313/504 |
| 2004/0102577 A1 | 5/2004 | Hsu et al. | |
| 2004/0127637 A1 | 7/2004 | Hsu et al. | |
| 2005/0205860 A1 | 9/2005 | Hsu et al. | |
| 2005/0234159 A1 | 10/2005 | Takeuchi et al. | |
| 2006/0103298 A1* | 5/2006 | Lee ..................... | H01L 51/5016 313/504 |
| 2009/0066225 A1 | 3/2009 | Kimura et al. | |
| 2009/0159877 A1 | 6/2009 | Meng | |
| 2010/0032658 A1* | 2/2010 | Lee ..................... | H01L 51/0073 257/40 |
| 2011/0040069 A1 | 2/2011 | Miura et al. | |
| 2011/0042652 A1 | 2/2011 | Meng | |
| 2011/0095270 A1 | 4/2011 | Meng | |
| 2011/0168992 A1 | 7/2011 | Bae et al. | |
| 2011/0260114 A1 | 10/2011 | Wu et al. | |
| 2011/0272681 A1 | 11/2011 | Sugimoto et al. | |
| 2013/0187140 A1 | 7/2013 | Rostovtsev et al. | |
| 2013/0310556 A1 | 11/2013 | Melzig et al. | |
| 2014/0027741 A1 | 1/2014 | Park et al. | |
| 2014/0034915 A1 | 2/2014 | Lee et al. | |
| 2014/0051865 A1 | 2/2014 | Takimiya | |
| 2014/0239281 A1 | 8/2014 | Ise et al. | |
| 2014/0252324 A1 | 9/2014 | Lee | |
| 2014/0339519 A1 | 11/2014 | Takada et al. | |
| 2015/0001494 A1 | 1/2015 | Kim et al. | |
| 2015/0011780 A1 | 1/2015 | Takimiya et al. | |
| 2015/0028265 A1 | 1/2015 | Yang et al. | |
| 2015/0045560 A1* | 2/2015 | He ........................ | C07F 7/083 548/421 |
| 2015/0133679 A1 | 5/2015 | Park et al. | |
| 2015/0214492 A1 | 7/2015 | Yen et al. | |
| 2016/0369045 A1 | 12/2016 | He et al. | |
| 2019/0378992 A1 | 12/2019 | Skulason et al. | |

FOREIGN PATENT DOCUMENTS

| | | | |
|---|---|---|---|
| CN | 103664995 A | * | 3/2014 |
| CN | 104693161 A | | 6/2015 |
| JP | H11195790 A | | 7/1999 |
| JP | 2001196182 A | | 7/2001 |
| JP | 2005206750 A | | 8/2005 |
| JP | 2007067262 A | | 3/2007 |
| JP | 2009194208 A | | 8/2009 |
| JP | 2009267134 A | | 11/2009 |
| JP | 2012503027 A | | 2/2012 |
| JP | 2013159584 A | | 8/2013 |
| JP | 2013232521 A | * | 11/2013 |
| JP | 2015519300 A | | 7/2015 |
| KR | 20110083442 A | | 7/2011 |
| KR | 20120065214 A | | 6/2012 |
| KR | 20130006029 A | | 1/2013 |
| KR | 20130139412 A | | 12/2013 |
| KR | 20140064463 A | | 5/2014 |
| KR | 20150030794 A | | 3/2015 |
| KR | 20150069119 A | | 6/2015 |
| KR | 20160005944 A | | 1/2016 |
| KR | 20160041391 A | | 4/2016 |
| KR | 20170063472 A | | 6/2017 |
| KR | 20190141274 A | | 12/2019 |
| WO | 2004005389 A1 | | 1/2004 |
| WO | 2006100896 A1 | | 9/2006 |
| WO | 2006113205 A2 | | 10/2006 |
| WO | 2009018009 A1 | | 2/2009 |
| WO | 2009102031 A1 | | 8/2009 |
| WO | 2010058692 A1 | | 5/2010 |
| WO | 2010075421 A2 | | 7/2010 |
| WO | 2010084852 A1 | | 7/2010 |
| WO | 2011053334 A1 | | 5/2011 |
| WO | 2011156478 A2 | | 12/2011 |
| WO | 2012105517 A1 | | 8/2012 |
| WO | 2012118174 A1 | | 9/2012 |
| WO | 2012165612 A1 | | 12/2012 |
| WO | 2013009032 A2 | | 1/2013 |
| WO | 2013024731 A1 | | 2/2013 |
| WO | 2013027693 A1 | | 2/2013 |
| WO | 2013031468 A1 | | 3/2013 |
| WO | 2013098648 A1 | | 7/2013 |
| WO | 2013121664 A1 | | 8/2013 |
| WO | 2012084231 A9 | | 10/2013 |
| WO | 2013149001 A2 | | 10/2013 |
| WO | 2013173396 A2 | | 11/2013 |
| WO | 2014128281 A1 | | 8/2014 |
| WO | 2015096886 A1 | | 7/2015 |
| WO | 2015099486 A1 | | 7/2015 |
| WO | 2015137304 A1 | | 9/2015 |
| WO | 2018097937 A1 | | 5/2018 |

OTHER PUBLICATIONS

Zhang, Dongdong, et al. "Sterically shielded blue thermally activated delayed fluorescence emitters with improved efficiency and stability." Materials Horizons 3.2 (2016): 145-151. (Year: 2016).*
Mitsui, Chikahiko, et al. "Single-crystal organic field-effect transistors of naphthodifurans." Bulletin of the Chemical Society of Japan 88.6 (2015): 776-783. (Year: 2015).*
What is the Visible Light Spectrum? Understanding the Colors That Make Up White Light, ThoughtCo. (Year: 2022).*
Chang SL, Lu CW, Lai YY, Hsu JY, Cheng YJ. Synthesis and molecular properties of two isomeric dialkylated tetrathienonaphthalenes. Organic letters. Feb. 5, 2016;18(3):368-71.
Citation List from Notice of Reasons for Refusal for Japanese Patent Application No. 2018563495 issued Jun. 15, 2020; 1 page.
Chinese Search Report for Application No. CN201780032457.2 dated Jan. 14, 2021, 3 pgs.
Song et al., "Synthesis and molecular properties of butterfly-shaped tetrathiophene derivatives", Science Direct, Tetrahedron, vol. 71, Available online Feb. 7, 2015, pp. 1838-1843.

(56) References Cited

OTHER PUBLICATIONS

Acharya, R.V., et al., "Quinone series Chapter XI: Reaction of 2,3-dichloro-1,4-naphthoquinone with dihydroxynaphthalenes", Journal of Scientific & Industrial Research (1957) vol. 16B, pp. 554-557.
Bilger, C., et al., "Sur quelques modifications d'activite biologique consecutives a l'accolement d'un second cycle nitrofuranne a l'homocycle de nitroarenofurannes", European Journal of Medicinal Chemistry, May 1987, vol. 22, pp. 213-219 (English Translation of Abstract Only).
CRC Handbook of Chemistry and Physics, 81st Edition (2000-2001) Please see the attached placeholder and note that the USPTO generally has access to CRC-published texts: https://www.uspto.gov/learning-and-resources/support-centers/scientific-and-technical-information-center-stic/electronic <https://protect-us.mimecast.com/s/PaLrCPN5YlTKJpQqf0avw8?domain=uspto.gov>.
Frederiksen, P., et al., "Two-Photon Photosensitized Production of Singlet Oxygen in Water", Journal of American Chemical Society, (Dec. 10, 2004), vol. 127, No. 1, pp. 255-269.
Gidron, O., et al., "a-Oligofurans: An Emerging Class of Conjugated Oligomers for Organic Electronics", Angewandte Chemical Internatioanl Edition, Jan. 2014, vol. 53, No. 10, pp. 2546-2555.
Gustafsson, G., et al., "Flexible light-emitting diodes made from soluble conducting polymers", Nature, vol. 357, Jun. 11, 1992, pp. 477-479.
Huang, JD., et al., "Impact of Edge-Core Structures and Substituent Effects on the Electronic and Charge-Transport Properties of Heteroaromatic Ring-Fused Oligomers", Journal of Physical Chemistry C, (Dec. 5, 2014), vol. 119, No. 1, pp. 33-44.
International Search Report including the Written Opinion from Application No. PCT/US2017/034419 mailed Sep. 6, 2017, pp. 1-11.
Kuriakose, A.P., et al., "Furan derivatives. Chapter VI: Synthesis of 1,7-dimethylnaphtho(2, 1-b:7,6-b')difuran", Journal of the Indian Chemical Society (1972) vol. 49, pp. 1197-1198.

Li, W., et al., "More than just a GPCR ligand: structure-based discovery of thioridazine derivatives as Pim-1 kinase Inhibitors", MedChemComm (Feb. 5, 2014), vol. 5, No. 4, pp. 507-511.
Mitsui, C., et al., "Single-Crystal Organic Field-Effect Transistors of Naphthodifurans", Bulletin of the Chemical Society of Japan, Jun. 2015, vol. 88, No. 6, pp. 776-783.
Nakano, M, et al., "Isomerically Pure Anthra[2,3?b:6,7?b']-difuran (anti-ADF), -dithiophene (anti-ADT), and—diselenophene (anti ADS): Selective Synthesis, Electronic Structures, and Application to Organic Field-Effect Transistors", Journal of Organic Chemistry, Aug. 2012, vol. 77, No. 18, pp. 8099-8111.
Nakano, M., et al., "Angular-shaped naphthodifurans, naphtho[1,2-b;5,6-b]-and naphtho[2,1-b;6,5-b]-difuran: are they soelectronic with chrysene?", Chemical Communications (Cambridge, United Kingdom), Apr. 2012, vol. 48, pp. 5671-5673.
Nakano, M., et al., "Naphtho[2,3-b:6,7-b'] dichalcogenophenes: Syntheses, Characterizations, and Chalcogene Atom Effects on Organic Field-Effect Transistor and Organic Photovoltaic Devices", Chemistry of Materials, (Nov. 26, 2011), vol. 24, pp. 190-198.
Qian, XH. et. al., "Synthesis, DNA intercalation activities and molecular modeling on structures of tetramethylnaphthodifurans", Gaodeng Xuexiao Huaxue Xuebao (1996) vol. 17, No. 9, pp. 1399-1403.
Ronto, G., et al., "Genotoxic effectivity. Comparison of 36 nitrated furan and arenofuran derivatives on a quantitative scale. Statistical comparison of T7 and other short-term tests", Mutagenesis (Jul. 1, 1992), vol. 7, No. 4, pp. 243-249.
Song, J. et al., "Synthesis and molecular properties of butterfly-shaped tetrathiophene derivatives", Tetrahedron, Feb. 2015, vol. 71, No. 12, pp. 1838-1843. See scheme 1, compound 4.
Martin, C.J., et al., "Oxidative Bond Formation in Dithienyl Polyphenylenes: Optical and Electrochemical Consequences". Eur. J. Org. Chem., 3491-3499 (May 2011). 9 pgs.

* cited by examiner

ELECTROACTIVE COMPOUNDS

CLAIM OF BENEFIT OF PRIOR APPLICATION

This application claims the benefit of U.S. Provisional Application No. 62/345,259, filed Jun. 3, 2016, which is incorporated in its entirety herein by reference.

BACKGROUND INFORMATION

Field of the Disclosure

This disclosure relates in general to blue luminescent compounds and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new luminescent compounds.

SUMMARY

There is provided a compound having Formula I, as described below in the detailed description.

There is also provided an organic electronic device comprising a first electrical contact, a second electrical contact and a photoactive layer therebetween, the photoactive layer comprising a compound having Formula I.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
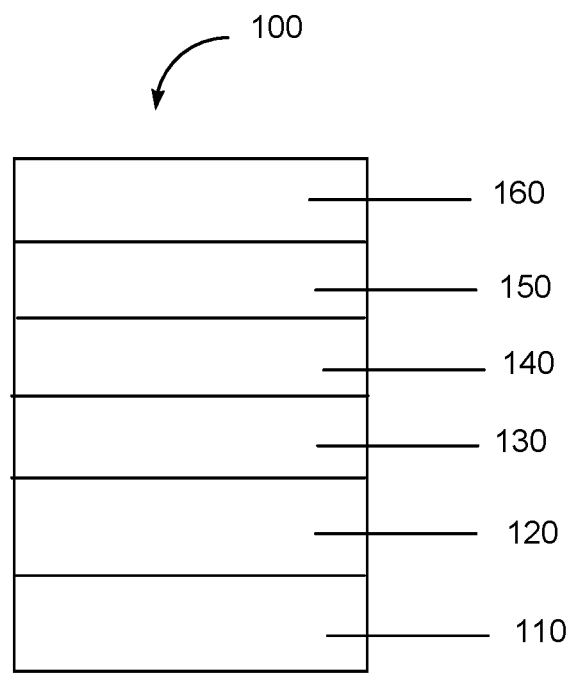
FIG. 1 includes an illustration of one example of an organic electronic device including a new compound described herein.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Compound Having Formula I, Devices, and finally Examples.

1. Definitions and Clarification of Terms

Before addressing details of embodiments described below, some terms are defined or clarified.

As used in the "Definitions and Clarification of Terms", R, R' and R" and any other variables are generic designations and may be the same as or different from those defined in the formulas.

The term "adjacent" as it refers to substituent groups refers to groups that are bonded to carbons that are joined together with a single or multiple bond. Exemplary adjacent R groups are shown below:

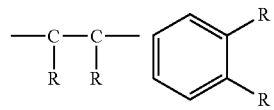

The term "alkoxy" is intended to mean the group RO—, where R is an alkyl group.

The term "alkyl" is intended to mean a group derived from an aliphatic hydrocarbon and includes a linear, a branched, or a cyclic group. In some embodiments, an alkyl has from 1-20 carbon atoms.

The term "aromatic compound" is intended to mean an organic compound comprising at least one unsaturated cyclic group having 4n+2 delocalized pi electrons.

The term "aryl" or "aryl group" is intended to mean a moiety derived from an aromatic compound. A group "derived from" a compound, indicates the radical formed by removal of one or more hydrogen ("H") or deuterium ("D"). The aryl group may be a single ring (monocyclic) or have multiple rings (bicyclic, or more) fused together or linked covalently. A "hydrocarbon aryl" has only carbon atoms in the aromatic ring(s). A "heteroaryl" has one or more heteroatoms in at least one aromatic ring. In some embodiments, hydrocarbon aryl groups have 6 to 60 ring carbon atoms; in some embodiments, 6 to 30 ring carbon atoms. In some embodiments, heteroaryl groups have from 2-50 ring carbon atoms; in some embodiments, 4-30 ring carbon atoms. The term "alkylaryl" or "alkylaryl group" is intended to mean an aryl group having at least one alkyl substituent.

The term "aryloxy" is intended to mean the group RO—, where R is an aryl group.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge.

Although light-emitting materials may also have some charge transport properties, the term "charge transport layer, material, member, or structure" is not intended to include a layer, material, member, or structure whose primary function is light emission.

The abbreviation "DBA" stands for dibenzylideneacetone.

The term "deuterated" is intended to mean that at least one hydrogen ("H") has been replaced by deuterium ("D"). The term "deuterated analog" is intended to mean a structural analog of a compound or group in which one or more available hydrogens have been replaced with deuterium. In a deuterated compound or deuterated analog, the deuterium is present in at least 100 times the natural abundance level. The term "% deuterated" or "% deuteration" is intended to mean the ratio of deuterons to the sum of protons plus deuterons, expressed as a percentage.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "germyl" is intended to mean the group $R_3Ge$—, where R is the same or different at each occurrence and is H, D, C1-20 alkyl, deuterated alkyl, fluoroalkyl, aryl, or deuterated aryl.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material", "emissive material" and "emitter" are intended to mean a material that emits light when activated by an applied voltage (such as in a light-emitting diode or light-emitting electrochemical cell). The term "blue luminescent material" is intended to mean a material capable of emitting radiation that has an emission maximum at a wavelength in a range of approximately 445-490 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "nitrilo" is intended to mean the group —C≡N.

The term "organic electronic device" or sometimes just "electronic device" is intended to mean a device including one or more organic semiconductor layers or materials.

The term "photoactive" is intended to mean a material or layer that emits light when activated by an applied voltage (such as in a light emitting diode or chemical cell) or responds to radiant energy and generates a signal with or without an applied bias voltage (such as in a photodetector or a photovoltaic cell).

The term "siloxane" is intended to mean the group $R_3SiOR_2Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" is intended to mean the group $R_3SiO$—, where R is the same or different at each occurrence and is H, D, C1-20 alkyl, deuterated alkyl, fluoroalkyl, aryl, or deuterated aryl.

The term "silyl" is intended to mean the group $R_3Si$—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

All groups may be unsubstituted or substituted. The substituent groups are discussed below. In a structure where a substituent bond passes through one or more rings as shown below,

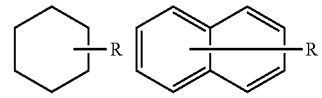

it is meant that the substituent R may be bonded at any available position on the one or more rings.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics,* 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Compounds Having Formula I

The compounds described herein have Formula I

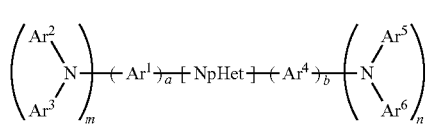
(I)

wherein:
NpHet is a naphthalene core having at least one fused 5-membered heteroaromatic ring, where the heteroaromatic ring has one heteroatom selected from the group consisting of O, S, Se, and Te;
$Ar^1$-$Ar^6$ are the same or different and are selected from the group consisting of hydrocarbon aryl groups, heteroaryl groups, and deuterated analogs thereof;
a and b are the same or different and are 0 or 1;
m and n are the same or different and are 0 or 1;
with the proviso that a, b, m, and n are not all 0.

In some embodiments, the compounds having Formula I have a single NpHet group.

In some embodiments, the compounds having Formula I have no N-heteroaryl groups.

In some embodiments, the compounds having Formula I have no heteroaryl groups other than NpHet.

In some embodiments, the compounds having Formula I are useful as emissive materials. In some embodiments, the compounds are blue emissive materials. They can be used alone or as a dopant in a host material.

In some embodiments, the compounds having Formula I have deep blue color. As used herein, the term "deep blue color" refers to a C.I.E. y-coordinate of less than 0.10, according to the C.I.E. chromaticity scale (Commission Internationale de L'Eclairage, 1931). In some embodiments, the compounds having Formula I have a photoluminescence y-coordinate of less than 0.10; in some embodiments, less than 0.090.

In some embodiments, electroluminescent devices including the compounds of Formula I as emissive materials have deep blue color. In some embodiments, the x-coordinate is less than 0.15 and the y-coordinate is less than 0.10; in some embodiments, the y-coordinate is less than 0.090.

In some embodiments, the compounds having Formula I have a photoluminescence emission profile with a width at half the maximum intensity ("FWHM") that is less than 60 nm; in some embodiments, less than 50 nm; in some embodiments, less than 40 nm. This is advantageous for display devices for producing more saturated color.

In some embodiments, the compounds having Formula I are useful as host materials in combination with one or more dopant materials.

In some embodiments, the NpHet core has one or more additional substituents on one or more of the fused rings. In some embodiments, the additional substituents are selected from the group consisting of D, nitrilo, alkyl, silyl, germyl, diarylamino, hydrocarbon aryl, diarylamino-substituted hydrocarbon aryl, heteroaryl, diarylamino-substituted heteroaryl, deuterated alkyl, deuterated silyl, deuterated germyl, deuterated diarylamino, deuterated hydrocarbon aryl, deuterated diarylamino-substituted hydrocarbon aryl, deuterated heteroaryl, deuterated diarylamino-substituted heteroaryl, and combinations thereof.

In some embodiments, the additional substituents on the NpHet core are selected from the group consisting of D, aryl, alkylaryl, deuterated aryl, deuterated alkylaryl, and combinations thereof.

In some embodiments, the additional substituents on the NpHet core are one or both of

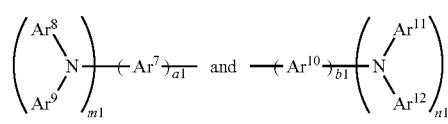

where
$Ar^7$—$Ar^{12}$ are the same or different and are selected from the group consisting of hydrocarbon aryl groups, heteroaryl groups, and deuterated analogs thereof;
a1, b1, m1, and n1 are integers such that a1+m1=1 or 2 and b1+n1=1 or 2.

The aryl- and/or amine-containing groups

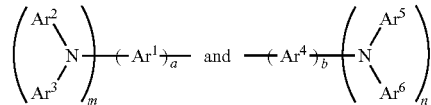

are bonded to different rings of the NpHet core. These groups can be bonded to any available position on a given ring.

When a third aryl- and/or amine-containing group is present, it is bonded to a third different ring on the NpHet core.

When a fourth aryl- and/or amine-containing group is present, it is bonded to a fourth different ring on the NpHet core.

In some embodiments of Formula I, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I, deuteration is present on the core NpHet group.

In some embodiments of Formula I, deuteration is present on one or more substituent groups on the NpHet core.

In some embodiments of Formula I, deuteration is present on one or both amine-containing groups.

In some embodiments of Formula I, deuteration is present on the two or more of the core NpHet group, substituents on the core NpHet group, and an amine-containing group.

In some embodiments of Formula I, the compound has no 5-membered rings fused in the orientation shown below, where the dashed line indicates fusion to the naphthalene core.

In some embodiments of Formula I, at least one 5-membered fused ring has a substituent in the 2-position shown below, where the dashed line indicates fusion to the naphthalene core.

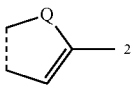

Substituent groups are discussed in detail below.

In some embodiments of Formula I, each 5-membered fused ring has a substituent in the 2-position.

In some embodiments of Formula I, at least one 5-membered fused ring has a diarylamino or diarylamino-substituted hydrocarbon aryl in the 2-position.

In some embodiments of Formula I, each 5-membered fused ring has a diarylamino or diarylamino-substituted hydrocarbon aryl in the 2-position.

In some embodiments of Formula I, NpHet has Formula NpHet-1

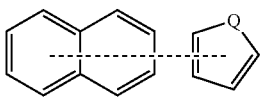

NpHet-1 where Q=O, S, Se, or Te and the dashed line indicates that the 5-membered ring is fused at any available position in any orientation.

In some embodiments of NpHet-1, Q=O.
In some embodiments of NpHet-1, Q=S.
In some embodiments of NpHet-1, Q=Se.
In some embodiments of NpHet-1, Q=Te.

In some embodiments of Formula I, NpHet has Formula NpHet-1 and is selected from one of the isomers below, substituted derivatives thereof, and deuterated analogs thereof.

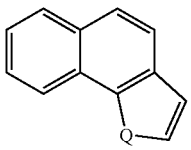

NpHet1-A

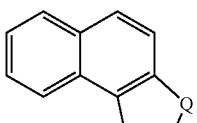

NpHet1-B

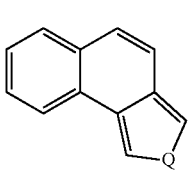

NpHet1-C

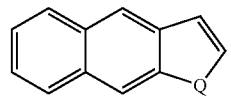

NpHet1-D

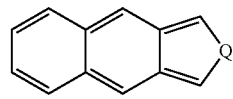

NpHet1-E

In some embodiments of Formula I, NpHet is selected from the group consisting of NpHet1-A, NpHet1-B, NpHet1-D, substituted derivatives thereof, and deuterated analogs thereof.

In some embodiments of Formula I, NpHet has Formula NpHet-2

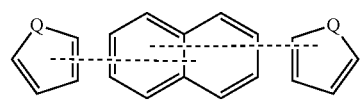

NpHet-2 where Q=O, S, Se, or Te and the dashed lines indicate that the 5-membered ring is fused at any available position in any orientation.

In some embodiments of NpHet-2, Q=O.
In some embodiments of NpHet-2, Q=S.
In some embodiments of NpHet-2, Q=Se.
In some embodiments of NpHet-2, Q=Te.

In some embodiments of Formula I, NpHet has Formula NpHet-2 and is selected from one of the isomers below, substituted derivatives thereof, and deuterated analogs thereof.

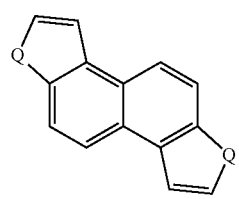
NpHet2-A

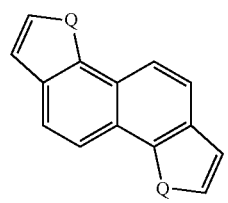
NpHet2-B

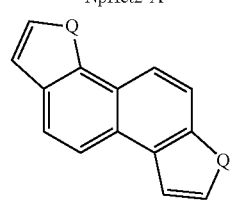
NpHet2-C

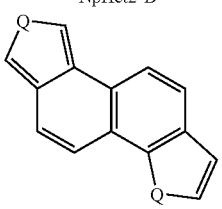
NpHet2-D

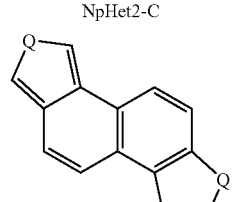
NpHet2-E

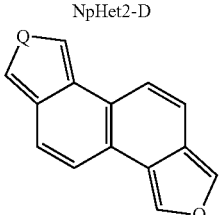
NpHet2-F

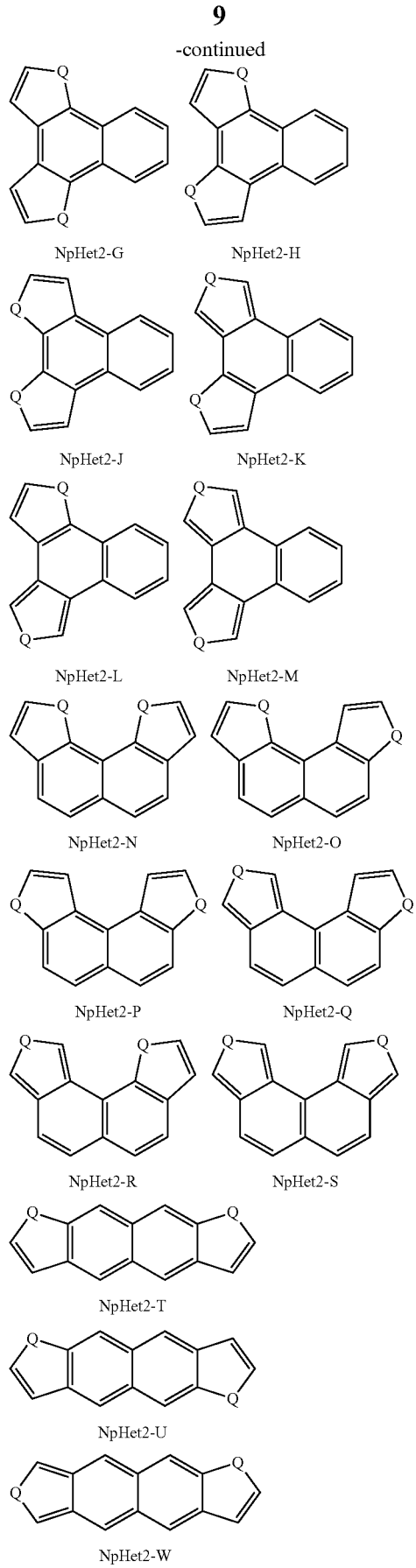

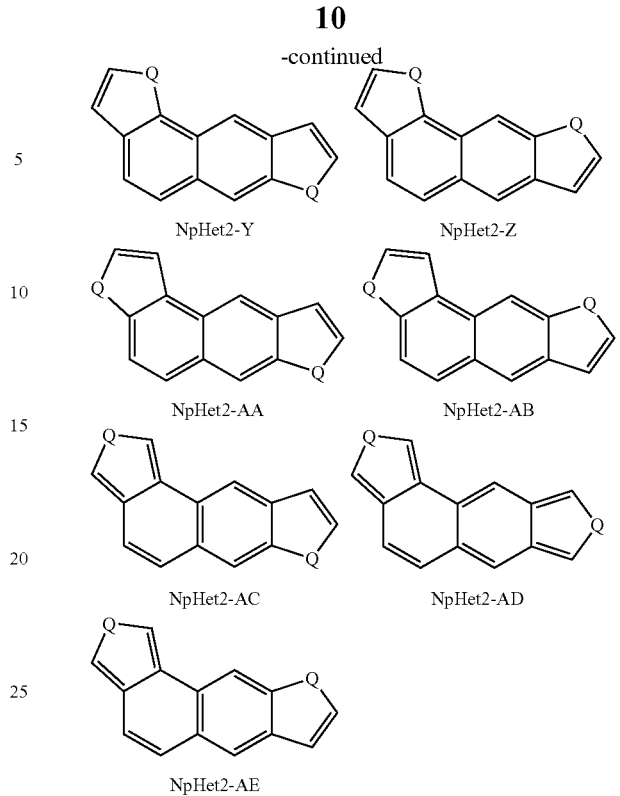

In some embodiments of Formula I, the NpHet is selected from the group consisting of isomers NpHet2-A, NpHet2-B, NpHet2-C, NpHet2-G, NpHet2-H, NpHet2-J, NpHet2-N, NpHet2-O, NpHet2-P, NpHet2-T, NpHet2-U, NpHet2-Y, NpHet2-IZ, NpHet2-AA, NpHet2-AB, substituted derivatives thereof, and deuterated analogs thereof.

In some embodiments of Formula I, the NpHet is selected from isomers NpHet2-A, NpHet2-B, NpHet2-C, substituted derivatives thereof, and deuterated analogs thereof.

In some embodiments of Formula I, the NpHet is selected from isomers NpHet2-D, NpHet2-E, NpHet2-F, substituted derivatives thereof, and deuterated analogs thereof.

In some embodiments of Formula I, the NpHet is selected from isomers NpHet2-G, NpHet2-H, NpHet2-J, substituted derivatives thereof, and deuterated analogs thereof.

In some embodiments of Formula I, the NpHet is selected from isomers NpHet2-K, NpHet2-L, NpHet2-M, substituted derivatives thereof, and deuterated analogs thereof.

In some embodiments of Formula I, the NpHet is selected from isomers NpHet2-N, NpHet2-O, NpHet2-P, substituted derivatives thereof, and deuterated analogs thereof.

In some embodiments of Formula I, the NpHet is selected from isomers NpHet2-Q, NpHet2-R, NpHet2-S, substituted derivatives thereof, and deuterated analogs thereof.

In some embodiments of Formula I, the NpHet is selected from isomers NpHet2-T, NpHet2-U, NpHet2-W, substituted derivatives thereof, and deuterated analogs thereof.

In some embodiments of Formula I, the NpHet is selected from isomers NpHet2-Y, NpHet2-Z, NpHet2-AA, NpHet2-AB, substituted derivatives thereof, and deuterated analogs thereof.

In some embodiments of Formula I, NpHet is selected from isomers NpHet2-AC, NpHet2-AD, NpHet2-AE, substituted derivatives thereof, and deuterated analogs thereof.

In some embodiments of Formula I, NpHet has Formula NpHet-3

NpHet-3

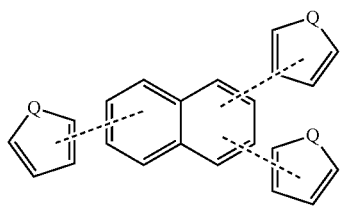

where Q=O, S, Se, or Te and the dashed lines indicate that the 5-membered ring is fused at any available position in any orientation.

In some embodiments of NpHet-3, Q=O.
In some embodiments of NpHet-3, Q=S.
In some embodiments of NpHet-3, Q=Se.
In some embodiments of NpHet-3, Q=Te.

In some embodiments of Formula I, NpHet has Formula NpHet-3 and is selected from one of the isomers below, substituted derivatives thereof, and deuterated analogs thereof.

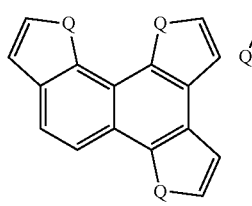 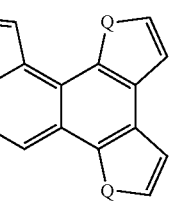

NpHet3-A          NpHet3-B

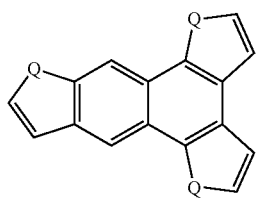 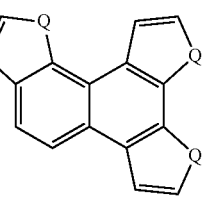

NpHet3-C          NpHet3-D

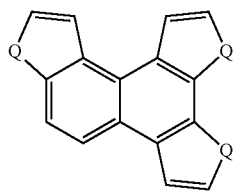 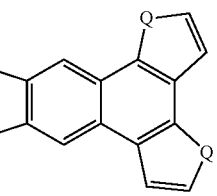

NpHet3-E          NpHet3-F

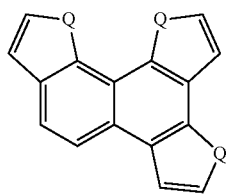 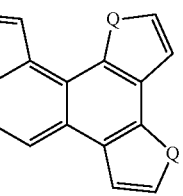

NpHet3-G          NpHet3-H

-continued

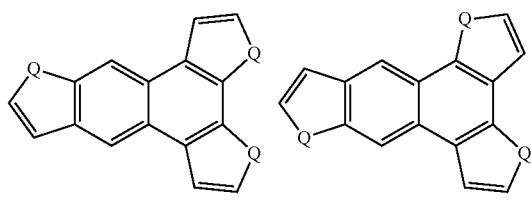

NpHet3-J          NpHet3-K

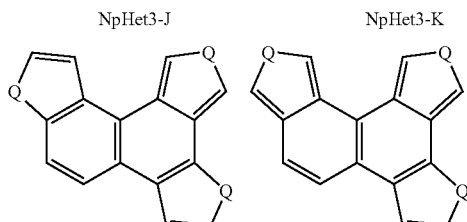

NpHet3-L          NpHet3-M

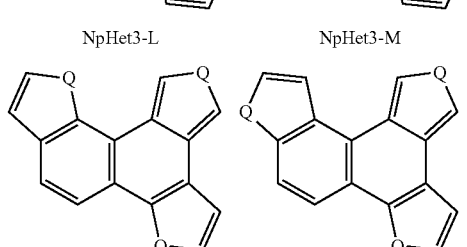

NpHet3-N          NpHet3-O

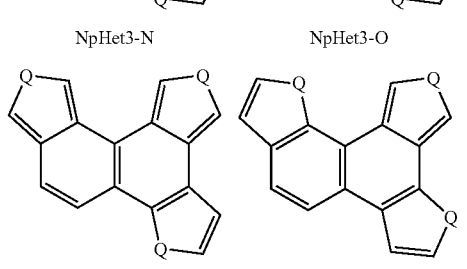

NpHet3-P          NpHet3-Q

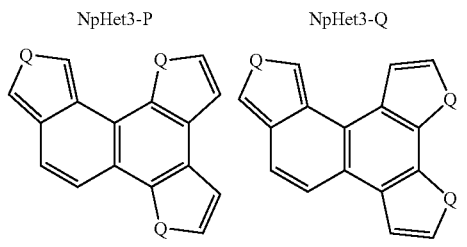

NpHet3-R          NpHet3-S

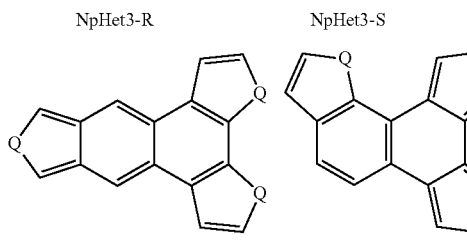

NpHet3-T          NpHet3-U

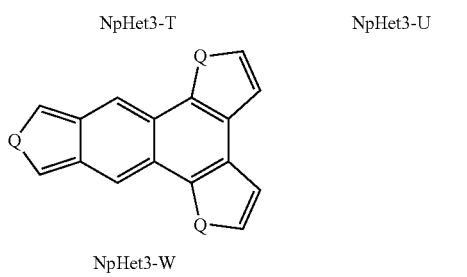

NpHet3-W

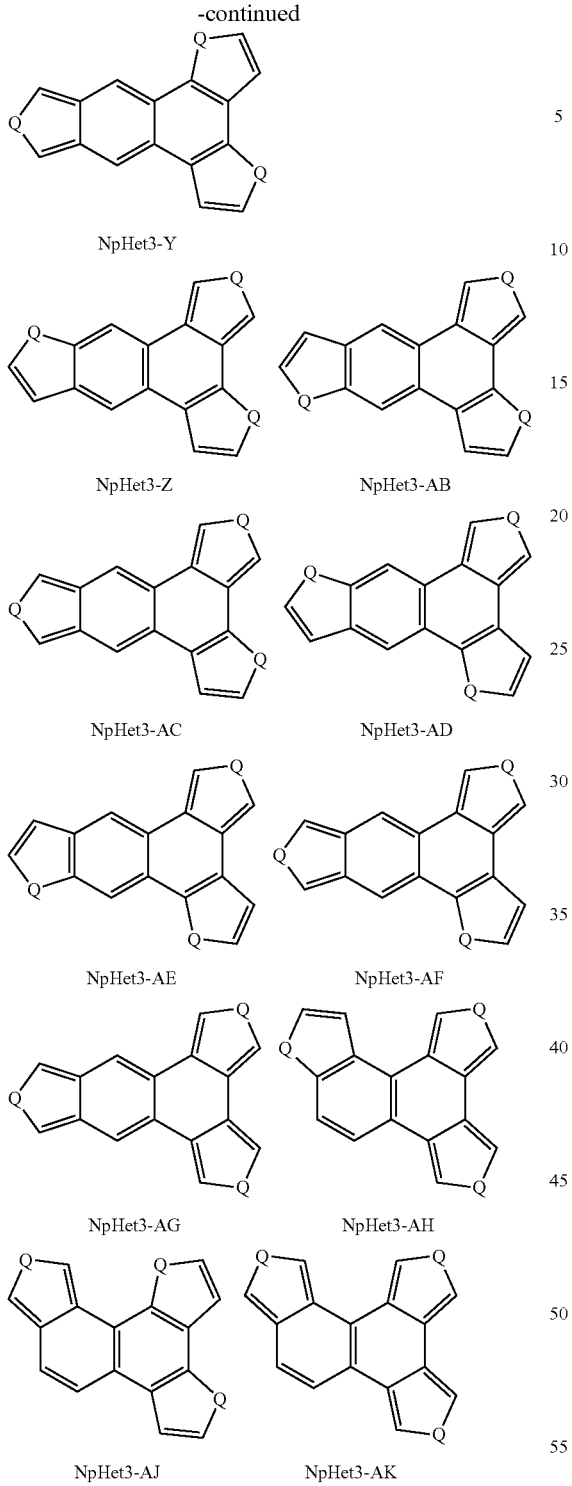

In some embodiments of Formula I, NpHet has Formula NpHet-4

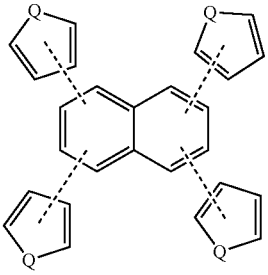

where Q=O, S, Se, or Te and the dashed lines indicate that the 5-membered ring is fused at any available position in any orientation.

In some embodiments of NpHet-4, Q=O.
In some embodiments of NpHet-4, Q=S.
In some embodiments of NpHet-4, Q=Se.
In some embodiments of NpHet-4, Q=Te.

In some embodiments of Formula I, NpHet has Formula NpHet-4 and is selected from one of the isomers below, substituted derivatives thereof, and deuterated analogs thereof.

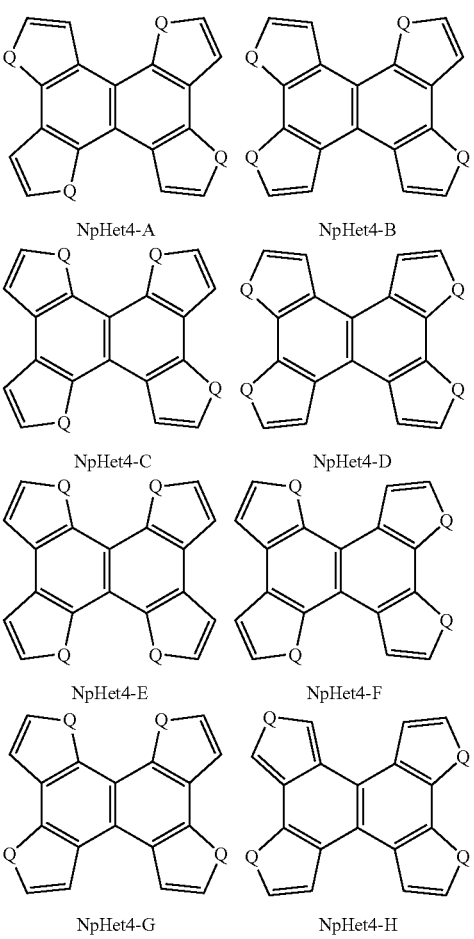

In some embodiments of Formula I, NpHet is selected from isomers NpHet3-A through NpHet3-K, substituted derivatives thereof, and deuterated analogs thereof.

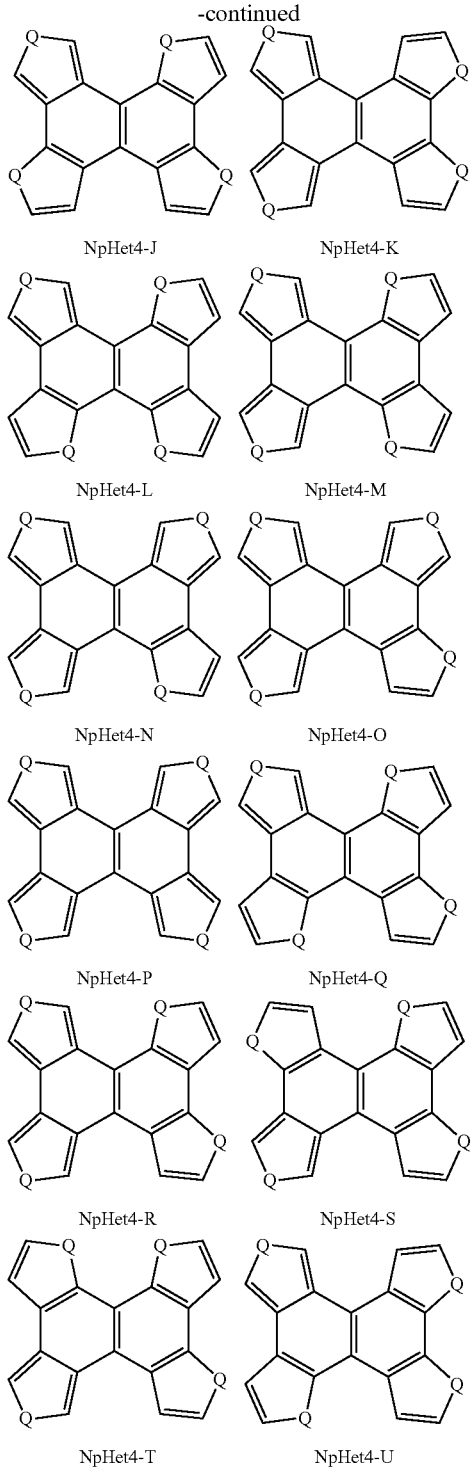

NpHet4-J  NpHet4-K
NpHet4-L  NpHet4-M
NpHet4-N  NpHet4-O
NpHet4-P  NpHet4-Q
NpHet4-R  NpHet4-S
NpHet4-T  NpHet4-U

In some embodiments of Formula I, NpHet is selected from isomers NpHet4-A through NpHet4-G, substituted derivatives thereof, and deuterated analogs thereof.

In some embodiments of Formula I, the group

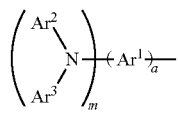

is bonded to a 5-membered heterocyclic ring.

In some embodiments of Formula I, the group

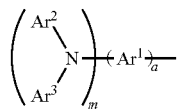

is bonded to a naphthalene ring.

In some embodiments of Formula I, the group

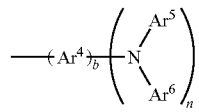

is bonded to a 5-membered heterocyclic ring.

In some embodiments of Formula I, the group

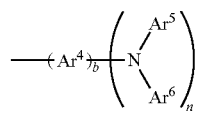

is bonded to a naphthalene ring.

In some embodiments of Formula I, both of the above groups are bonded to 5-membered heterocyclic rings.

In some embodiments of Formula I, one of the above groups is bonded to one naphthalene ring and the other group is bonded to the other naphthalene ring.

In some embodiments of Formula I, a≠b.
In some embodiments of Formula I, a=b=0.
In some embodiments of Formula I, a=b=1.
In some embodiments of Formula I, m≠n.
In some embodiments of Formula I, m=n=0.
In some embodiments of Formula I, m=n=1.
In some embodiments of Formula I, a+b+m+n=1.
In some embodiments of Formula I, a+b+m+n=2.
In some embodiments of Formula I, a+b+m+n=3.
In some embodiments of Formula I, a+b+m+n=4.
In some embodiments of Formula I, m=n=1 and the compound has Formula I-a

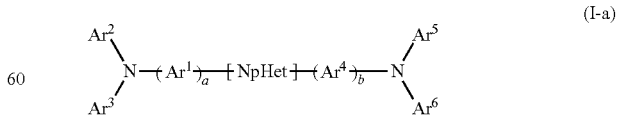

(I-a)

where NpHet, $Ar^1$-$Ar^6$, a and b are as defined above.

In some embodiments of Formula I, m=n=0 a=b=1 and the compound has Formula I-b

 (I-b)

where:
Ar$^{1b}$ and Ar$^{4b}$ are the same or different and are selected from the group consisting of hydrocarbon aryl groups, heteroaryl groups, and deuterated analogs thereof; and NpHet is as defined above.

In some embodiments of Formula I, n=0 and the compound has Formula I-c

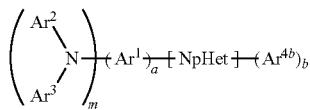

(I-c)

where NpHet, Ar$^1$-Ar$^3$, Ar$^{4b}$, a, b and m are as defined above, with the proviso that a, b, and m are not all 0.

In some embodiments of Formula I, the compound has Formula I-d

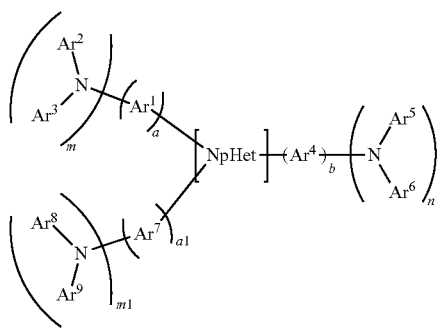

(I-d)

where NpHet, Ar$^1$-Ar$^9$, a, a1, b, m, m1, and n are as defined above, with the proviso that a+m=1 or 2, a1+m1=1 or 2, and b+n=1 or 2. In some embodiments of Formula I-d, m=m1=n=1.

In some embodiments of Formula I, the compound has Formula I-e

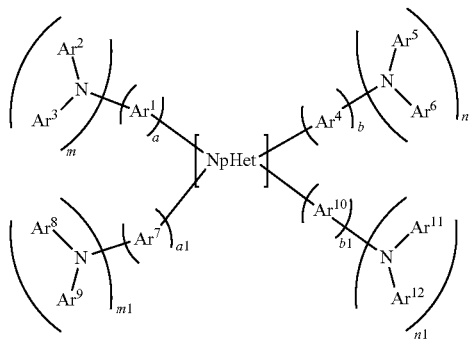

(I-e)

where NpHet, Ar$^1$-Ar$^{12}$, a, a1, b, b1, m, m1, n, and n1 are as defined above, with the proviso that a+m=1 or 2, a1+m1=1 or 2, b+n=1 or 2, and b1+n1=1 or 2. In some embodiments of Formula I-d, m=m1=n=n1=1.

In some embodiments of Formula I, Ar$^1$ is a hydrocarbon aryl or deuterated analog thereof having 6-30 ring carbons; in some embodiments 6-18 ring carbons.

In some embodiments of Formula I, Ar$^1$ is a hydrocarbon aryl having no substituents.

In some embodiments of Formula I, Ar$^1$ is a hydrocarbon aryl having at least one substituent selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula I, Ar$^1$ is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula I, Ar$^1$ is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of D, alkyl, silyl, germyl, deuterated alkyl, deuterated silyl, and deuterated germyl.

In some embodiments of Formula I, Ar$^1$ has Formula c

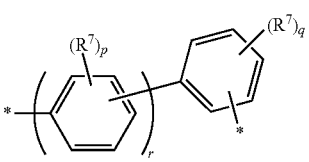

Formula c where:
R$^7$ is the same or different at each occurrence and is selected from the group consisting of D, alkyl, silyl, germyl, deuterated alkyl, deuterated silyl, deuterated germyl;
p is the same or different at each occurrence and is an integer from 0-4;
q is an integer from 0-4;
r is an integer from 0 to 5; and
* indicates a point of attachment.

When m=0 in Formula I, there is no second point of attachment in Formula c.

In some embodiments of Formula I, Ar$^1$ has Formula d

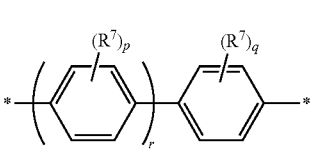

Formula d where R$^7$, p, q, r and * are as in Formula c. When m=0 in Formula I, there is no second point of attachment in Formula d.

In some embodiments of Formula I, Ar$^1$ is a heteroaryl or deuterated heteroaryl having 3-30 ring carbons; in some embodiments, 3-18 ring carbons.

In some embodiments of Formula I, Ar$^1$ is a heteroaryl having no substituents.

In some embodiments of Formula I, Ar$^1$ is a heteroaryl having at least one substituent selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl.

In some embodiments of Formula I, $Ar^1$ is an N-heteroaryl. In some embodiments, the N-heteroaryl is selected from the group consisting of carbazole, diphenylcarbazole, imidazole, benzimidazole, and substituted derivatives thereof.

In some embodiments of Formula I, $Ar^1$ is an O-heteroaryl. In some embodiments, the O-heteroaryl is selected from the group consisting of furan, benzofuran, dibenzofuran, and substituted derivatives thereof.

In some embodiments of Formula I, $Ar^2$ is a hydrocarbon aryl or deuterated analog thereof having 6-30 ring carbons; in some embodiments 6-18 ring carbons.

In some embodiments of Formula I, $Ar^2$ is a hydrocarbon aryl having no substituents.

In some embodiments of Formula I, $Ar^2$ has Formula a

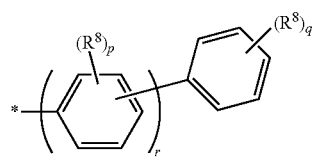

Formula a where:
- $R^8$ is the same or different at each occurrence and is selected from the group consisting of D, alkyl, diarylamino, aryloxy, heteroaryl, alkoxy, siloxy, silyl, germyl, deuterated alkyl, deuterated diarylamino, deuterated aryloxy, deuterated heteroaryl, deuterated alkoxy, deuterated siloxane, deuterated silyl, deuterated germyl, where adjacent $R^8$ groups can be joined together to form a fused ring;
- p is the same or different at each occurrence and is an integer from 0-4;
- q is an integer from 0-5;
- r is an integer from 0 to 5; and
- * indicates a point of attachment.

In some embodiments of Formula I, $Ar^2$ has Formula b

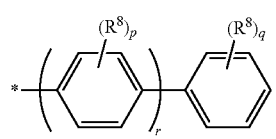

Formula b where $R^8$, p, q, r and * are as in Formula a.

In some embodiments of Formula I, $Ar^2$ is selected from the group consisting of phenyl, biphenyl, terphenyl, 1-naphthyl, 2-naphthyl, anthracenyl, fluorenyl, deuterated analogs thereof, and derivatives thereof having one or more substituents selected from the group consisting of D, alkyl, silyl, germyl, deuterated alkyl, deuterated silyl, and deuterated germyl.

In some embodiments of Formula I, $Ar^2$ is a heteroaryl or deuterated heteroaryl having 3-30 ring carbons; in some embodiments, 3-18 ring carbons.

In some embodiments of Formula I, $Ar^2$ is a heteroaryl having no substituents.

In some embodiments of Formula I, $Ar^2$ has at least one substituent selected from the group consisting of D, F, CN, alkyl, alkoxy, silyl, siloxy, siloxane, germyl, hydrocarbon aryl, heteroaryl, diarylamino, carbazolyl, deuterated alkyl, deuterated alkoxy, deuterated silyl, deuterated siloxy, deuterated siloxane, deuterated germyl, deuterated hydrocarbon aryl, deuterated heteroaryl, deuterated diarylamino, and deuterated carbazolyl.

In some embodiments of Formula I, $Ar^2$ has at least one substituent selected from the group consisting of heteroaryl and deuterated heteroaryl, where the heteroaryl has at least one ring atom which is selected from the group consisting of N, O, and S.

In some embodiments of Formula I, $Ar^2$ has at least one substituent selected from the group consisting of pyrrole, pyridine, pyrimidine, carbazole, imidazole, benzimidazole, imidazolobenzimidazole, triazole, benzotriazole, triazolopyridine, indolocarbazole, phenanthroline, quinoline, isoquinoline, quinoxaline, furan, benzofuran, dibenzofuran, thiophene, benzothiophene, dibenzothiophene, oxazole, benzoxazole, thiazole, benzothiazole, substituted derivatives thereof, and deuterated analogs thereof.

All of the above-described embodiments for $Ar^1$ apply equally to $Ar^4$.

In some embodiments of Formula I, $Ar^1=Ar^4$.

In some embodiments of Formula I, $Ar^1\neq Ar^4$.

All of the above-described embodiments for $Ar^2$ apply equally to $Ar^3$, $Ar^5$, and $Ar^6$.

All of the above-described embodiments for $Ar^2$ in Formula I apply equally to $Ar^{1b}$ and $Ar^{4b}$ in Formula I-b.

All of the above-described embodiments for $Ar^2$ in Formula I apply equally to $Ar^{4b}$ in Formula I-c.

All of the above-described embodiments for $Ar^1$ in Formula I apply equally to $Ar^1$ in Formula I-d and Formula I-e, and to $Ar^{10}$ in Formula I-e.

All of the above-described embodiments for $Ar^2$ in Formula I apply equally to $Ar^6$ and Arg in Formula I-d and Formula I-e, and to $Ar^{11}$ and $Ar^{12}$ in Formula I-e.

In some embodiments of Formula I, $Ar^2=Ar^3$.

In some embodiments of Formula I, $Ar^2\neq Ar^3$.

In some embodiments of Formula I, $Ar^5=Ar^6$.

In some embodiments of Formula I, $Ar^5\neq Ar^6$.

In some embodiments of Formula I, $Ar^2=Ar^6$.

In some embodiments of Formula I, $Ar^3=Ar^5$.

In some embodiments of Formula I, $Ar^2=Ar^6$ and $Ar^3=Ar^5$.

Any of the above embodiments of Formula I can be combined with one or more of the other embodiments, so long as they are not mutually exclusive. For example, the embodiment in which NpHet has structure NpHet2-A can be combined with the embodiment where a=1 and $Ar^1$ has Formula c. The same is true for the other non-mutually-exclusive embodiments discussed above. The skilled person would understand which embodiments were mutually exclusive and would thus readily be able to determine the combinations of embodiments that are contemplated by the present application.

In some embodiments of Formula I, the compound has core isomer NpHet2-A and has Formula II-A or Formula II-B.

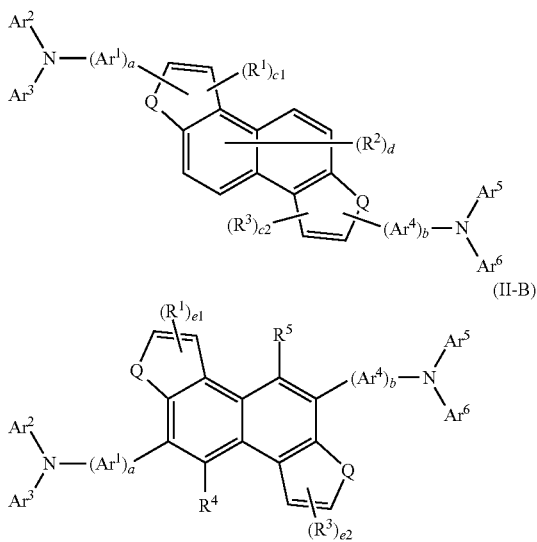

wherein:

Q is O, S, Se, or Te;

$Ar^1$-$Ar^6$ are the same or different and are selected from the group consisting of hydrocarbon aryl groups, heteroaryl groups, and deuterated analogs thereof;

$R^1$ and $R^3$ are the same or different at each occurrence and are selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl;

$R^2$ is the same or different at each occurrence and is selected from the group consisting of D, nitrilo, alkyl, silyl, germyl, hydrocarbon aryl, heteroaryl, deuterated alkyl, deuterated silyl, deuterated germyl, deuterated hydrocarbon aryl, and deuterated heteroaryl;

$R^4$ and $R^5$ are the same or different and are selected from the group consisting of H, D, nitrilo, alkyl, silyl, germyl, hydrocarbon aryl, heteroaryl, deuterated alkyl, deuterated silyl, deuterated germyl, deuterated hydrocarbon aryl, and deuterated heteroaryl;

a, b, c1 and c2 are the same or different and are 0 or 1;

d is an integer from 0-4; and e1 and e2 are the same or different and are an integer from 0-2.

All of the above-described embodiments for Q, $Ar^1$-$Ar^6$, a, and b in Formula I, apply equally to Q, $Ar^1$-$Ar^6$, a, and b in Formula II-A and Formula II-B.

In some embodiments of Formula II-A, c1=0.

In some embodiments of Formula II-A, c1=1.

In some embodiments of Formula II-A, c2=0.

In some embodiments of Formula II-A, c2=1.

In some embodiments of Formula II-A, c1=c2.

In some embodiments of Formula II-A, c1=1 and $R^1$ is D, hydrocarbon aryl, alkylaryl, deuterated hydrocarbon aryl, or deuterated alkylaryl.

In some embodiments of Formula II-A, c1=1 and $R^1$ is D.

In some embodiments of Formula II-A, c1=1 and $R^1$ is hydrocarbon aryl or deuterated aryl having 6-18 ring carbons.

In some embodiments of Formula II-A, c1=1 and $R^1$ has Formula a, as defined above.

In some embodiments of Formula II-A, c1=1 and $R^1$ has Formula b, as defined above.

In some embodiments of Formula II-A, c1=1 and $R^1$ is selected from phenyl, biphenyl, terphenyl, alkyl-substituted derivatives thereof, diarylamino-substituted derivatives thereof, and deuterated analogs thereof.

All of the above-described embodiments for $R^1$ apply equally to $R^3$ when c2=1.

In some embodiments of Formula II-A, d=0.

In some embodiments of Formula II-A, d=1.

In some embodiments of Formula II-A, d=2.

In some embodiments of Formula II-A, d=3.

In some embodiments of Formula II-A, d=4.

In some embodiments of Formula II-A, d>0.

In some embodiments of Formula II-A, d>0 and at least one $R^2$=D.

In some embodiments of Formula II-A, d>0 and at least one $R^2$ is a hydrocarbon aryl or deuterated aryl having 6-18 ring carbons.

In some embodiments of Formula II-A, d>0 and at least one $R^2$ is selected from the group consisting of phenyl, biphenyl, terphenyl, alkyl-substituted derivatives thereof, and deuterated analogs thereof.

In some embodiments of Formula II-A, c1=c2=d=0.

In some embodiments of Formula II-A, c1=c2=1, and d=0.

Any of the above embodiments of Formula II-A can be combined with one or more of the other embodiments, so long as they are not mutually exclusive.

In some embodiments of Formula II-B, e1=0.

In some embodiments of Formula II-B, e1=1.

In some embodiments of Formula II-B, e1=2.

In some embodiments of Formula II-B, e1>0.

In some embodiments of Formula II-B, e2=0.

In some embodiments of Formula II-B, e2=1.

In some embodiments of Formula II-B, e2=2.

In some embodiments of Formula II-B, e2>0.

All of the above-described embodiments for $R^1$ in Formula II-A, apply equally to $R^1$ in Formula II-B when e1>0.

All of the above-described embodiments for $R^3$ in Formula II-A, apply equally to $R^3$ in Formula II-B when e2>0.

In some embodiments of Formula II-B, e1=e2=d=0.

In some embodiments of Formula II-B, e1=e2=1, and d=0.

In some embodiments of Formula II-B, $R^4$=$R^5$.

In some embodiments of Formula II-B, $R^4$≠$R^5$.

In some embodiments of Formula II-B, $R^4$=H or D.

In some embodiments of Formula II-B, $R^4$ is a hydrocarbon aryl or deuterated hydrocarbon aryl having 6-18 ring carbons.

In some embodiments of Formula II-B, $R^4$ is selected from the group consisting of phenyl, biphenyl, terphenyl, alkyl-substituted derivatives thereof, and deuterated analogs thereof.

All of the above-described embodiments for $R^4$ apply equally to $R^5$.

Any of the above embodiments of Formula II-B can be combined with one or more of the other embodiments, so long as they are not mutually exclusive.

In some embodiments of Formula I, the compound has core isomer NpHet2-B and has Formula II-C or Formula II-D.

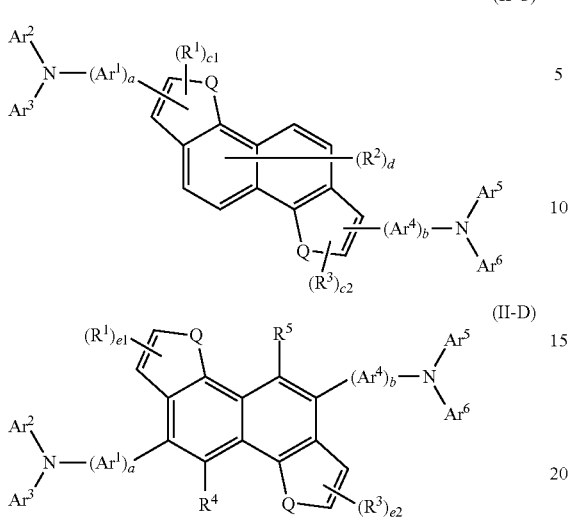

(II-C)

(II-D)

wherein Q, $Ar^1$-$Ar^6$, $R^1$-$R^5$, a, b, c1, d, e1, and e2 are as defined above for Formula II-A and II-B.

All of the above-described embodiments for Q, $Ar^1$-$Ar^6$, $R^1$-$R^5$, a, b, c1, d, e1, and e2 in Formula II-A and Formula II-B, apply equally to $Ar^1$—$Ar^6$, $R^1$-$R^5$, a, b, c1, d, e1, and e2 in Formula II-C and Formula II-D.

Any of the above embodiments of Formula II-C can be combined with one or more of the other embodiments, so long as they are not mutually exclusive.

Any of the above embodiments of Formula II-D can be combined with one or more of the other embodiments, so long as they are not mutually exclusive.

In some embodiments of Formula I, the compound has core isomer NpHet2-C and has Formula II-E, Formula II-E1, Formula II-E2, Formula II-F, or Formula II-F1.

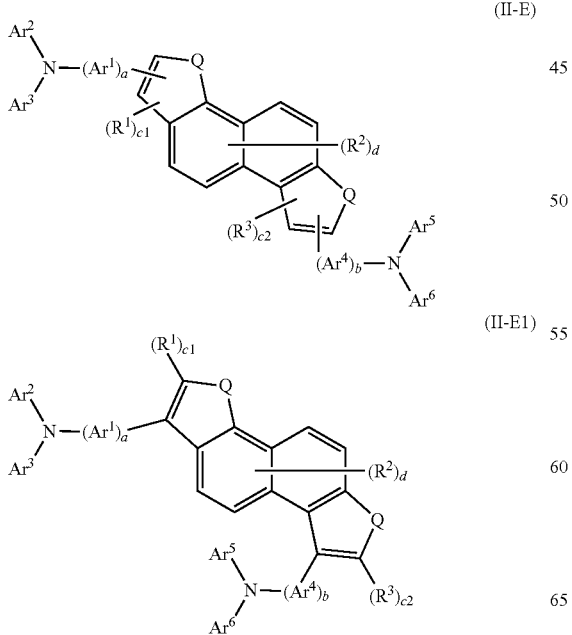

(II-E)

(II-E1)

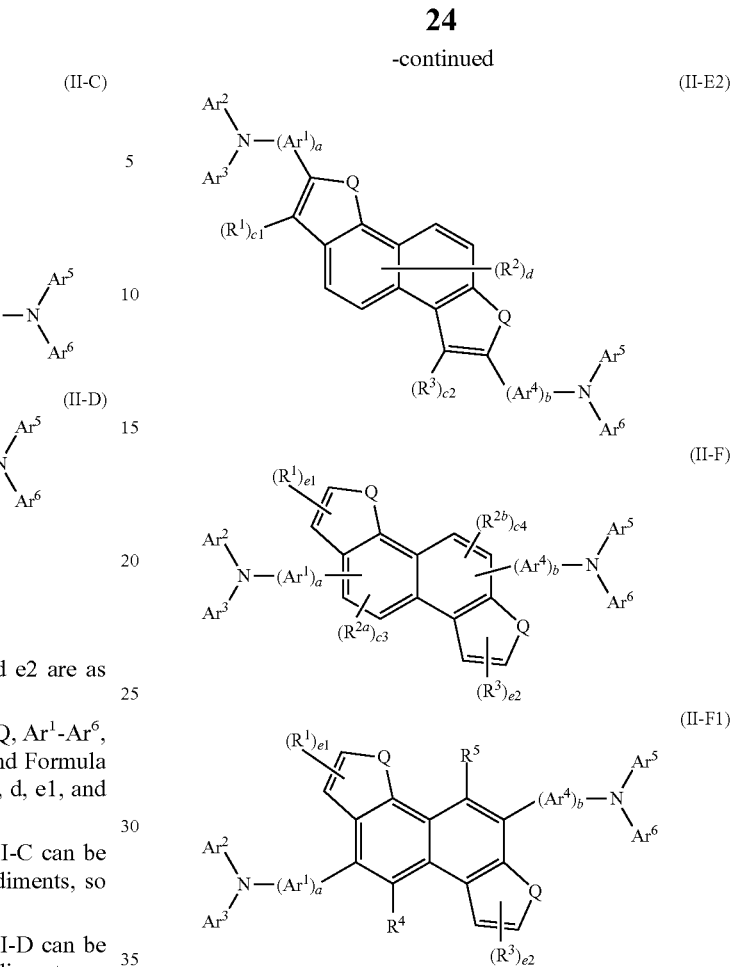

(II-E2)

(II-F)

(II-F1)

wherein:
Q is O, S, Se, or Te;
$Ar^1$-$Ar^6$ are the same or different and are selected from the group consisting of hydrocarbon aryl groups, heteroaryl groups, and deuterated analogs thereof;
$R^1$ and $R^3$ are the same or different at each occurrence and are selected from the group consisting of D, alkyl, silyl, germyl, hydrocarbon aryl, heteroaryl, deuterated alkyl, deuterated silyl, deuterated germyl, deuterated hydrocarbon aryl, and deuterated heteroaryl;
$R^2$ is the same or different at each occurrence and is selected from the group consisting of D, nitrilo, alkyl, silyl, germyl, hydrocarbon aryl, heteroaryl, deuterated alkyl, deuterated silyl, deuterated germyl, deuterated hydrocarbon aryl, and deuterated heteroaryl;
$R^4$ and $R^5$ are the same or different and are selected from the group consisting of H, D, nitrilo, alkyl, silyl, germyl, hydrocarbon aryl, heteroaryl, deuterated alkyl, deuterated silyl, deuterated germyl, deuterated hydrocarbon aryl, and deuterated heteroaryl;
$R^{2a}$ and $R^{2b}$ are the same or different and are selected from the group consisting of D, nitrilo, alkyl, silyl, germyl, hydrocarbon aryl, heteroaryl, deuterated alkyl, deuterated silyl, deuterated germyl, deuterated hydrocarbon aryl, and deuterated heteroaryl;
a, b, c1, c2, c3, and c4 are the same or different and are 0 or 1;
d is an integer from 0-4; and
e1 and e2 are the same or different and are an integer from 0-2.

All of the above-described embodiments for Q, $Ar^1$-$Ar^6$, a, and b in Formula I, apply equally to Q, $Ar^1$-$Ar^6$, a, and b in Formula II-E, Formula II-E1, Formula II-E2, Formula II-F, and Formula II-F1.

All of the above-described embodiments for $R^1$, $R^2$, $R^3$, c1, c2, and d in Formula II-A, apply equally to $R^1$, $R^2$, $R^3$, c1, c2, and d in Formula II-E, Formula II-E1, and Formula II-E2.

Any of the above embodiments of Formula II-E, Formula II-E1, or Formula II-E2 can be combined with one or more of the other embodiments for Formula II-E, Formula II-E1, or Formula II-E2, respectively, so long as they are not mutually exclusive.

In some embodiments of Formula II-F, c3=0.
In some embodiments of Formula II-F, c3=1.
In some embodiments of Formula II-F, c4=0.
In some embodiments of Formula II-F, c4=1.

All of the above-described embodiments for $R^2$ in Formula II-A, apply equally to $R^{2a}$ in Formula II-F when c3=1.

All of the above-described embodiments for $R^2$ in Formula II-A, apply equally to $R^{2b}$ in Formula II-F when c4=1.

All of the above-described embodiments for $R^1$, $R^3$, e1, and e2 in Formula II-D, apply equally to $R^1$, $R^3$, e1, and e2 in Formula II-F.

Any of the above embodiments of Formula II-F can be combined with one or more of the other embodiments, so long as they are not mutually exclusive.

All of the above-described embodiments for $R^1$, $R^3$, $R^4$, $R^5$, e1, and e2 in Formula II-B apply equally to $R^1$, $R^3$, $R^4$, $R^5$, e1, and e2 in Formula II-F1.

Any of the above embodiments of Formula II-F1 can be combined with one or more of the other embodiments, so long as they are not mutually exclusive.

In some embodiments of Formula I, the compound core isomer NpHet2-G and has Formula III-A or Formula III-B.

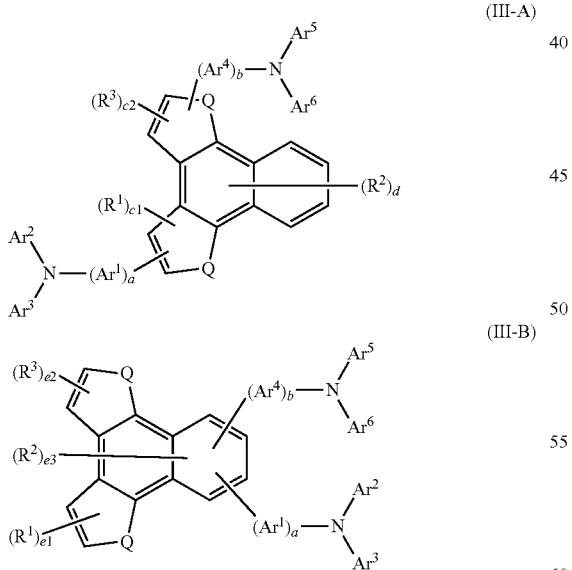

(III-A)

(III-B)

wherein e3 is an integer of 0-2, and Q, $Ar^1$-$Ar^6$, $R^1$-$R^3$, a, b, c1, c2, d, e1, and e2 are as defined above for Formula II-A and Formula II-F.

In some embodiments of Formula III-B, e3=0.
In some embodiments of Formula III-B, e3=1.
In some embodiments of Formula III-B, e3=2.

In some embodiments of Formula III-B, e3>0 and at least one $R^1$ is as described above.

All of the above-described embodiments for Q, $Ar^1$-$Ar^6$, $R^1$-$R^3$, a, b, c1, c2, d, e1, and e2 in Formula II-A and Formula II-F, apply equally to Q, $Ar^1$-$Ar^6$, $R^1$-$R^3$, a, b, c1, c2, d, e1, and e2 in Formula III-A and Formula III-B.

Any of the above embodiments of Formula III-A can be combined with one or more of the other embodiments, so long as they are not mutually exclusive.

Any of the above embodiments of Formula III-B can be combined with one or more of the other embodiments, so long as they are not mutually exclusive.

In some embodiments of Formula I, the compound has core isomer NpHet2-H and has Formula III-C or Formula III-D.

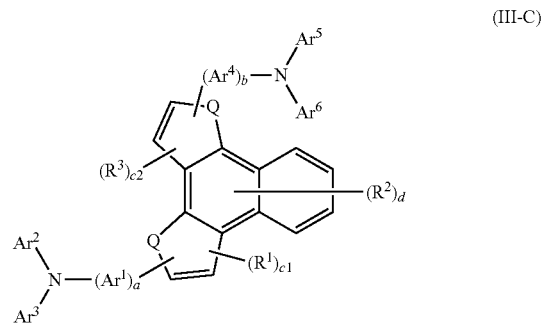

(III-C)

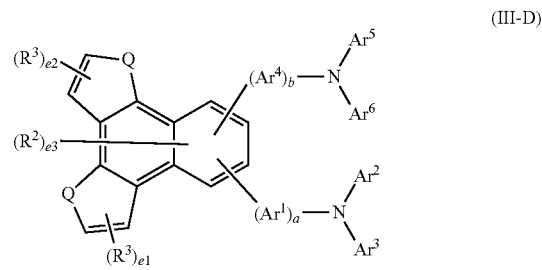

(III-D)

wherein Q, $Ar^1$-$Ar^6$, $R^1$-$R^3$, a, b, c1, c2, d, e1, e2, and e3 are as defined above for Formula III-A and Formula III-B.

All of the above-described embodiments for Q, $R^1$-$R^3$, a, b, c1, c2, d, e1, e2, and e3 in Formula III-A and Formula III-B, apply equally to Q, $Ar^1$-$Ar^6$, $R^1$-$R^3$, a, b, c1, c2, d, e1, e2, and e3 in Formula III-C and Formula III-D.

Any of the above embodiments of Formula III-C can be combined with one or more of the other embodiments, so long as they are not mutually exclusive.

Any of the above embodiments of Formula III-D can be combined with one or more of the other embodiments, so long as they are not mutually exclusive.

In some embodiments of Formula I, the compound has core isomer NpHet2-J and has Formula III-E or Formula III-F.

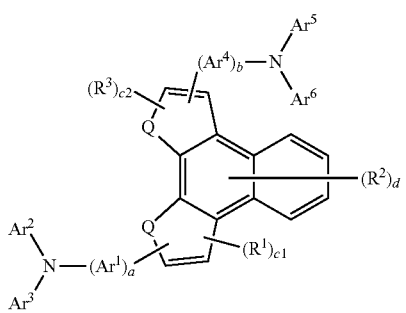

(III-E)

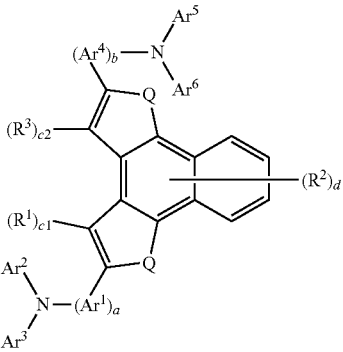

(III-A2)

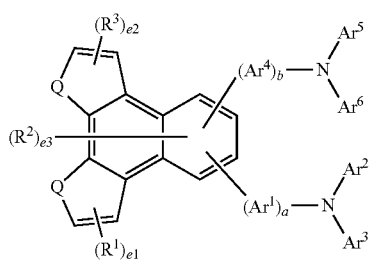

(III-F)

wherein Q, $Ar^1$-$Ar^6$, $R^1$-$R^3$, a, b, c1, c2, and d are as defined above for Formula III-A. All of the above-described embodiments for Q, $Ar^1$-$Ar^6$, $R^1$-$R^3$, a, b, c1, c2, and d in Formula III-A, apply equally to Q, $Ar^1$-$Ar^6$, $R^1$-$R^3$, a, b, c1, c2, and d in Formula III-A1 and Formula III-A2.

Any of the above embodiments of Formula III-A1 or Formula III-A2 can be combined with one or more of the other embodiments of Formula III-A1 or Formula III-A2, respectively, so long as they are not mutually exclusive.

In some embodiments of Formula III-B, the compound has Formula III-B1 wherein Q, $Ar^1$-$Ar^6$, $R^1$-$R^3$, a, b, c1, c2, d, e1, e2, and e3 are as defined above for Formula III-A and Formula III-B.

All of the above-described embodiments for Q, $Ar^1$-$Ar^6$, $R^1$-$R^3$, a, b, c1, c2, d, e1, e2, and e3 in Formula III-A and Formula III-B, apply equally to Q, $Ar^1$-$Ar^6$, $R^1$-$R^3$, a, b, c1, c2, d, e1, e2, and e3 in Formula III-E and Formula III-F.

Any of the above embodiments of Formula III-E can be combined with one or more of the other embodiments, so long as they are not mutually exclusive.

Any of the above embodiments of Formula III-F can be combined with one or more of the other embodiments, so long as they are not mutually exclusive.

In some embodiments of Formula III-A, the compound has Formula III-A1 or Formula III-A2

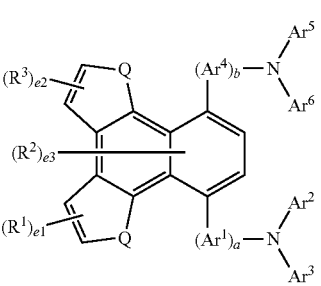

(III-B1)

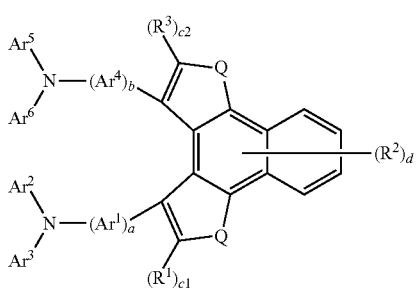

(III-A1)

wherein Q, $Ar^1$-$Ar^6$, $R^1$-$R^3$, a, b, e1, e2, and e3 are as defined above for Formula III-B. All of the above-described embodiments for Q, $Ar^1$-$Ar^6$, $R^1$-$R^3$, a, b, e1, e2, and e3 in Formula III-B, apply equally to Q, $Ar^1$-$Ar^6$, $R^1$-$R^3$, a, b, e1, e2, and e3 in Formula III-B1.

Any of the above embodiments of Formula III-B1 can be combined with one or more of the other embodiments, so long as they are not mutually exclusive.

In some embodiments of Formula III-C, the compound has Formula III-C1

(III-C1)

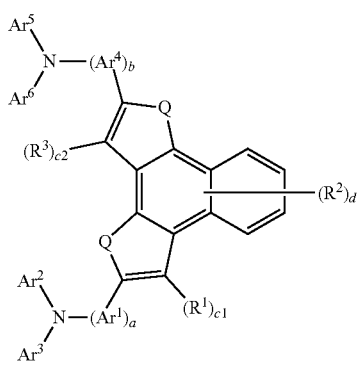

(III-E2)

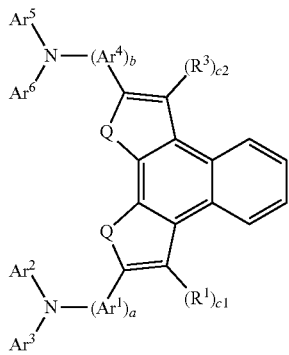

wherein Q, $Ar^1$-$Ar^6$, $R^1$-$R^3$, a, b, c1, c2, and d are as defined above for Formula III-C. All of the above-described embodiments for Q, $Ar^1$-$Ar^6$, $R^1$-$R^3$, a, b, c1, c2, and d in Formula III-C, apply equally to Q, $Ar^1$-$Ar^6$, a, b, c1, c2, and d in Formula III-C1.

Any of the above embodiments of Formula III-C1 can be combined with one or more of the other embodiments, so long as they are not mutually exclusive.

In some embodiments of Formula III-D, the compound has Formula III-D1 wherein Q, $Ar^1$-$Ar^6$, $R^1$, $R^3$, a, b, c1, and c2 are as defined above for Formula III-E. All of the above-described embodiments for Q, $Ar^1$-$Ar^6$, $R^1$, $R^3$, a, b, c1, and c2 in Formula III-E, apply equally to Q, $Ar^1$-$Ar^6$, $R^1$, $R^3$, a, b, c1, and c2 in Formula III-E1 and Formula III-E2.

Any of the above embodiments of Formula III-E1 or Formula III-E2 can be combined with one or more of the other embodiments of Formula III-E1 or Formula III-E2, respectively, so long as they are not mutually exclusive.

In some embodiments of Formula III-F, the compound has Formula III-F1

(III-D1)

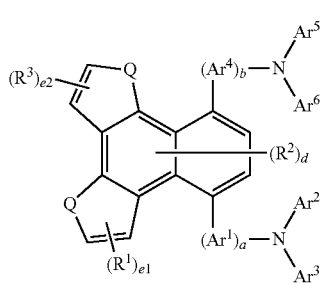

(III-F1)

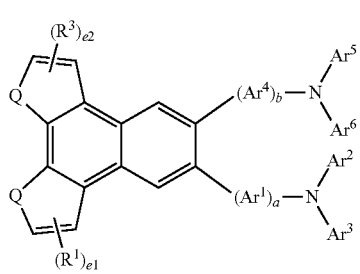

wherein Q, $Ar^1$-$Ar^6$, $R^1$—$R^3$, a, b, d, e1, and e2 are as defined above for Formula III-D. All of the above-described embodiments for Q, $Ar^1$-$Ar^6$, $R^1$-$R^3$, a, b, d, e1, and e2 in Formula III-D, apply equally to Q, $Ar^1$-$Ar^6$, $R^1$-$R^3$, a, b, d, e1, and e2 in Formula III-D1.

Any of the above embodiments of Formula III-D1 can be combined with one or more of the other embodiments, so long as they are not mutually exclusive.

In some embodiments of Formula III-E, the compound has Formula III-E1 or Formula III-E2 wherein Q, $Ar^1$-$Ar^6$, $R^1$, $R^3$, a, b, e1, and e2 are as defined above for Formula III-F. All of the above-described embodiments for Q, $Ar^1$-$Ar^6$, $R^1$, $R^3$, a, b, e1, and e2 in Formula III-F, apply equally to Q, $Ar^1$-$Ar^6$, $R^1$, $R^3$, a, b, e1, and e2 in Formula III-F1.

Any of the above embodiments of Formula III-F1 can be combined with one or more of the other embodiments, so long as they are not mutually exclusive.

In some embodiments of Formula I, the compound has core isomer NpHet2-N and has Formula IV-A or Formula IV-B.

(III-E1)

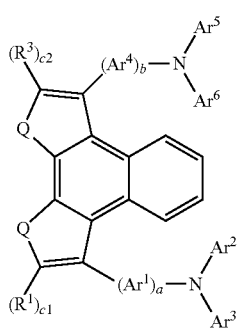

(IV-A)

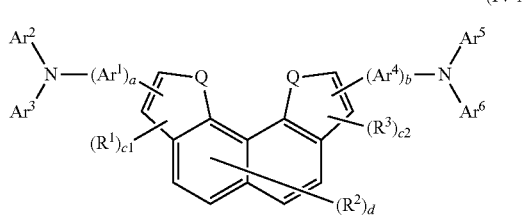

-continued

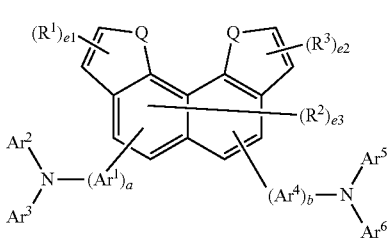
(IV-B)

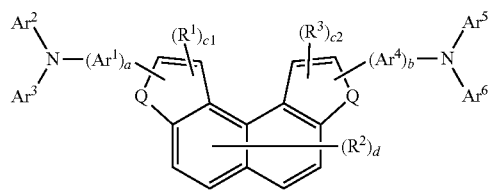
(IV-E)

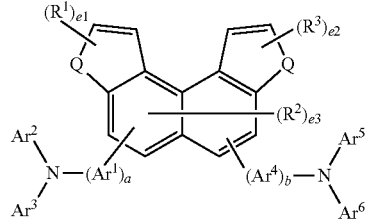
(IV-F)

wherein Q, $Ar^1$-$Ar^6$, $R^1$-$R^3$, a, b, c1, c2, d, e1, e2, and e3 are as defined above for Formula III-A and Formula III-B.

All of the above-described embodiments for Q, $Ar^1$-$Ar^6$, $R^1$-$R^3$, a, b, c1, c2, d, e1, e2, and e3 in Formula III-A and Formula III-B, apply equally to Q, $Ar^1$-$Ar^6$, $R^1$-$R^3$, a, b, c1, c2, d, e1, e2, and e3 in Formula IV-A and Formula IV-B.

Any of the above embodiments of Formula IV-A can be combined with one or more of the other embodiments, so long as they are not mutually exclusive.

Any of the above embodiments of Formula IV-B can be combined with one or more of the other embodiments, so long as they are not mutually exclusive.

In some embodiments of Formula I, the compound has core isomer NpHet2-O and has Formula IV-C or Formula IV-D.

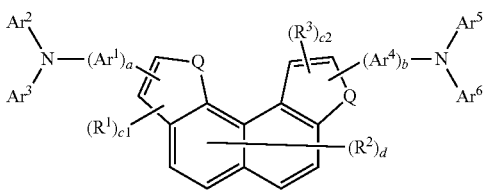
(IV-C)

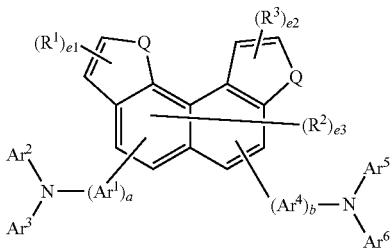
(IV-D)

wherein Q, $Ar^1$-$Ar^6$, $R^1$-$R^3$, a, b, c1, c2, d, e1, e2, and e3 are as defined above for Formula III-A and Formula III-B.

All of the above-described embodiments for Q, $Ar^1$-$Ar^6$, $R^1$-$R^3$, a, b, c1, c2, d, e1, e2, and e3 in Formula III-A and Formula III-B, apply equally to Q, $Ar^1$-$Ar^6$, $R^1$-$R^3$, a, b, c1, c2, d, e1, e2, and e3 in Formula IV-C and Formula IV-D.

Any of the above embodiments of Formula IV-C can be combined with one or more of the other embodiments, so long as they are not mutually exclusive.

Any of the above embodiments of Formula IV-D can be combined with one or more of the other embodiments, so long as they are not mutually exclusive.

In some embodiments of Formula I, the compound has core isomer NpHet2-P and has Formula IV-E or Formula IV-F.

wherein Q, $Ar^1$-$Ar^6$, $R^1$-$R^3$, a, b, c1, c2, d, e1, e2, and e3 are as defined above for Formula III-A and Formula III-B.

All of the above-described embodiments for Q, $Ar^1$-$Ar^6$, $R^1$-$R^3$, a, b, c1, c2, d, e1, e2, and e3 in Formula III-A and Formula III-B, apply equally to Q, $Ar^1$-$Ar^6$, $R^1$-$R^3$, a, b, c1, c2, d, e1, e2, and e3 in Formula IV-E and Formula IV-F.

Any of the above embodiments of Formula IV-E can be combined with one or more of the other embodiments, so long as they are not mutually exclusive.

Any of the above embodiments of Formula IV-F can be combined with one or more of the other embodiments, so long as they are not mutually exclusive.

In some embodiments of Formula I, the compound has core isomer NpHet2-T and has Formula V-A or Formula V-B.

(V-A)

(V-B)

wherein Q, $Ar^1$-$Ar^6$, $R^1$-$R^3$, a, b, c1, c2, d, e1, e2, and e3 are as defined above for Formula III-A and Formula III-B.

All of the above-described embodiments for Q, $Ar^1$-$Ar^6$, $R^1$-$R^3$, a, b, c1, c2, d, e1, e2, and e3 in Formula III-A and Formula III-B, apply equally to Q, $Ar^1$-$Ar^6$, $R^1$-$R^3$, a, b, c1, c2, d, e1, e2, and e3 in Formula V-A and Formula V-B.

Any of the above embodiments of Formula V-A can be combined with one or more of the other embodiments, so long as they are not mutually exclusive.

Any of the above embodiments of Formula V-B can be combined with one or more of the other embodiments, so long as they are not mutually exclusive.

In some embodiments of Formula I, the compound has core isomer NpHet2-U and has Formula V-C or Formula V-D.

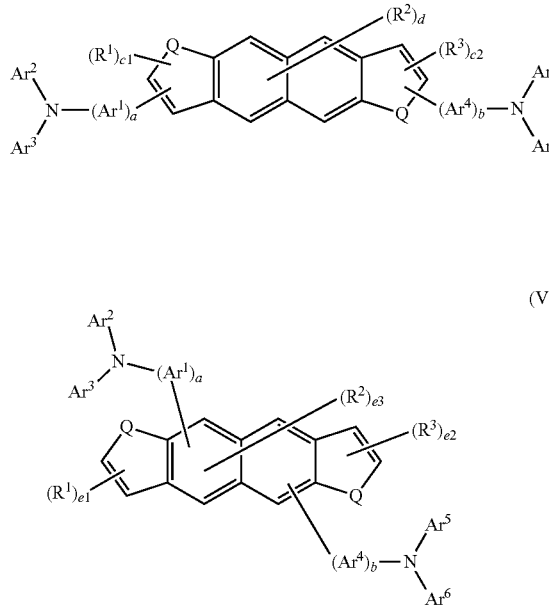

(V-C)

(V-D)

wherein Q, Ar¹-Ar⁶, R¹-R³, a, b, c1, c2, d, e1, e2, and e3 are as defined above for Formula III-A and Formula III-B.

All of the above-described embodiments for Q, Ar¹-Ar⁶, R¹-R³, a, b, c1, c2, d, e1, e2, and e3 in Formula III-A and Formula III-B, apply equally to Q, Ar¹-Ar⁶, R¹-R³, a, b, c1, c2, d, e1, e2, and e3 in Formula V-C and Formula V-D.

Any of the above embodiments of Formula V-C can be combined with one or more of the other embodiments, so long as they are not mutually exclusive.

Any of the above embodiments of Formula V-D can be combined with one or more of the other embodiments, so long as they are not mutually exclusive.

The compounds of Formula I can be made using any technique that will yield a C—C or C—N bond and known polymerization techniques. A variety of such techniques are known, such as Suzuki, Yamamoto, Stille, and metal-catalyzed C—N couplings as well as metal catalyzed and oxidative direct arylation.

Deuterated compounds can be prepared in a similar manner using deuterated precursor materials or, more generally, by treating the non-deuterated compound with deuterated solvent, such as benzene-d6, in the presence of a Lewis acid H/D exchange catalyst, such as trifluoromethanesulfonic acid, aluminum trichloride or ethyl aluminum dichloride. Deuteration reactions have also been described in published PCT application WO2011/053334.

Compounds having core isomer NpHet2-O, where Q=O, can be made according to the following scheme.

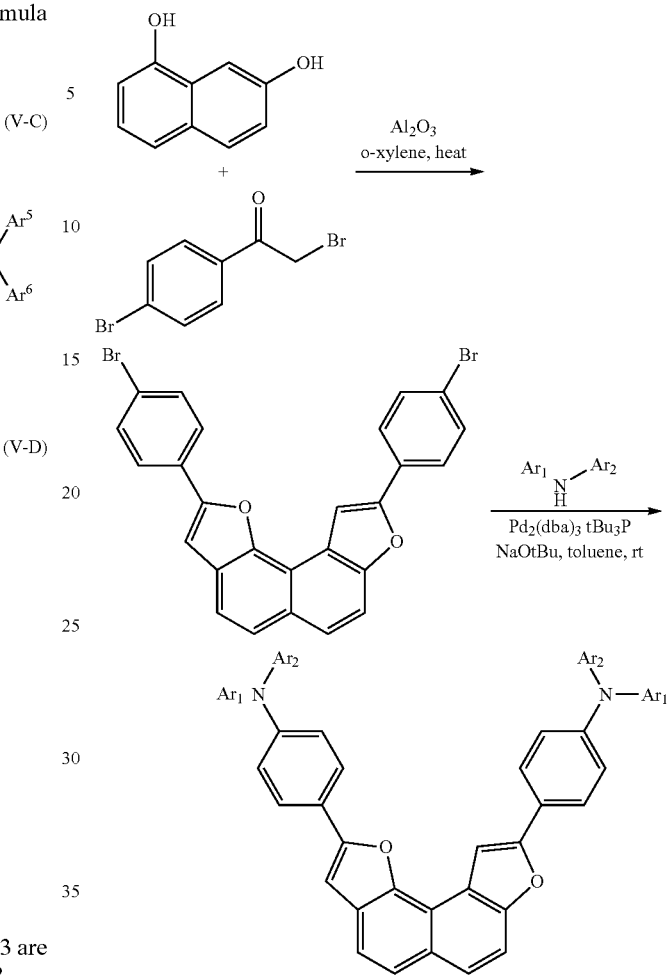

Compounds having core isomer NpHet2-P, where Q=O, can be made according to the following scheme.

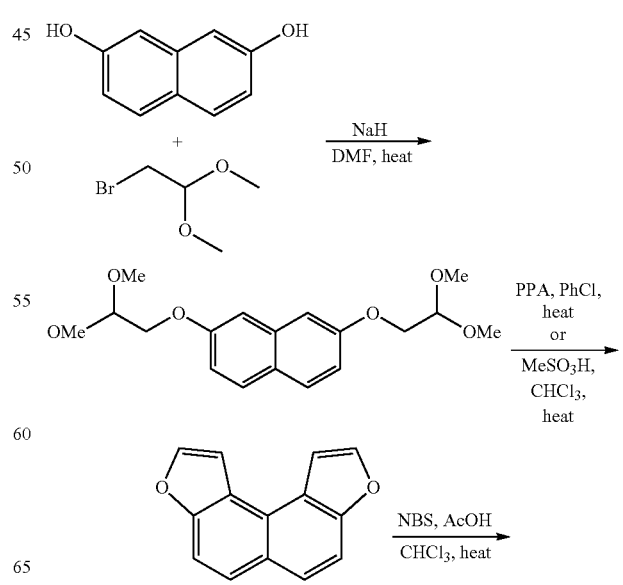

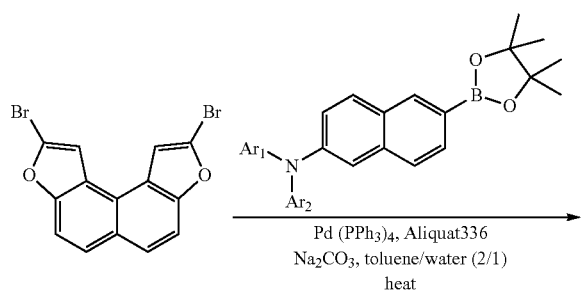
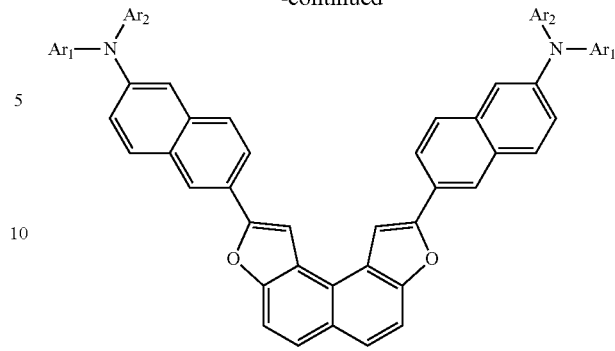
Additional exemplary preparations are given in the Examples.
Examples of compounds having Formula I include, but are not limited to, the compounds shown below.
(a) Compounds having NpHet-1 where Q=O.
Compound 1-1
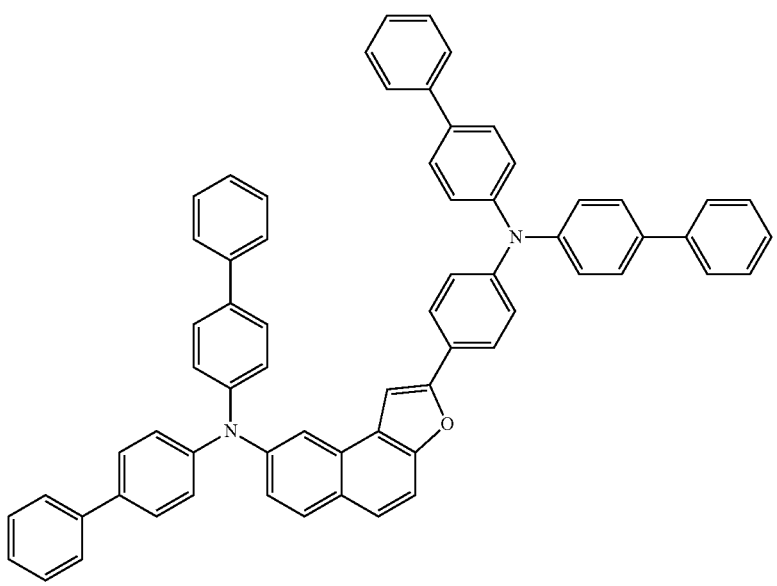
Compound 1-2
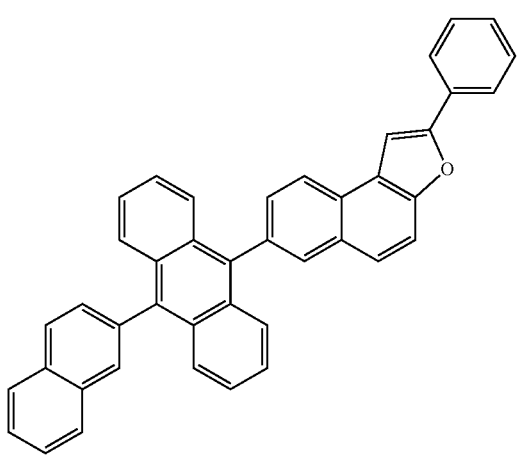

(b) Compounds having NpHet-2 where Q=O.
Compound 2-1
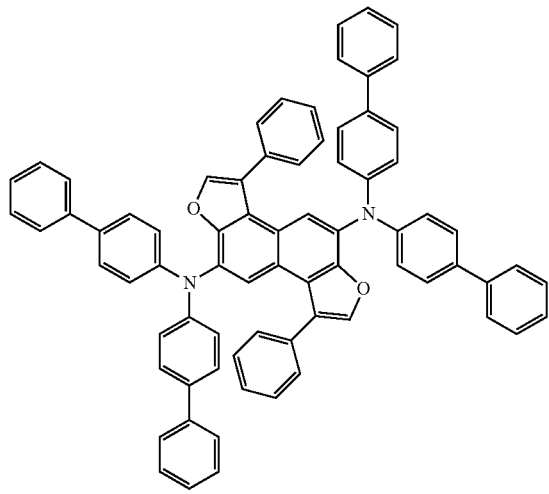
Compound 2-2
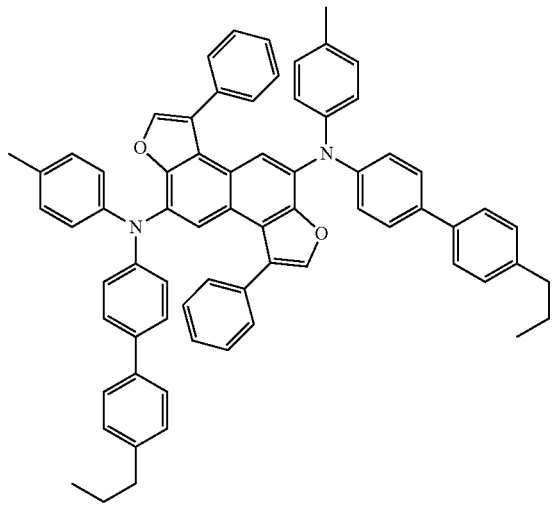
Compound 2-3
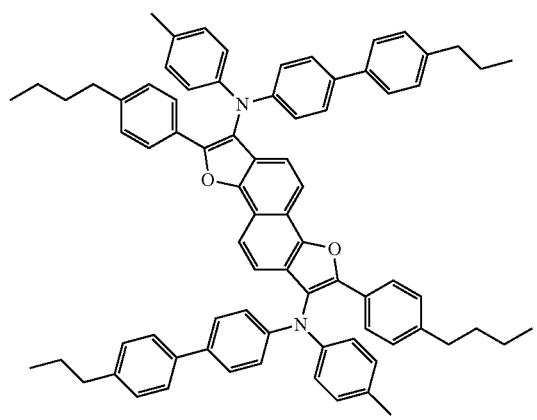
Compound 2-4
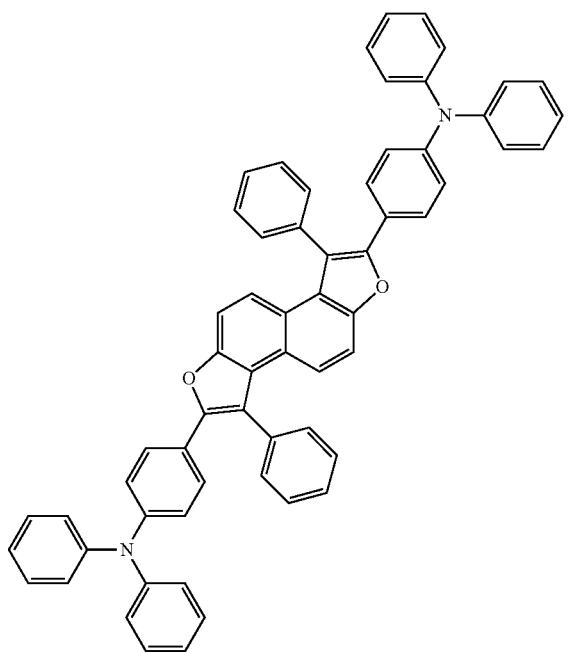
Compound 2-5
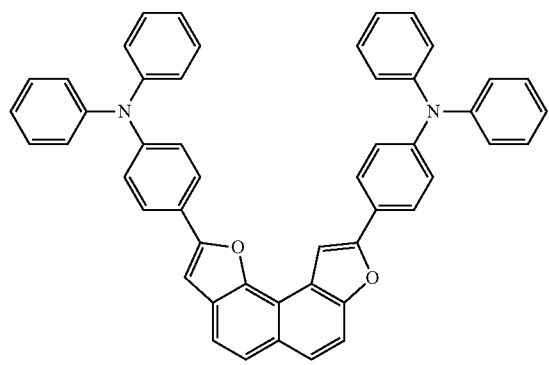
Compound 2-6
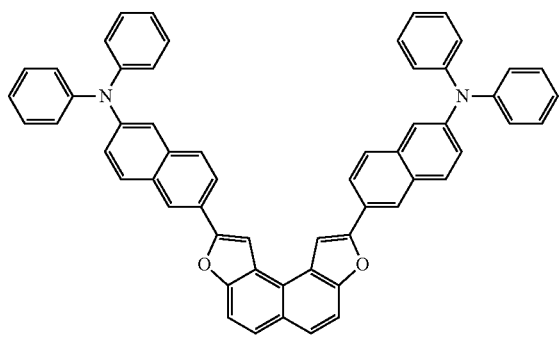

-continued
Compound 2-7
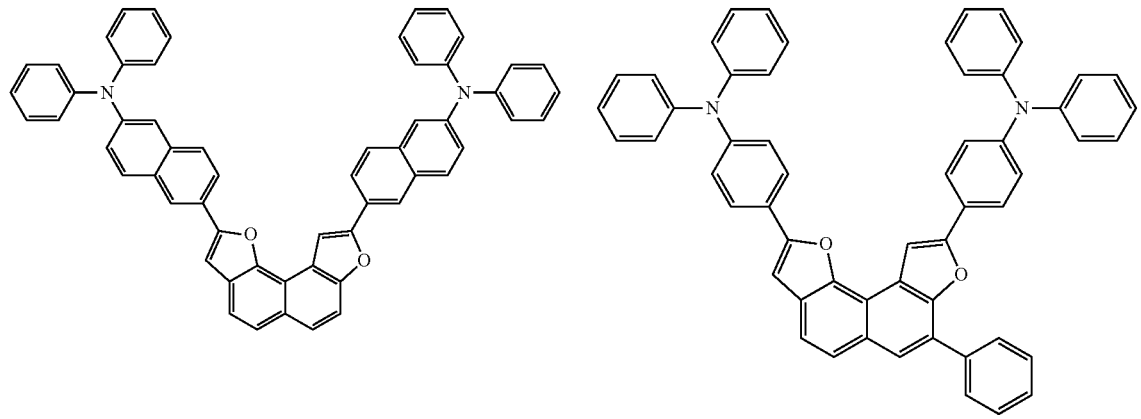
Compound 2-8
Compound 2-9
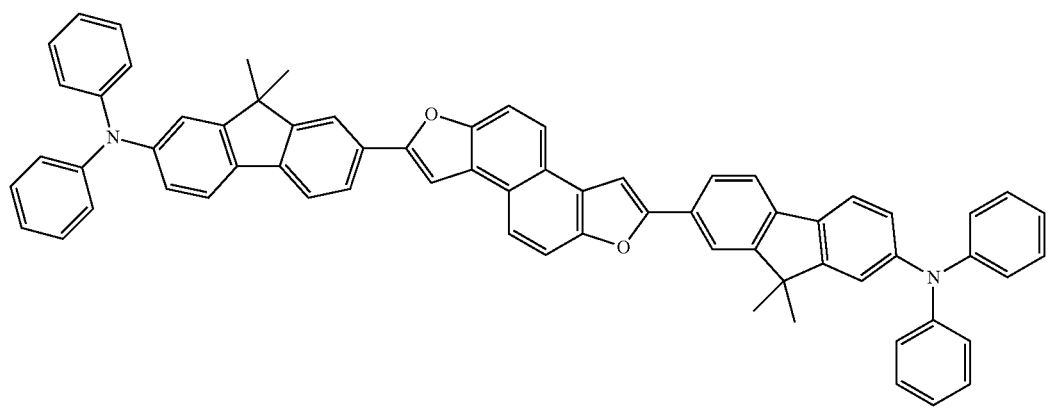
Compound 2-10
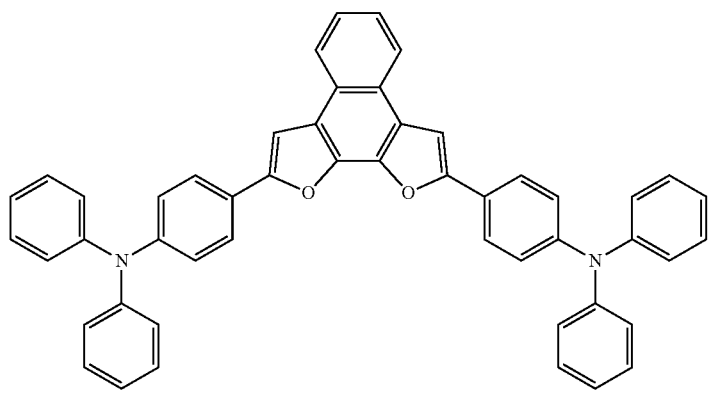
Compound 2-11
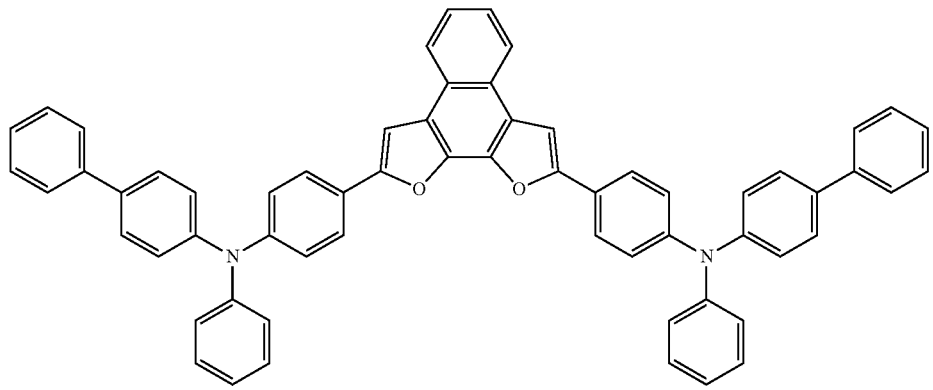

-continued
Compound 2-12
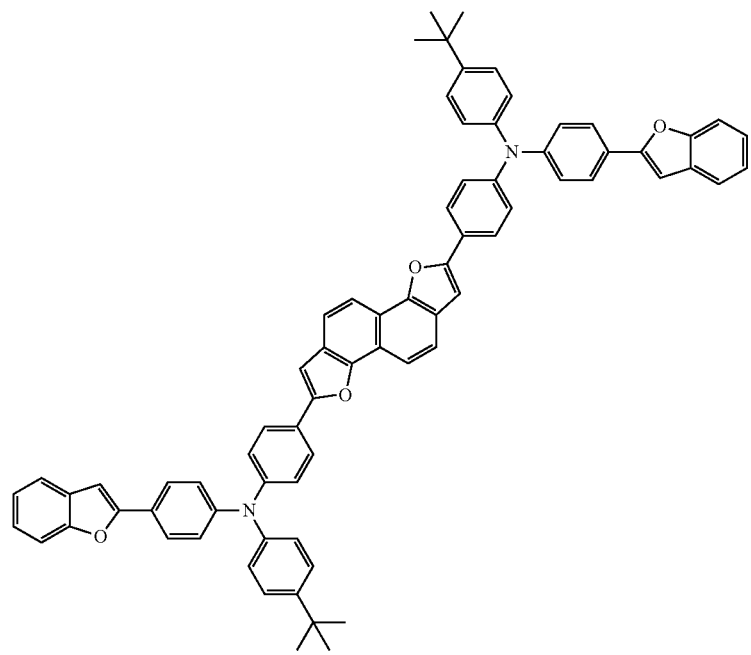
Compound 2-13
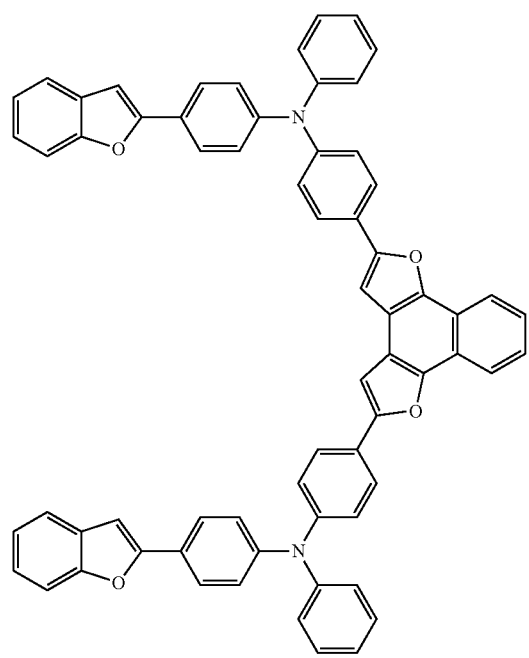

Compound 2-14
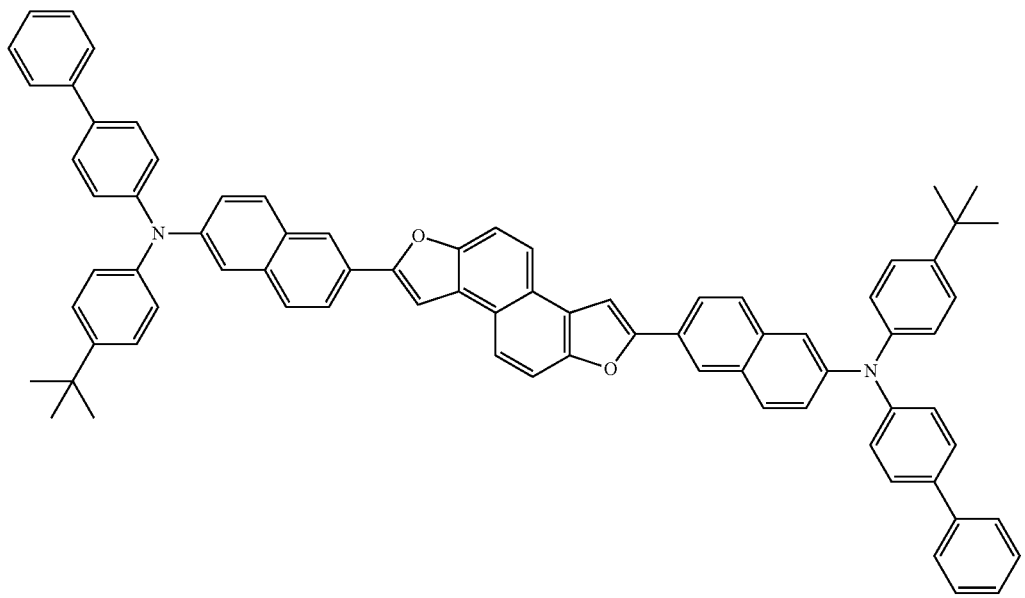
Compound 2-15
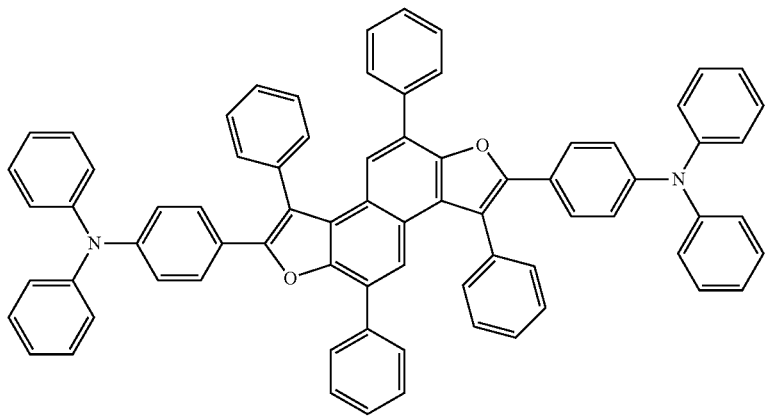
Compound 2-16
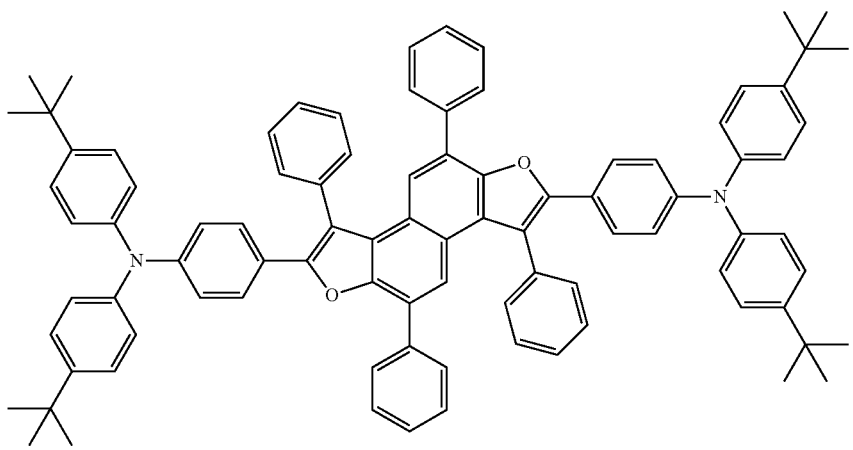

Compound 2-17
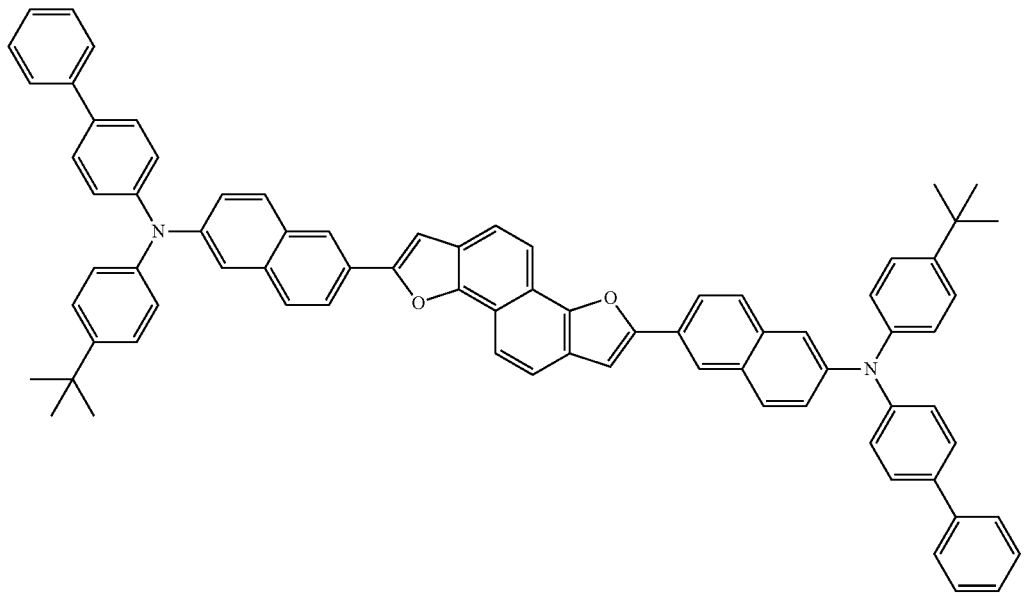
Compound 2-18
Compound 2-19
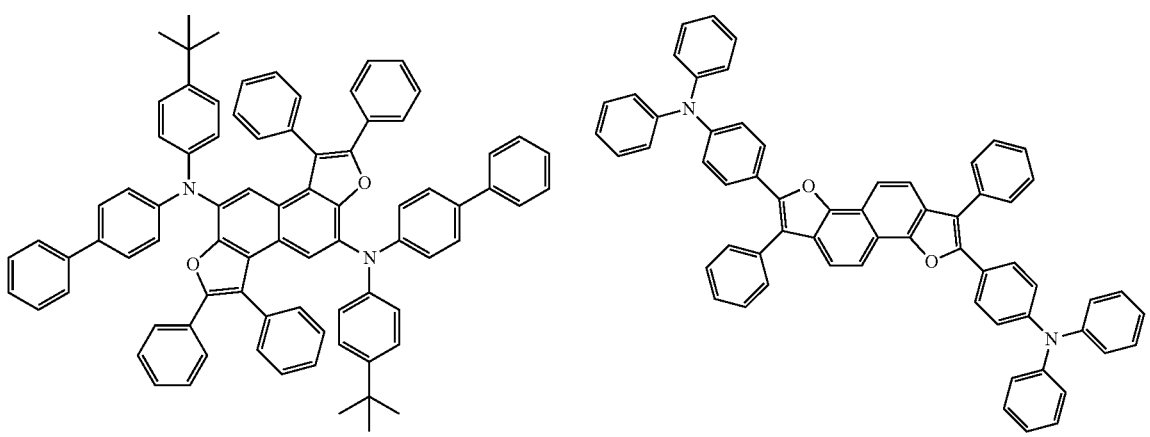
Compound 2-20
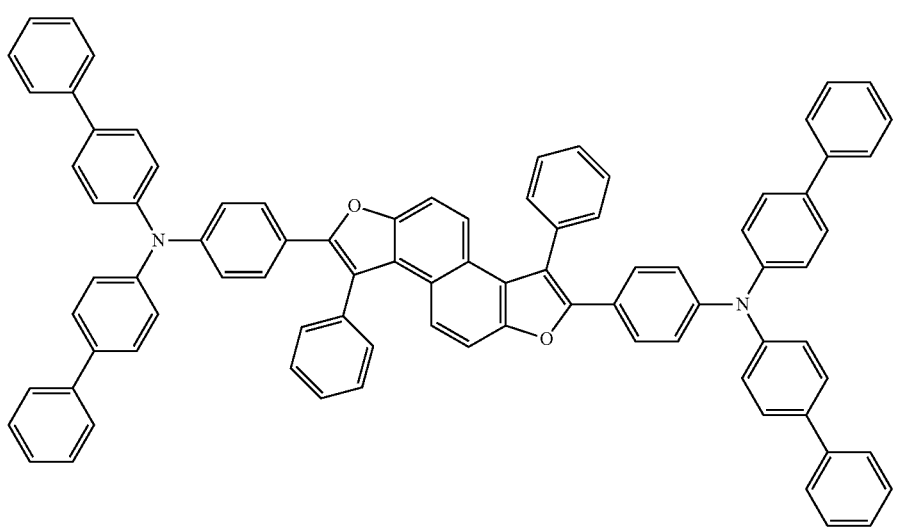

Compound 2-21
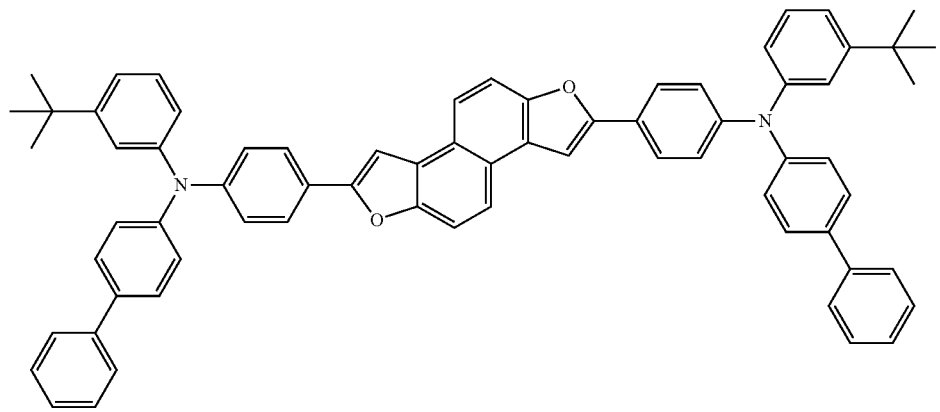
Compound 2-22
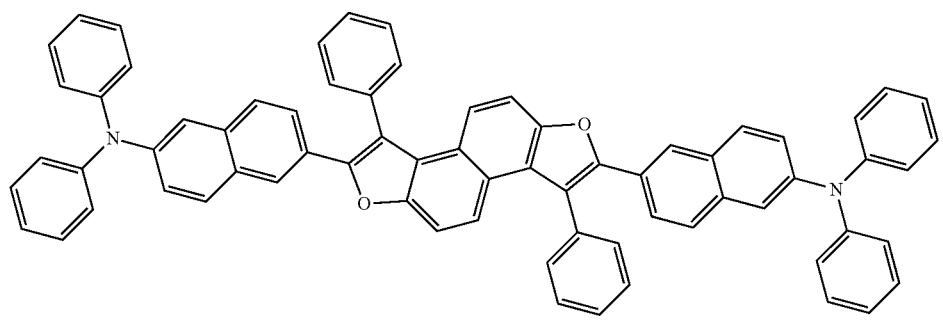
Compound 2-23 [same as Compound 2-10]
Compound 2-24
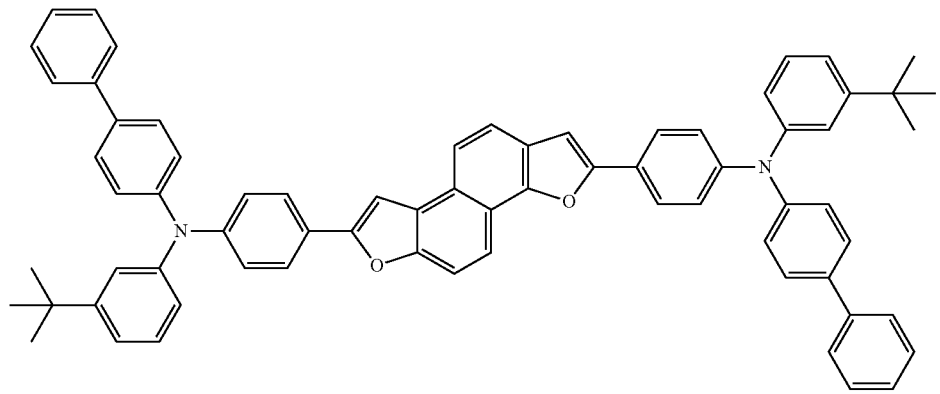

Compound 2-25
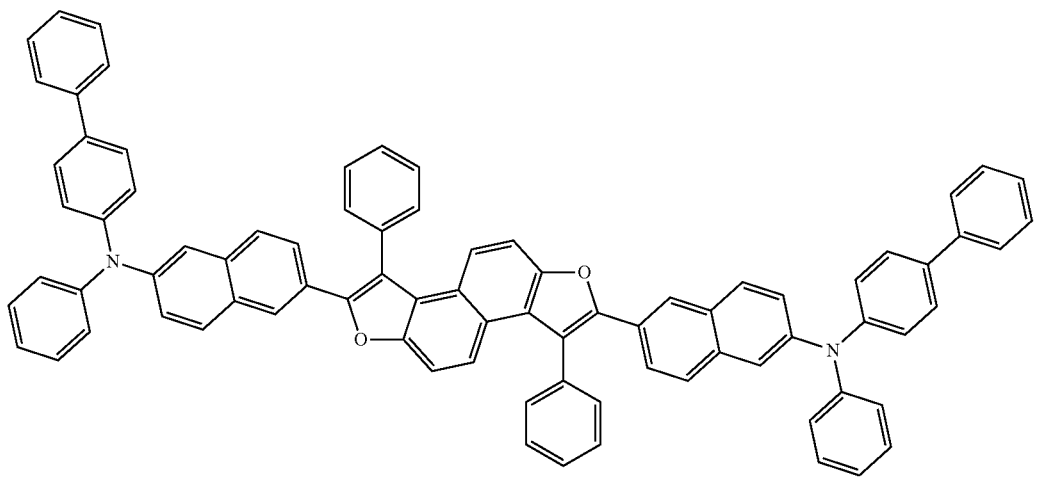
Compound 2-26
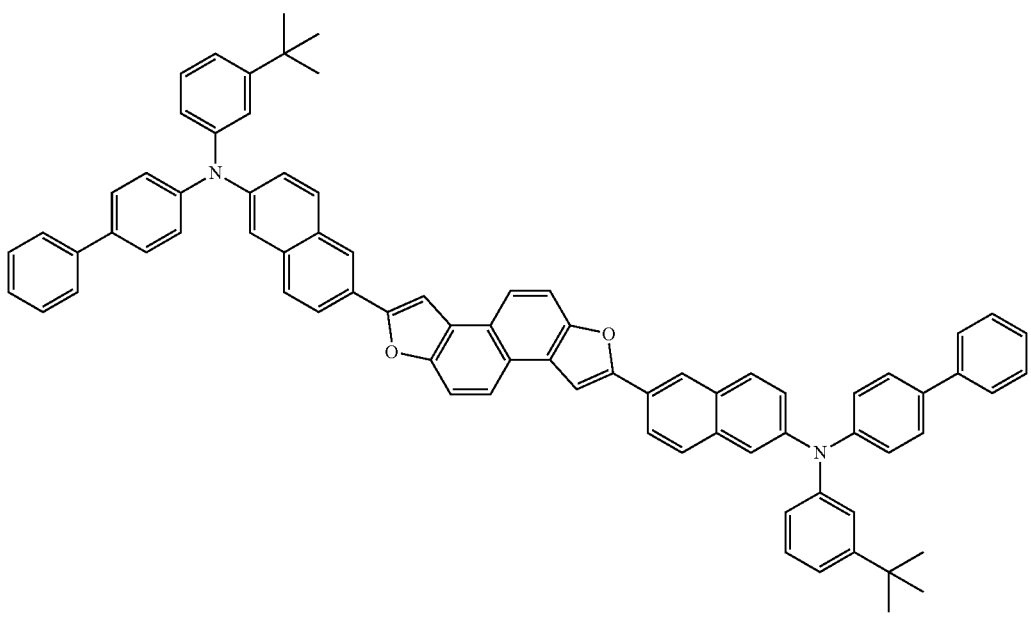

Compound 2-27 [same as Compound 2-11]
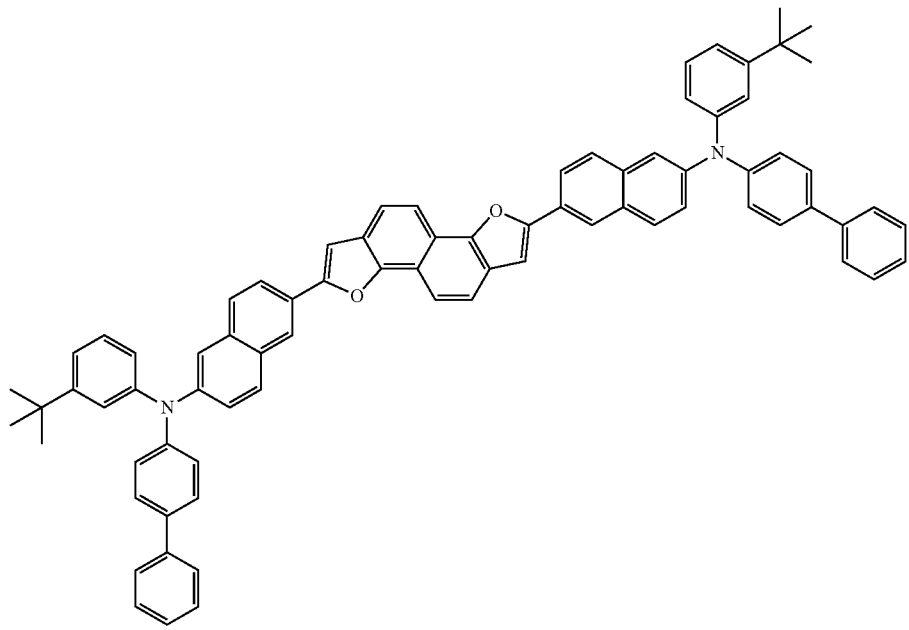
Compound 2-28
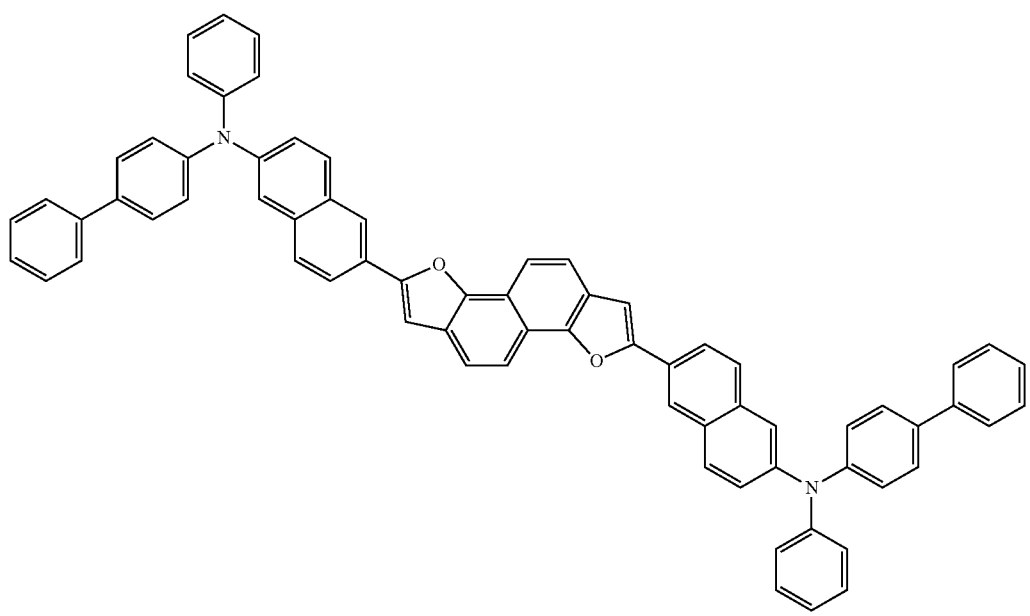
Compound 2-29

Compound 2-30
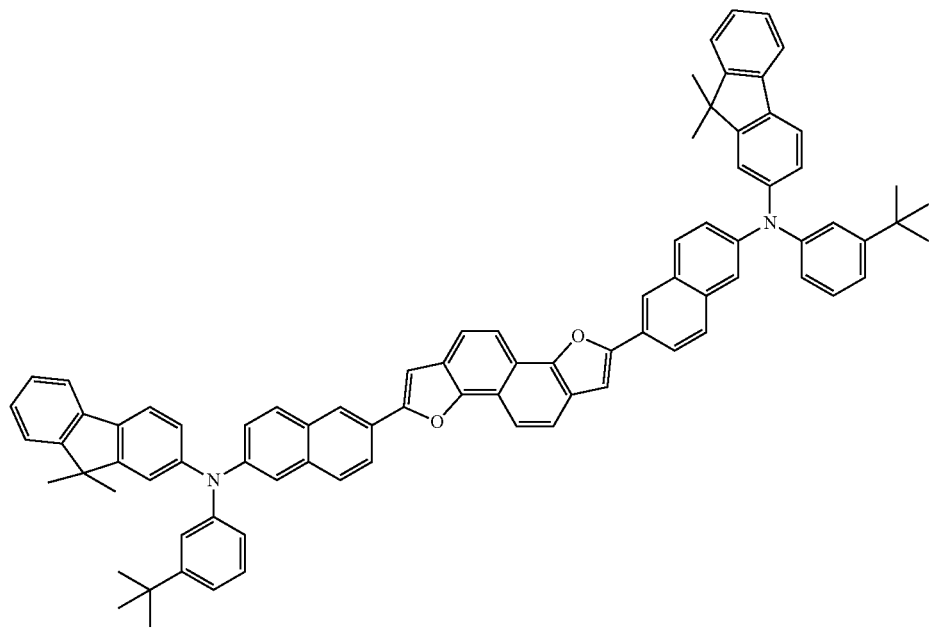
Compound 2-31
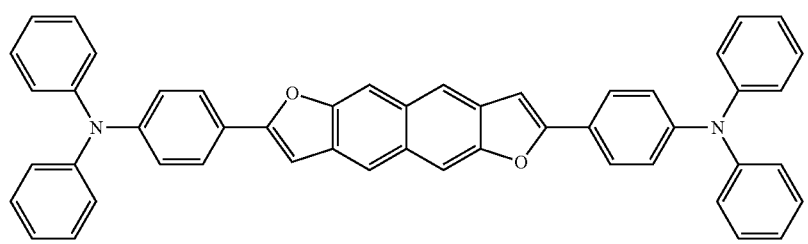
Compound 2-32
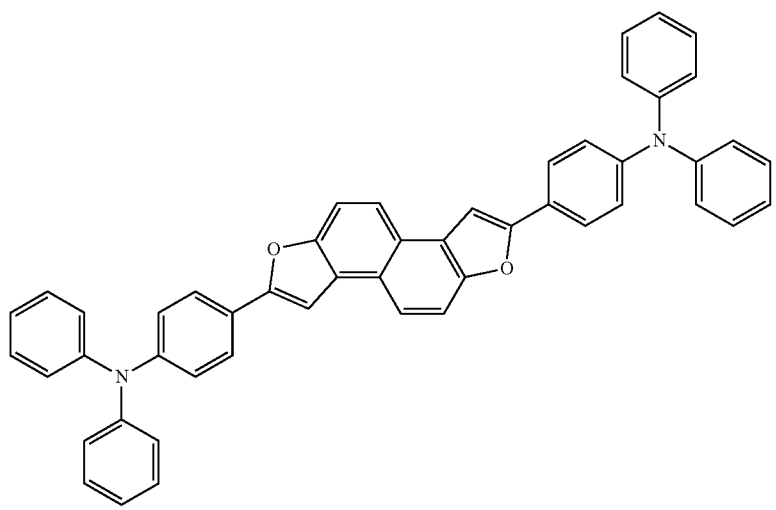

Compound 2-33
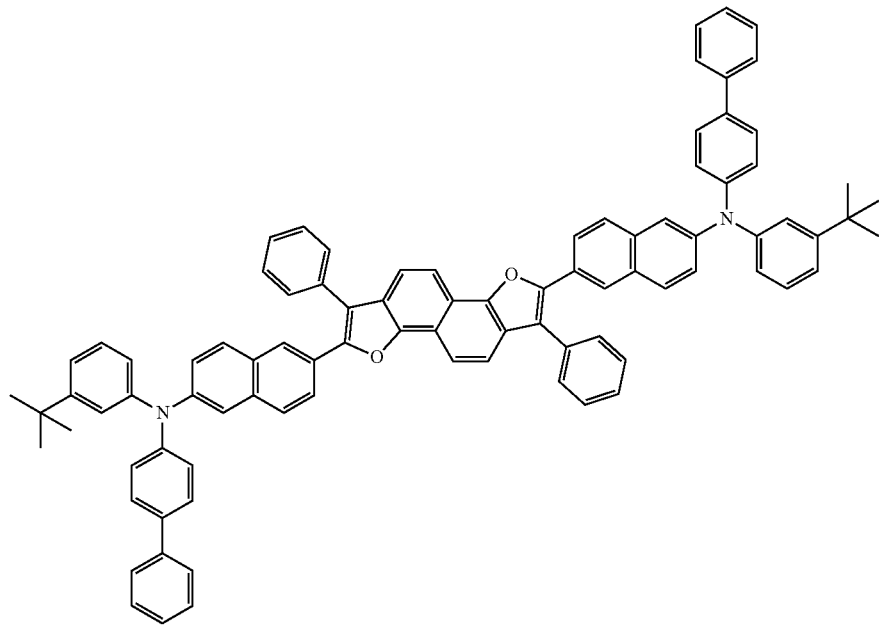
Compound 2-34
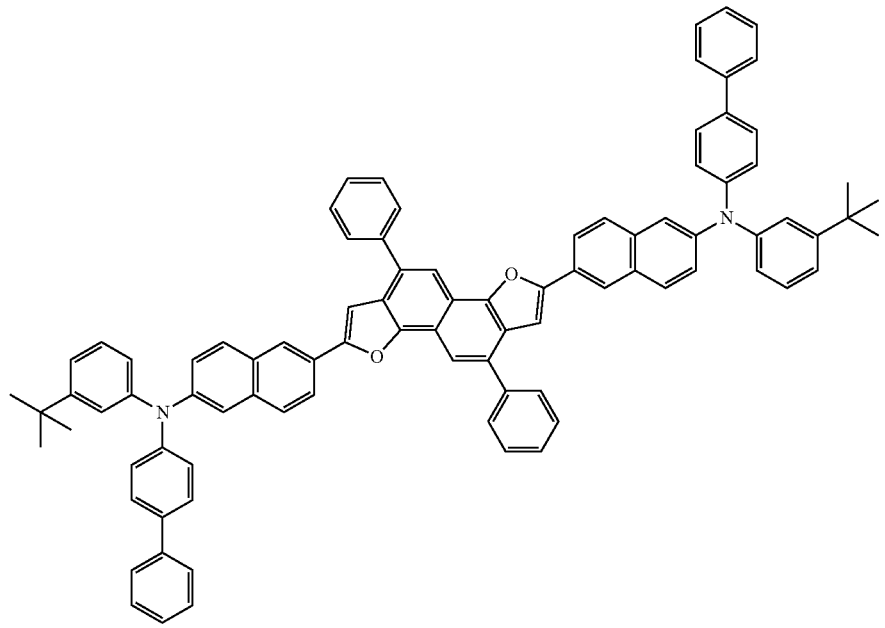
Compound 2-35
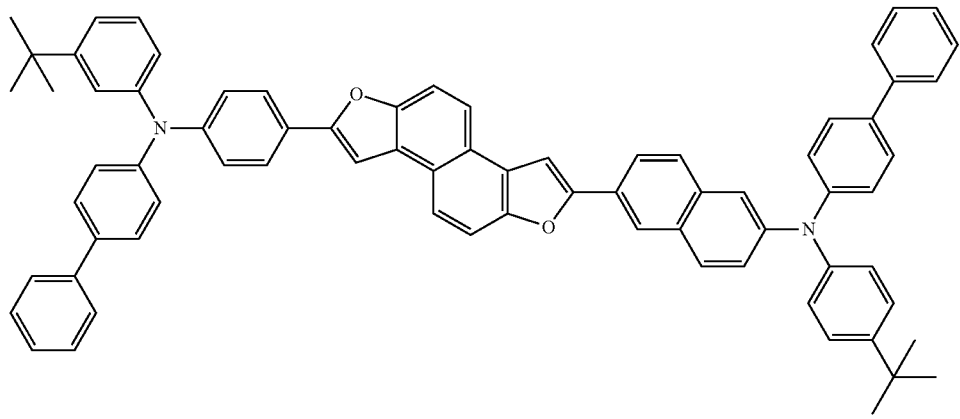

-continued
Compound 2-36
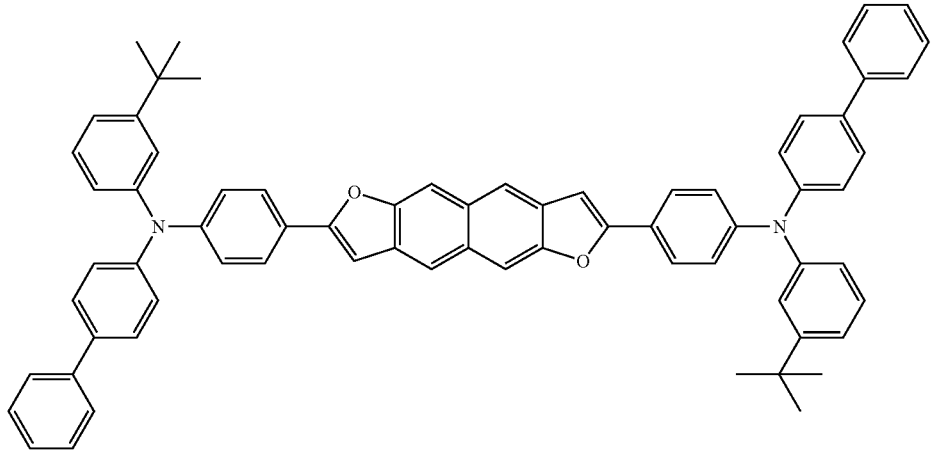
Compound 2-37
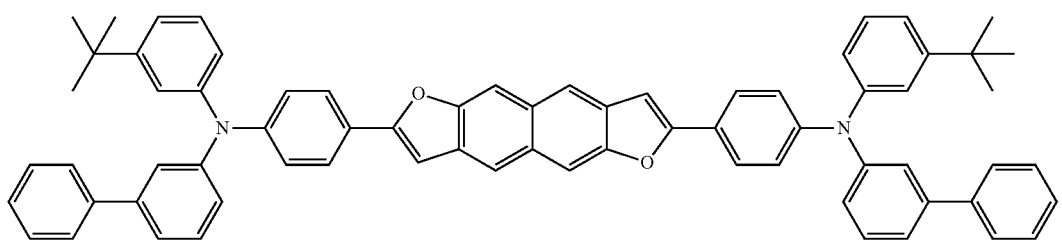
Compound 2-38
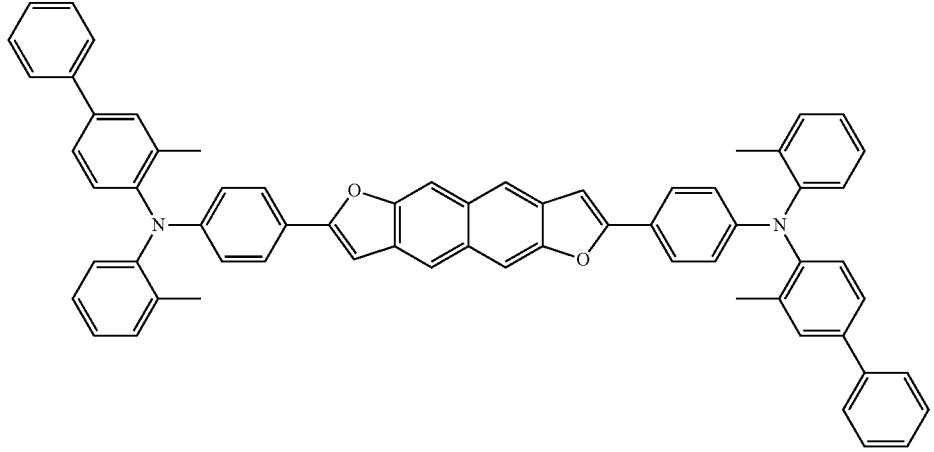
Compound 2-39
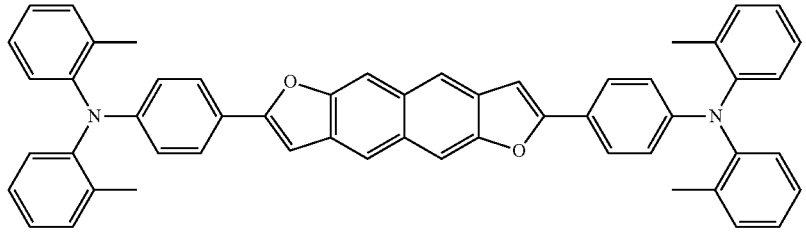
Compound 2-40
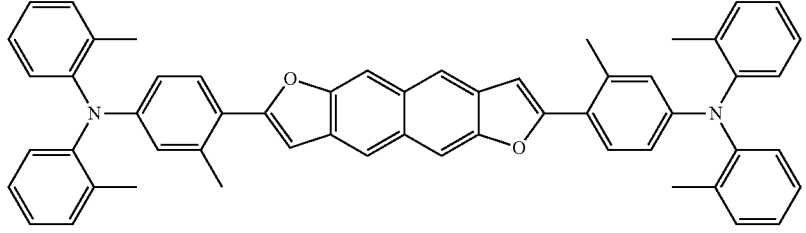

-continued
Compound 2-41
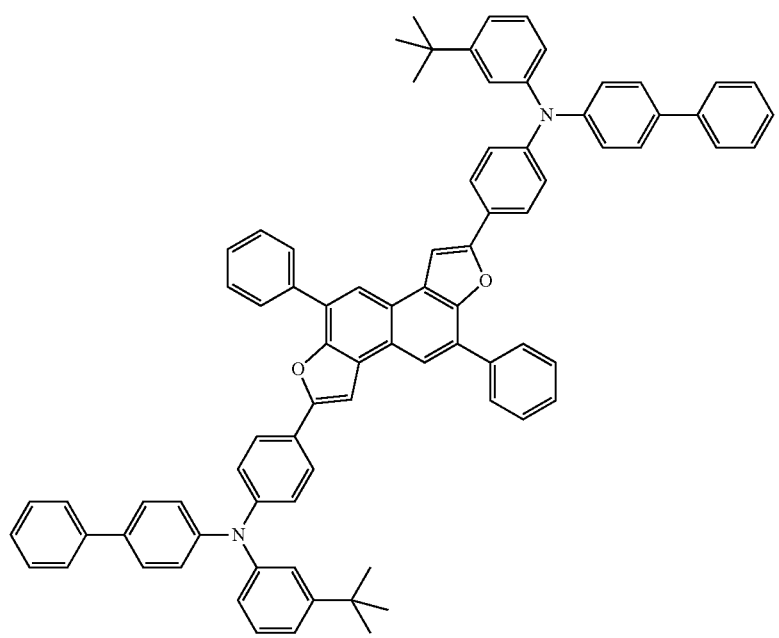
Compound 2-42
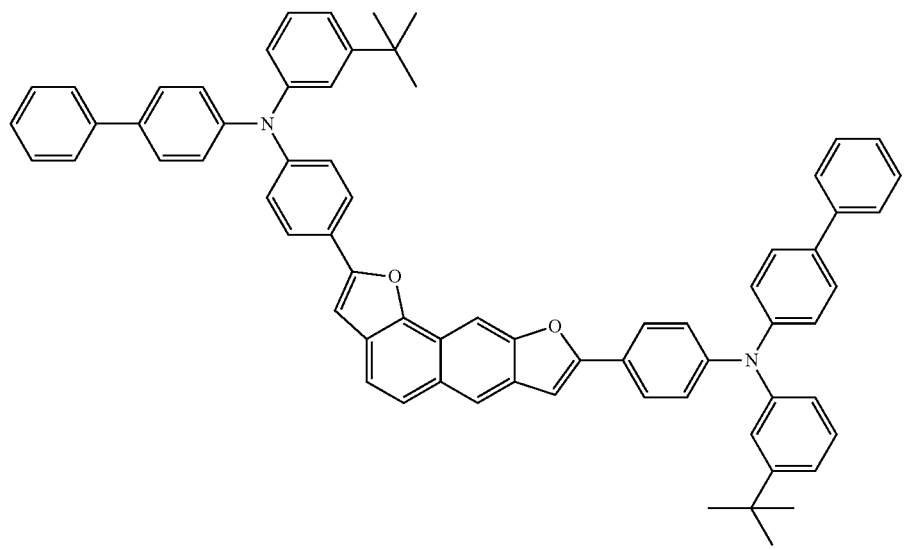
Compound 2-43
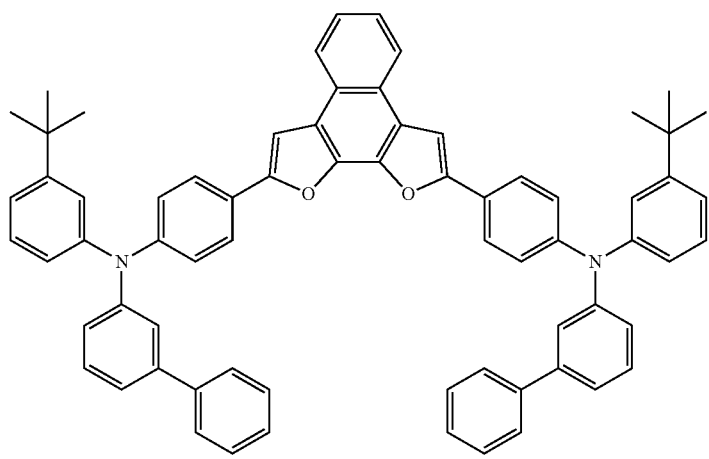

-continued
Compound 2-44
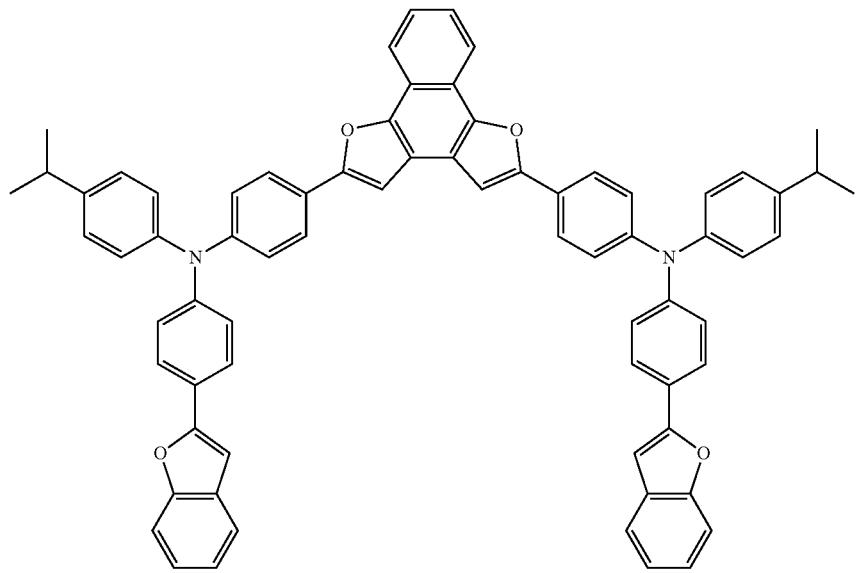
Compound 2-45
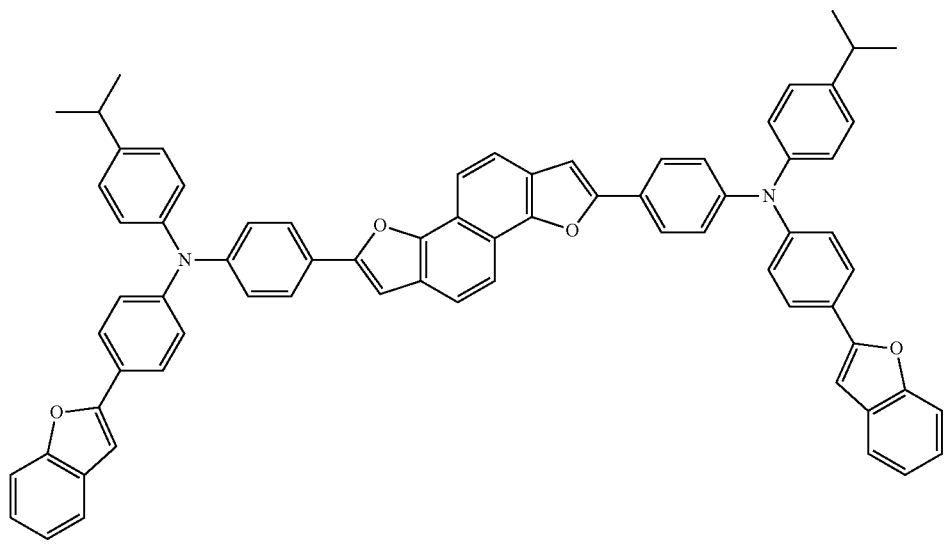
Compound 2-46
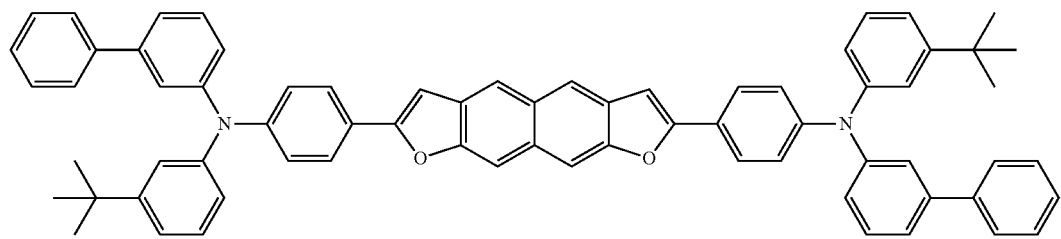

Compound 2-47
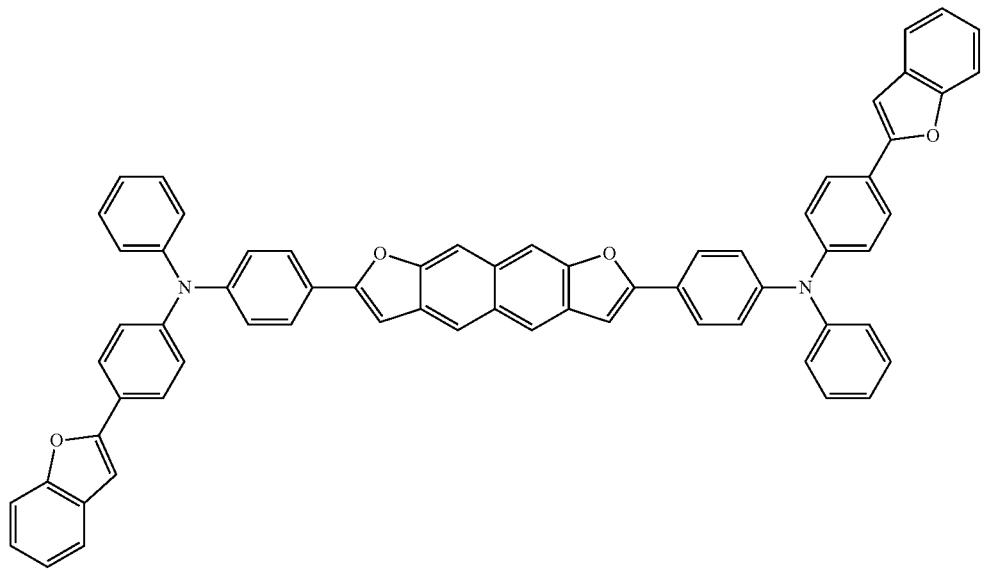
Compound 2-48
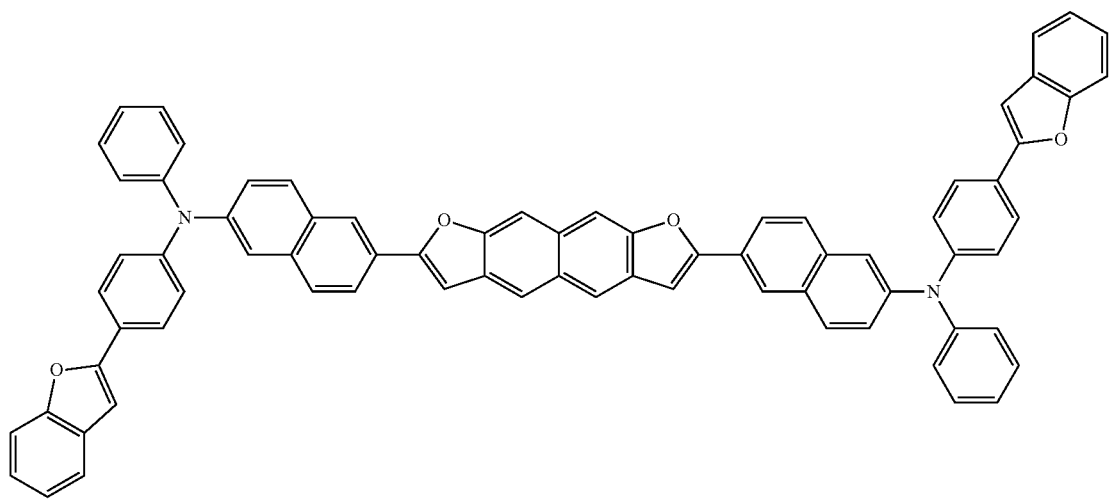
Compound 2-49
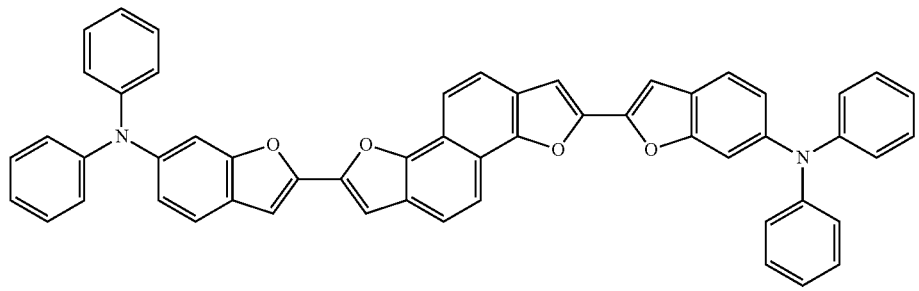

Compound 2-50
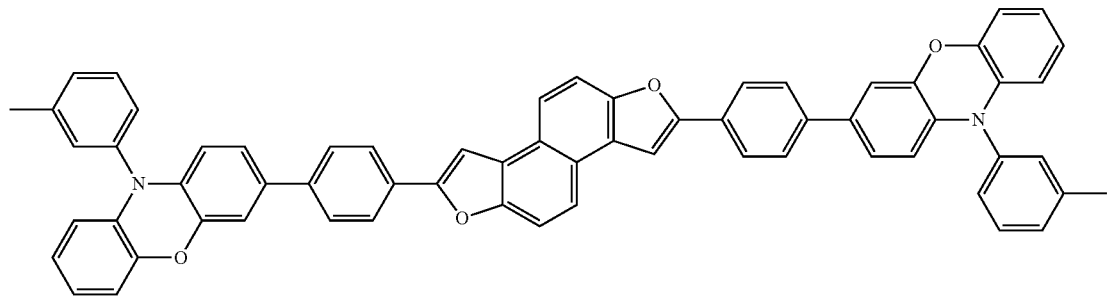
Compound 2-51
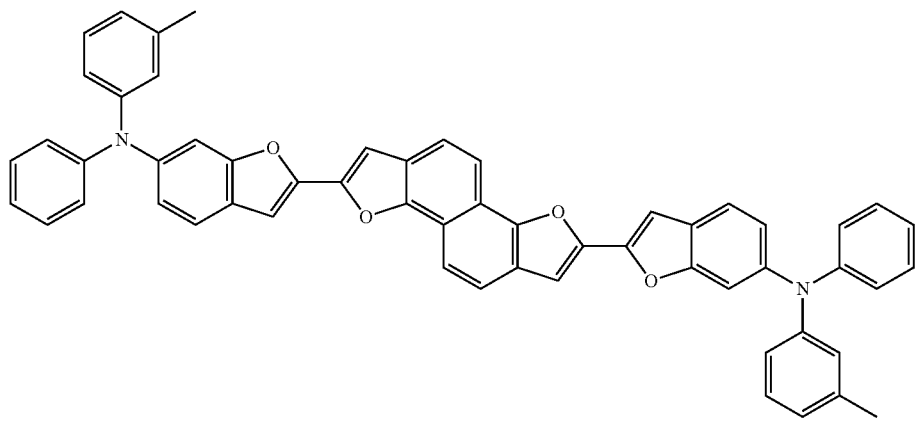
(c) NpHet-3 where Q=O
Compound 3-1
Compound 3-2
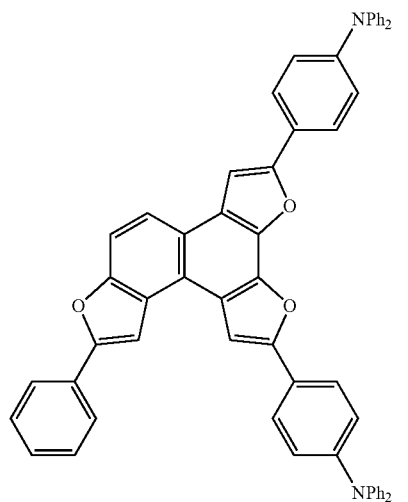

-continued
Compound 3-3
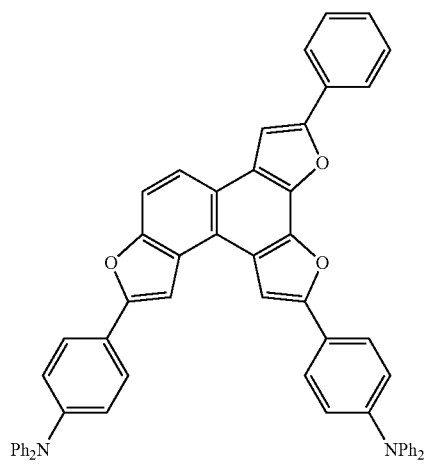
Compound 3-4
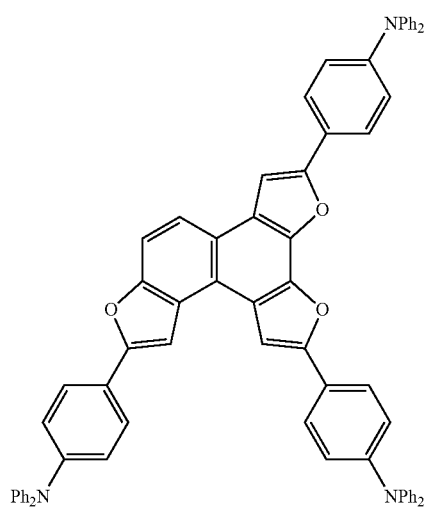
Compound 3-5
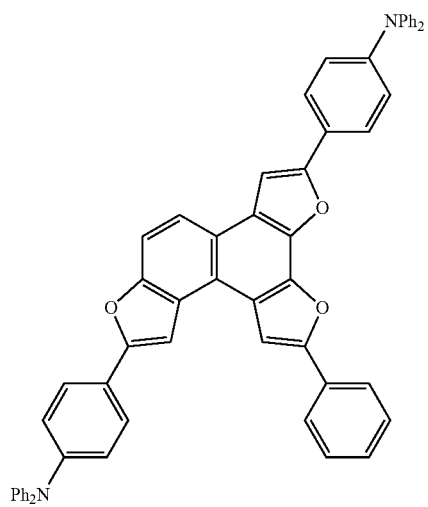
-continued
Compound 3-6
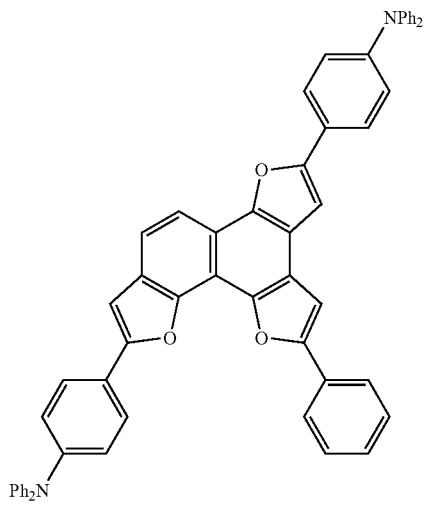
Compound 3-7
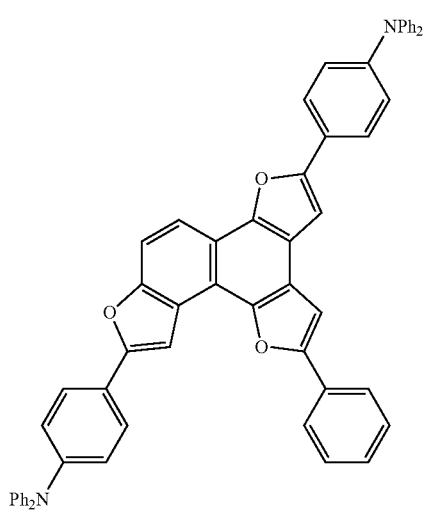
Compound 3-8
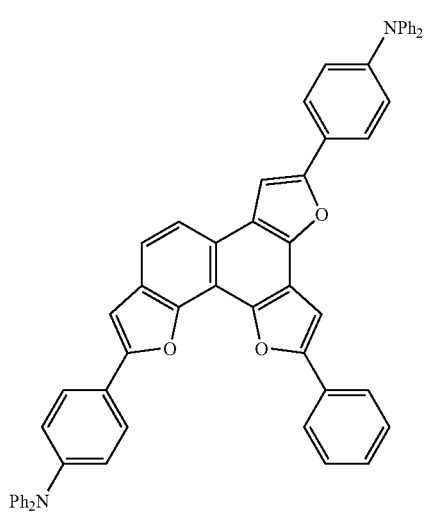

-continued
Compound 3-9
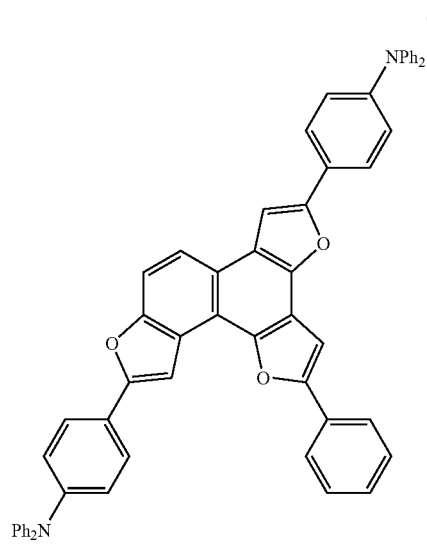
Compound 3-10
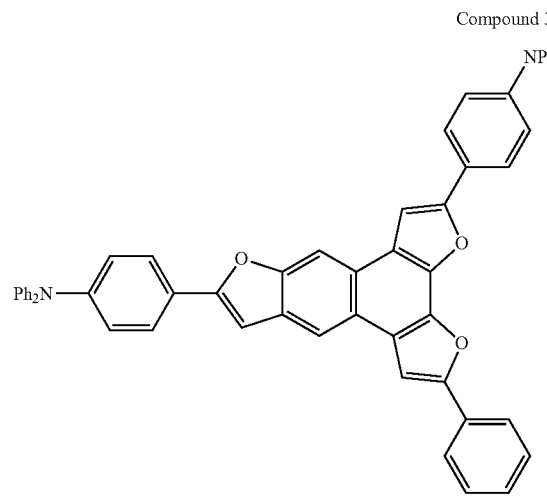
Compound 3-11
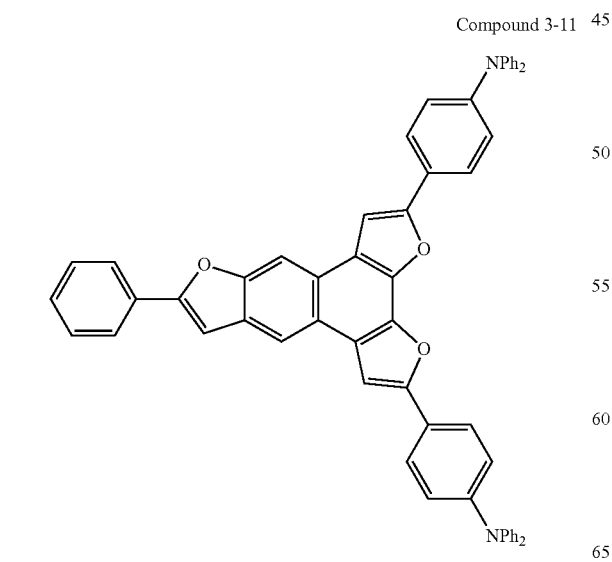
-continued
Compound 3-12
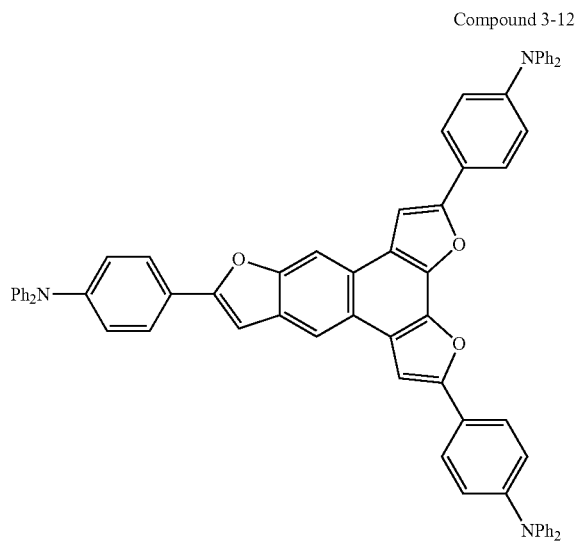
Compound 3-13
Compound 3-14
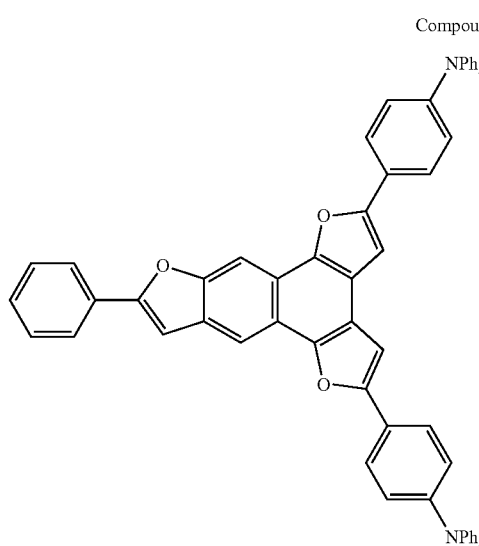

Compound 3-15
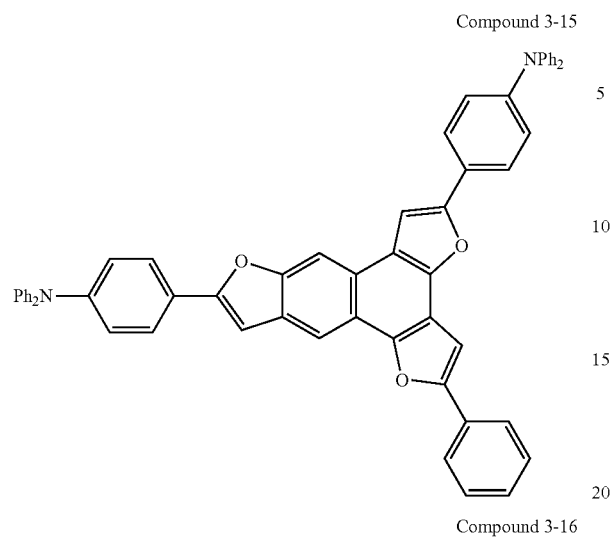
Compound 3-16
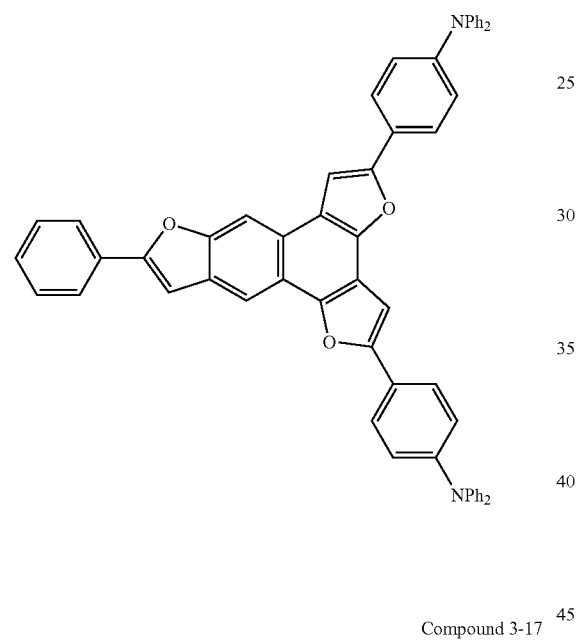
Compound 3-17
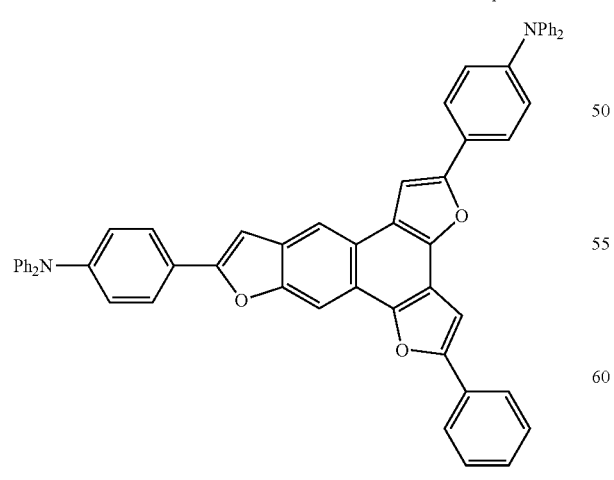
Compound 3-18
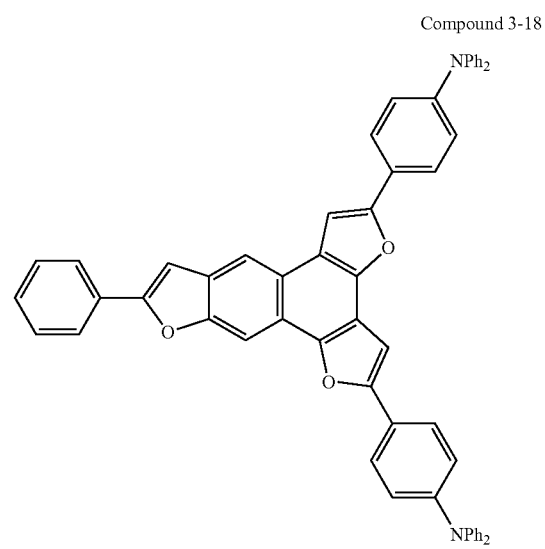
In the above compounds, Ph indicates phenyl.
(d) Compounds having NpHet-4 where Q=O.
Compound 4-1
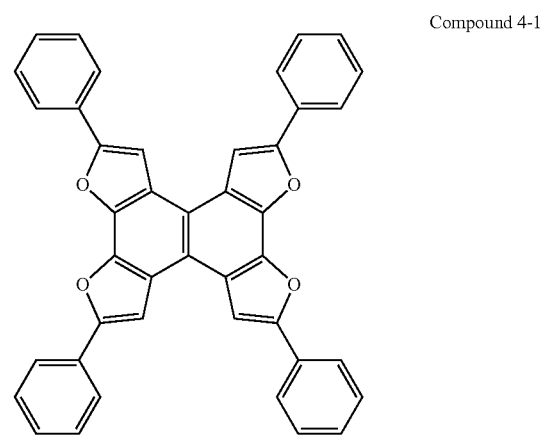
Compound 4-2
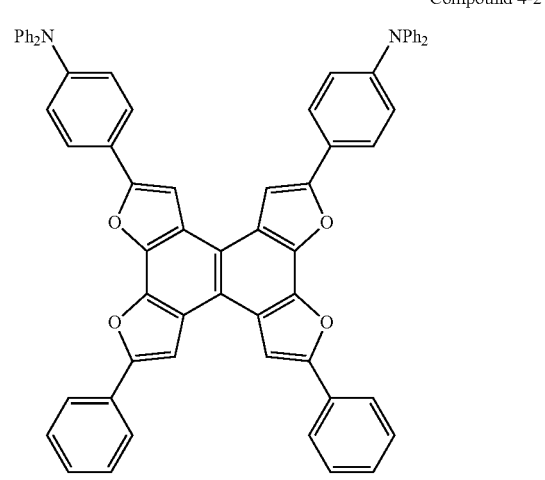

Compound 4-3
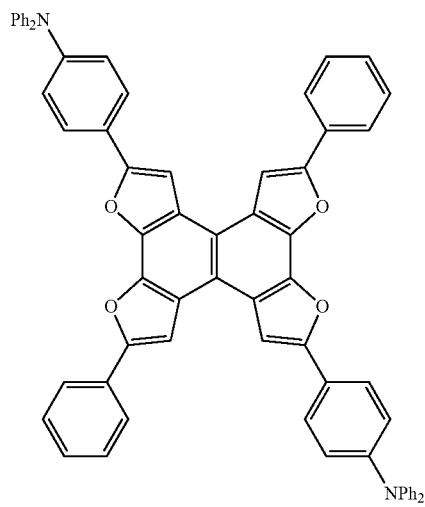
Compound 4-4
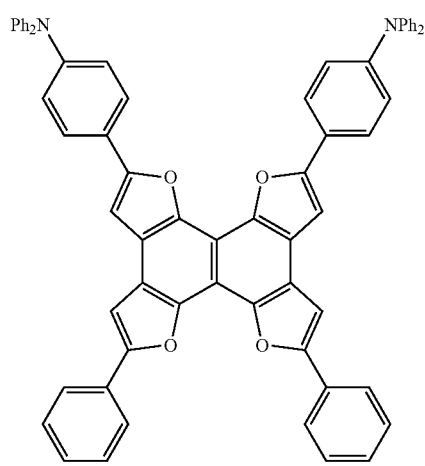
Compound 4-5
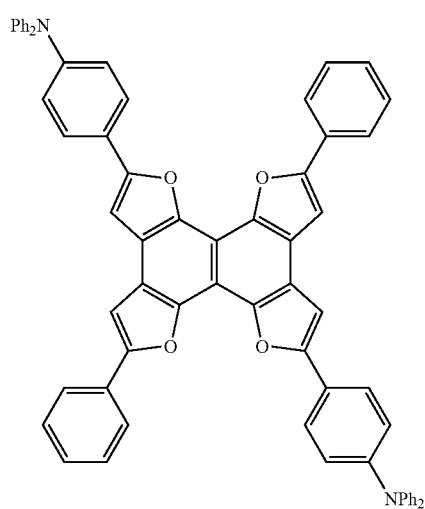
Compound 4-6
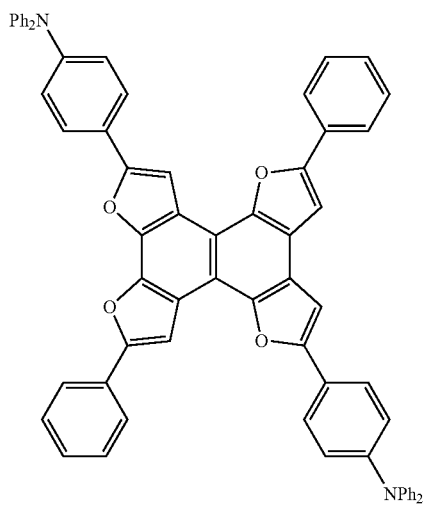
Compound 4-7
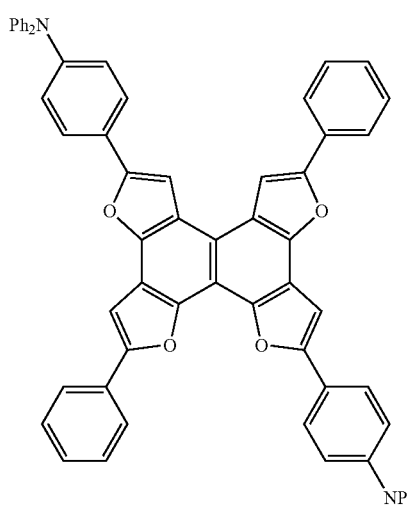
Compound 4-8
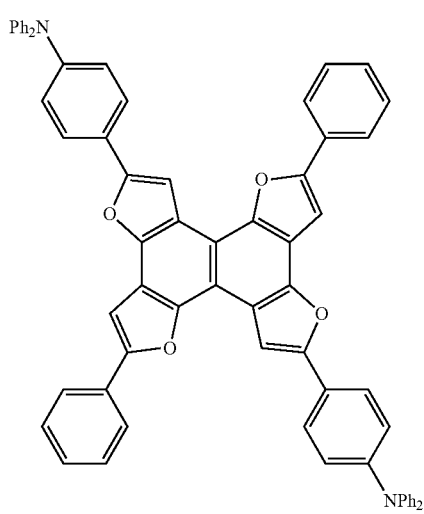

-continued

Compound 4-9

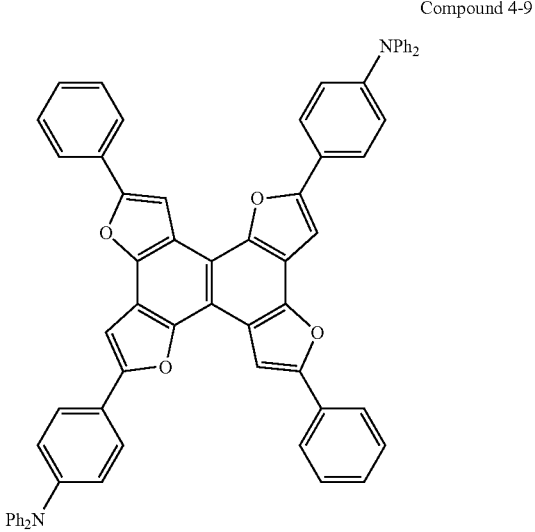

In the above compounds, Ph indicates phenyl.

3. Devices

Organic electronic devices that may benefit from having one or more layers comprising the compounds having Formula I described herein include, but are not limited to: (1) devices that convert electrical energy into radiation (e.g., a light-emitting diode, light emitting diode display, diode laser, or lighting panel); (2) devices that detect a signal using an electronic process (e.g., a photodetector, a photoconductive cell, a photoresistor, a photoswitch, a phototransistor, a phototube, an infrared ("IR") detector, or a biosensors); (3) devices that convert radiation into electrical energy (e.g., a photovoltaic device or solar cell); (4) devices that convert light of one wavelength to light of a longer wavelength, (e.g., a down-converting phosphor device); (5) devices that include one or more electronic components that include one or more organic semiconductor layers (e.g., a transistor or diode); or any combination of devices in items (1) through (5).

In some embodiments, the device includes a photoactive layer having a compound of Formula I. A compound having any of the above-described embodiments of Formula I can be used in the photoactive layer.

In some embodiments, the device includes an anode and a cathode with a photoactive layer therebetween, where the photoactive layer includes a compound having Formula I. A compound having any of the above-described embodiments of Formula I can be used in the photoactive layer.

One illustration of an organic electronic device structure including a compound having Formula I is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. As a further option, devices may have an anti-quenching layer (not shown) between the photoactive layer 140 and the electron transport layer 150.

Layers 120 through 150, and any additional layers between them, are individually and collectively referred to as the active layers.

Figure 2:
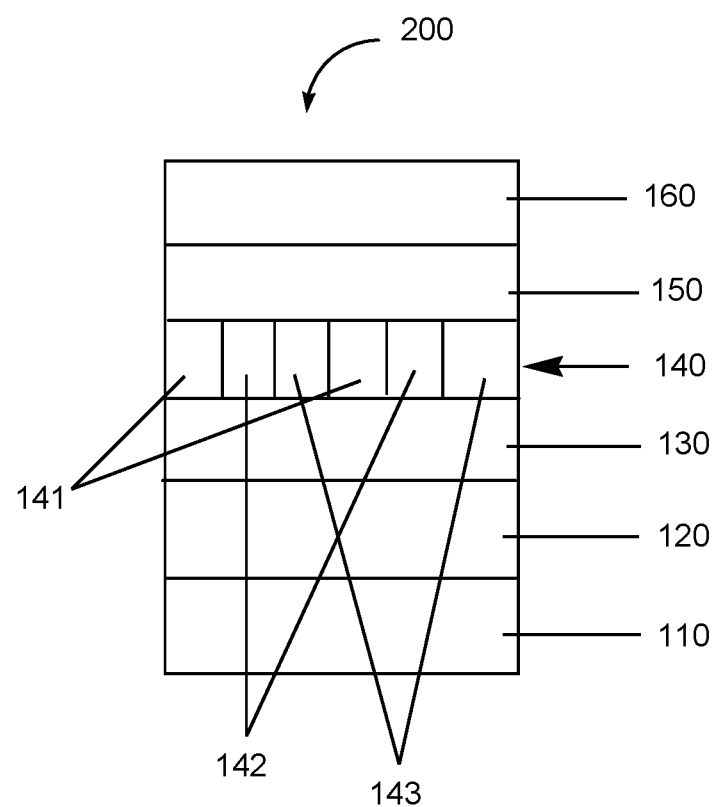
FIG. 2 includes an illustration of another example of an organic electronic device including a new compound described herein.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-2000 Å, in some embodiments, 200-1000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula I are useful as the emissive material in photoactive layer 140, having blue emission color. They can be used alone or as a dopant in a host material.

a. Photoactive Layer

In some embodiments, the photoactive layer includes a host material and a compound having Formula I as a dopant. In some embodiments, a second host material is present.

In some embodiments, the photoactive layer includes only a host material and a compound having Formula I as a dopant. In some embodiments, minor amounts of other materials are present so long as they do not significantly change the function of the layer.

In some embodiments, the photoactive layer includes only a first host material, a second host material, and a compound having Formula I as a dopant. In some embodiments, minor amounts of other materials, are present so long as they do not significantly change the function of the layer.

In some embodiments, the dopant compound has Formula I-a.

In some embodiments, the host material is selected from the group consisting of chrysenes, phenanthrenes, triphenylenes, phenanthrolines, triazines, naphthalenes, anthracenes, quinolines, isoquinolines, quinoxalines, phenylpyridines, carbazoles, indolocarbazoles, indoloindoles, furans, benzofurans, naphthofurans, dibenzofurans, benzodifurans, naphthodifurans, metal quinolinate complexes, substituted derivatives thereof, deuterated analogs thereof, and combinations thereof.

In some embodiments, the host is selected from the group consisting of triphenylenes, carbazoles, indolocarbazoles, indoloindoles, furans, benzofurans, naphthofurans, dibenzofurans, naphthodifurans, substituted derivatives thereof, deuterated analogs thereof, and combinations thereof.

In some embodiments, the host material is a 9,10-diaryl anthracene compound or deuterated analog thereof.

In some embodiments, the host material is a chrysene derivative having one or two diarylamino substituents, or a deuterated analog thereof In some embodiments, the photoactive layer includes a dopant material and a compound having Formula I as a host. In some embodiments, a second host material is present.

In some embodiments, the photoactive layer includes only a dopant material and a compound having Formula I as a host. In some embodiments, minor amounts of other materials are present so long as they do not significantly change the function of the layer.

In some embodiments, the photoactive layer includes only a compound having Formula I as a first host material, a second host material, and dopant. In some embodiments, minor amounts of other materials are present so long as they do not significantly change the function of the layer.

In some embodiments, the host compound has Formula I-b.

In some embodiments, the host compound has Formula I-c.

In some embodiments, the second host material is selected from the group consisting of chrysenes, phenanthrenes, triphenylenes, phenanthrolines, triazines, naphthalenes, anthracenes, quinolines, isoquinolines, quinoxalines, phenylpyridines, carbazoles, indolocarbazoles, indoloindoles, furans, benzofurans, naphthofurans, dibenzofurans, benzofurans, naphthodifurans, metal quinolinate complexes, substituted derivatives thereof, deuterated analogs thereof, and combinations thereof.

In some embodiments, the second host is selected from the group consisting of triphenylenes, carbazoles, indolocarbazoles, indoloindoles, furans, benzofurans, naphthofurans, dibenzofurans, naphthodifurans, substituted derivatives thereof, deuterated analogs thereof, and combinations thereof.

The weight ratio of dopant to total host material is in the range of 1:99 to 70:30; in some embodiments, 5:95 to 25:75; in some embodiments, 10:90 to 20:80.

Any of the compounds of Formula I represented by the embodiments, specific embodiments, specific examples, and combination of embodiments discussed above can be used in the photoactive layer.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also be made of an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 includes hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can include charge transfer compounds, and the like, such as copper phthalocyanine and the tetrathiafulvalene-tetracyanoquinodimethane system (TTF-TCNQ).

In some embodiments, the hole injection layer includes at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (□-NPB), and porphyrinic compounds, such as copper phthalocyanine. In some embodiments, the hole transport layer includes a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further includes a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

In some embodiments, more than one hole transport layer is present (not shown).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato)

aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; fluoranthene derivatives, such as 3-(4-(4-methylstyryl)phenyl-p-tolylamino)fluoranthene; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

In some embodiments, an anti-quenching layer may be present between the photoactive layer and the electron transport layer to prevent quenching of blue luminance by the electron transport layer. To prevent energy transfer quenching, the singlet energy of the anti-quenching material has to be higher than the singlet energy of the blue emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high singlet and triplet energies.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In some embodiments, the liquid medium includes only one or more organic solvents. In some embodiments, minor amounts of other materials are present, so long as they do not substantially affect the liquid medium.

In some embodiments, the liquid medium includes only water or includes only water and an organic solvent. In some embodiments, minor amounts of other materials are present, so long as they do not substantially affect the liquid medium.

The hole injection material is present in the liquid medium in an amount from 0.5 to 10 percent by weight.

In some embodiments, the hole injection layer is formed by any continuous or discontinuous liquid deposition technique. In some embodiments, the hole injection layer is applied by spin coating. In some embodiments, the hole injection layer is applied by ink jet printing. In some embodiments, the hole injection layer is applied by continuous nozzle printing. In some embodiments, the hole injection layer is applied by slot-die coating. After liquid deposition, the liquid medium can be removed in air, in an inert atmosphere, or by vacuum, at room temperature or with heating.

In some embodiments, the hole transport layer is formed by liquid deposition of hole transport material in a liquid medium. The liquid medium is one in which the hole transport material is dissolved or dispersed and from which it will form a film. In some embodiments, the liquid medium includes one or more organic solvents. In some embodiments, the liquid medium includes water or water and an organic solvent. In some embodiments, the organic solvent is an aromatic solvent. In some embodiments, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In some embodiments, the hole transport layer is applied by spin coating. In some embodiments, the hole transport layer is applied by ink jet printing. In some embodiments, the hole transport layer is applied by continuous nozzle printing. In some embodiments, the hole transport layer is applied by slot-die coating. After liquid deposition, the liquid medium can be removed in air, in an inert atmosphere, or by vacuum, at room temperature or with heating.

In some embodiments, the photoactive layer is formed by vapor deposition. Such techniques are well known in the art.

In some embodiments, the photoactive layer is formed by liquid deposition of the photoactive material and one or more host materials in a liquid medium. The liquid medium is one in which the materials of the photoactive layer are dissolved or dispersed and from which it will form a film. In some embodiments, the liquid medium includes one or more organic solvents. In some embodiments, minor amounts of additional materials are present so long as they do not substantially affect the function of the photoactive layer.

Suitable classes of solvents include, but are not limited to, aliphatic hydrocarbons (such as decane and hexadecane), halogenated hydrocarbons (such as methylene chloride, chloroform, chlorobenzene, and perfluoroheptane), aromatic hydrocarbons (such as non-substituted and alkyl- and alkoxy-substituted toluenes and xylenes), aromatic ethers (such as anisole and dibenzyl ether), heteroaromatics (such as pyridine) polar solvents (such as tetrahydropyran ("THP"), dimethylacetamide ("DMAC") and N-methyl pyrrolidone ("NMP")), esters (such as ethylacetate, propylene carbonate, methyl benzoate), alcohols and glycols (such as isopropanol and ethylene glycol), glycol ethers and derivatives (such as propylene glycol methyl ether and propylene glycol methyl ether acetate), and ketones (such as cyclopentanone and diisobutyl ketone).

The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In some embodiments, the photoactive layer is applied by spin coating. In some embodiments, the photoactive layer is applied by ink jet printing. In some embodiments, the photoactive layer is applied by continuous nozzle printing. In some embodiments, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In some embodiments, it is deposited by thermal evaporation under vacuum.

The electron injection layer can be deposited by any vapor deposition method. In some embodiments, it is deposited by thermal evaporation under vacuum.

The cathode can be deposited by any vapor deposition method. In some embodiments, it is deposited by thermal evaporation under vacuum.

EXAMPLES

The concepts described herein will be further described in the following examples, which do not limit the scope of the invention described in the claims.

Synthesis Example 1

This example illustrates the preparation of a compound having Formula I, Compound 2-1

(a) 3,7-dibromonaphthalene-2,6-diol

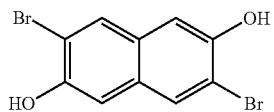

This compound was synthesized as in U.S. Pat. No. 8,816,100.

(b) 2,2'-[(3,7-dibromonaphthalene-2,6-diyl)bis(oxy)]bis(1-phenylethanone)

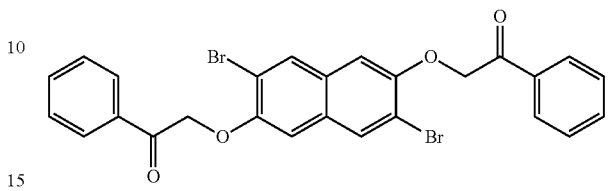

Inside a 500-mL round-bottom flask, 3,7-dibromonaphthalene-2,6-diol (2.75 g, 8.65 mmol) was combined with acetone (250 mL). 2-Bromoacetophenone (3.45 g, 17.3 mmol) and $K_2CO_3$ (4.78 g, 34.6 mmol) were added. The mixture was stirred at 65° C. for 42 h. After cooling to room temperature, the precipitate was filtered and washed with acetone (25 mL) followed by deionized water (50 mL) then diluted HCl (5 v/v %, 50 mL), then water (50 mL) and finally acetone (25 mL). The fluffy solid was dried under reduced pressure to yield an off-white powder (3.5 g, 73%). $^1$H NMR (DMSO-$d_6$, 499.8 MHz) δ 8.11 (s, 2H), 8.05 (d, J=7.7 Hz, 4H), 7.72 (m, 2H), 7.61 (t, J=7.7 Hz, 4H), 7.42 (s, 2H), 5.76 (s, 4H).

(c) 5,10-dibromo-3,8-diphenylnaphtho[2,1-b:6,5-b']difuran

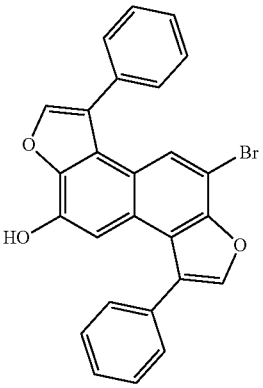 [SMILES: Oc1cc2c(cc(Br)c3occ(-c4ccccc4)c32)c2c(-c3ccccc3)coc12]

Into an oven-dried 500-mL round-bottom flask, 2,2'-[(3,7-dibromonaphthalene-2,6-diyl)bis(oxy)]bis(1-phenylethanone) (2.06 g, 3.72 mmol) was added followed by chloroform (150 mL). The mixture was heated to reflux at 78° C. The suspension was off-white milky. Methane sulfonic acid (2.745 g, 28.6 mmol) was added. The reaction mixture was stirred at 78° C. for 16 h. Then it was allowed to cool to room temperature. The reaction suspension was concentrated under reduced pressure. The product was purified by flash silica chromatography followed by recrystallization in hexanes to afford a colorless powder (0.400 g, 21%). $^1$H NMR (CD$_2$Cl$_2$, 499.8 MHz) δ 8.10 (m, 2H), 7.83 (s, 2H), 7.64-7.56 (m, 10H) UPLC-MS APCI$^+$ (m/z) Calcd for $C_{26}H_{14}Br_2O_2$ ([M+H]$^+$) 516.94. Found 516.93. X-ray crystallographic analysis:

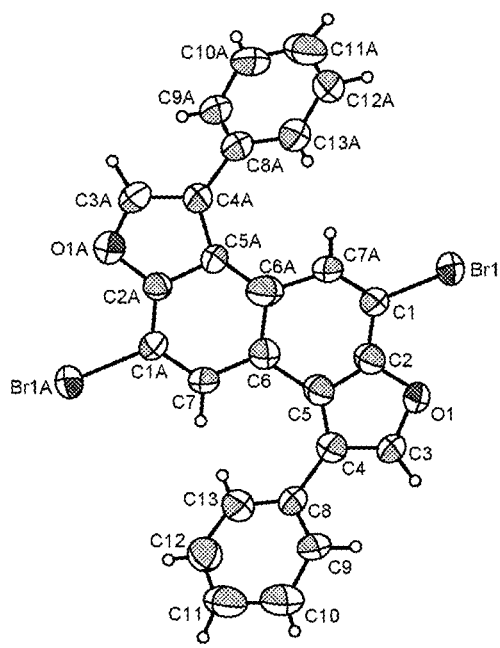

(d) $N^5,N^5,N^{10},N^{10}$-tetra([1,1'-biphenyl]-4-yl)-3,8-diphenylnaphtho[2,1-b:6,5-b']difuran-5,10-diamine, Compound 2-1

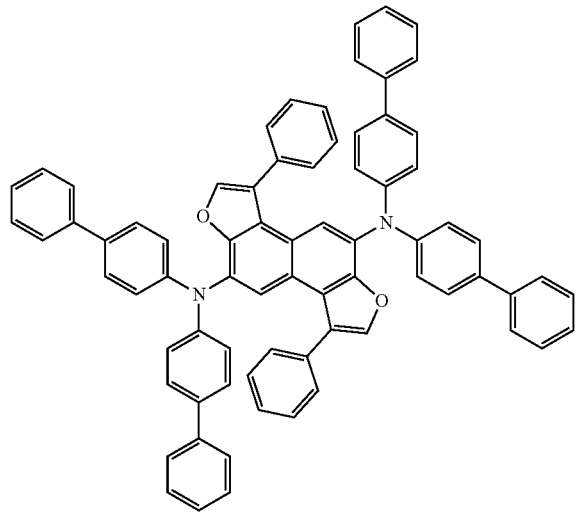 [SMILES: c1ccc(-c2ccc(N(c3ccc(-c4ccccc4)cc3)c3cc4c(cc(N(c5ccc(-c6ccccc6)cc5)c5ccc(-c6ccccc6)cc5)c5occ(-c6ccccc6)c54)c4c(-c5ccccc5)coc34)cc2)cc1]

Into a 50-mL round-bottom flask was added 5,10-dibromo-3,8-diphenylnaphtho[2,1-b:6,5-b']difuran (0.2 g, 0.4 mmol). N-(biphenyl-4-yl)biphenyl-4-amine (0.2 g, 0.6 mmol) and sodium tert-butoxide (0.083 g, 0.86 mmol). Toluene (35 mL) was then added, and the mixture was sparged with $N_2$ for 20 minutes. Inside the glovebox, $Pd_2$(DBA)$_3$ (0.026 g, 0.028 mmol) and tri-tert-butyl-phosphine (0.014 g, 0.069 mmol) were mixed with toluene (10 mL) in a sealed 25-mL flask and stirred for 10 minutes. The catalyst mixture was then transferred to the reaction flask via cannula, and the reaction mixture was stirred at 120° C. for 16 h. The reaction mixture was allowed to cool to room temperature and then diluted with dichloromethane (20 mL). The mixture was then passed through a plug of silica and Celite®. The product was purified by flash silica chromatography followed by recrystallization in hexanes to afford a yellow solid (0.08 g, 21%). UPLC-MS APCI$^+$ (m/z) Calcd for $C_{74}H_{50}N_2O_2$ ([M+H]$^+$) 999.39. Found 999.29.

Synthesis Example 2

This example illustrates the preparation of a compound having Formula I, Compound 2-2.

(a) 4'-propyl-N-(p-tolyl)[1,1'-biphenyl]-4-amine

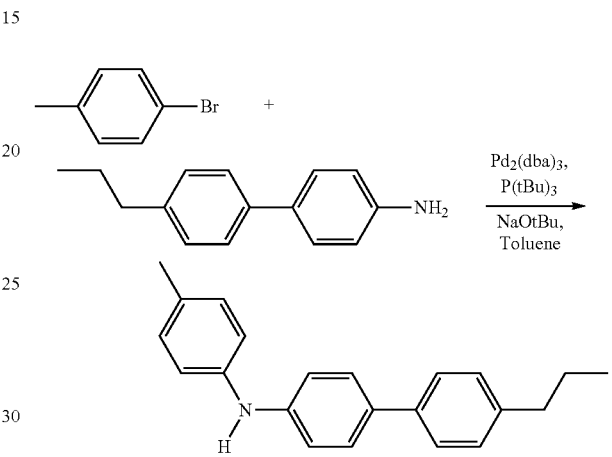

In drybox, 4-bromotoluene (3.34 g, 19.12 mmol), 4'-propyl-[1,1'-biphenyl]-4-amine (4.04 g, 19.12 mmol), $Pd_2$(DBA)$_3$ (175 mg, 0.19 mmol) and anhydrous toluene (110 ml) were taken in a 250 mL flask and stirred for 5 min. NaOtBu (2.39 g, 24.86 mmol) was added in small portions. The reaction was allowed to stir at 50° C. for 16 hours and the progress was monitored by UPLC analysis. After which the mixture was passed through a plug with Celite and basic Alumina eluted with toluene. The solvent was removed and the material was separated on a Silica gel column eluted with chloroform/hexane gradient. Fractions were identified by UPLC analysis, collected, and the solvent was removed by rotary evaporation. The precipitate formed during the stripping off the solvent. It was collected by filtration and dried under vacuum overnight to give the product as white flakes, yield, 4.6 g in 99% purity by UPLC analysis.

(b) 3,8-diphenyl-$N^5,N^{10}$-bis(4'-propyl-[1,1'-biphenyl]-4-yl)-$N^5,N^{10}$-di-p-tolylnaphtho[2,1-b:6,5-b']difuran-5,10-diamine

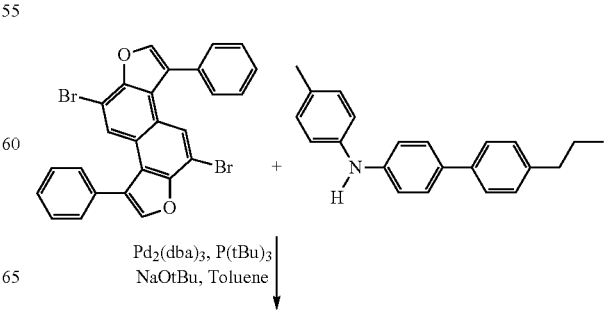

-continued

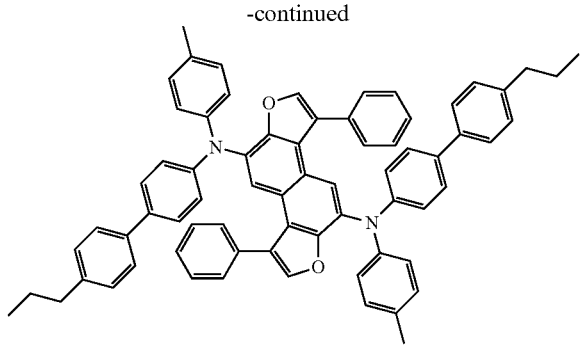

In drybox, 5,10-dibromo-3,8-diphenylnaphtho[2,1-b:6,5-b']difuran (2.10 mg, 0.41 mmol), 4'-propyl-N-(p-tolyl)-[1,1'-biphenyl]-4-amine (256 mg, 0.85 mmol), $Pd_2(DBA)_3$ (11 mg, 0.01 mmol) and anhydrous toluene (20 ml) were taken in a 50 mL flask and stirred for 5 min. NaOtBu (93 mg, 0.97 mmol) was added in small portions. The reaction was allowed to stir at 50° C. for 2 hours and the progress was monitored by UPLC analysis. After which the mixture was passed through a plug with Celite and Silica gel eluted with toluene. The solvent was removed and the residue was dissolved in a small volume of DCM. The solution was added dropwise to MeOH with stirring. After setting at ambient temperature under nitrogen overnight, the precipitate was collected by filtration. The product was separated by flush chromatography, eluted with chloroform/hexane gradient. Product containing fractions were identified by UPLC analysis and combined. The solvent was removed and the residue was re-dissolved in a small volume of DCM (5 mL). The product was precipitated from acetonitrile (50 mL), filtered off and dried under vacuum overnight to give 270 mg of pale yellow amorphous material in 99.9% purity. The structure of the product was confirmed by NMR and LC/MS analysis.

Synthesis Example 3

This example illustrates the preparation of a compound having Formula I, Compound 2-3.

(a) 1,6-dibromonaphtho[1,2-b:5,6-b']difuran

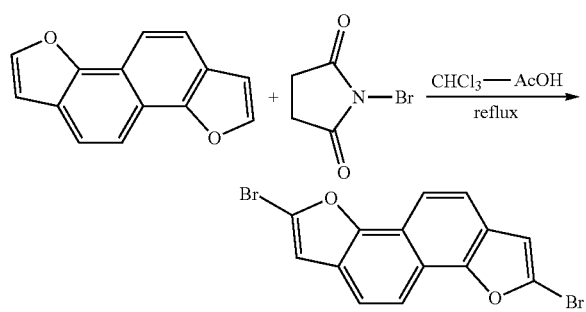

Into a RBF (250 mL) was added naphtho[1,2-b:5,6-b']difuran (3.0 g, 14.4 mmole), chloroform (100 mL) and acetic acid (20 mL) and N-bromosuccinimide was added in one portion (5.38 g, 30.2 mmole). The reaction was stirred and heated to gentle refluxing stirring for 1 hour. First, a clear solution was formed, then a light yellow precipitate came out. UPLC analysis indicated that the reaction was completed.

After cooling down to RT, water was added. The organic phase was separated, washed with water, saturated brine and dried with $MgSO_4$. After which, the solution was passed through a Silica gel plug. The solvent was evaporated and the residue was crystallized from chloroform/hexane to give the product as light yellow powder, 3.1 g in 99% purity by UPLC analysis. The structure of the product was confirmed by NMR and LC/MS analysis.

(b) 2,7-bis(4-butylphenyl)naphtho[1,2-b:5,6-b']difuran

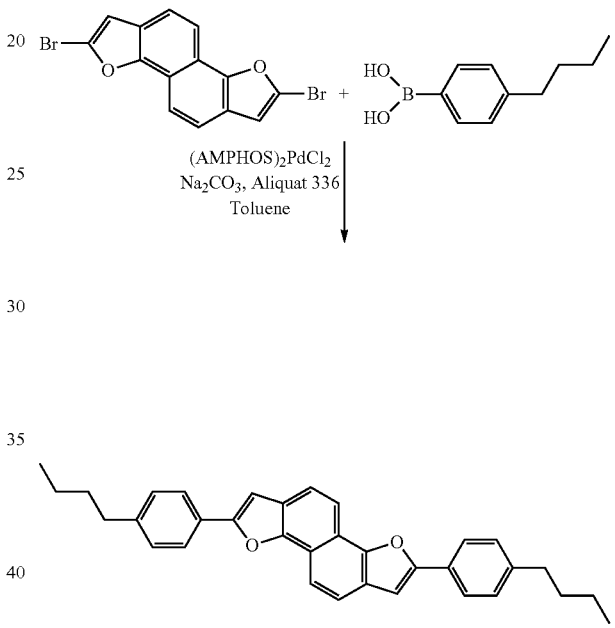

To a 250 mL mL three-necked round bottom flask were added 2,7-dibromonaphtho[1,2-b:5,6-b']difuran (3.00 g, 7.95 mmol), (4-butylphenyl)boronic acid (3.00 g, 16.70 mmol), toluene (165 ml), aqueous sodium carbonate (2 M, 16 mL) and Aliquat 336 (32 mg). With stirring, the system was purged with nitrogen for 20 min. $(AMPHOS)_2PdCl_2$ (28 mg, 0.04 mmol), was added and the system was purged for another 10 min. The reaction was stirred and gently refluxed under nitrogen for 4 hours and the progress was monitored by UPLC analysis. After which, the organic phase was separated, washed with aq. HCl, saturated brine and dried with magnesium sulfate. The solution was passed through a short column of Alumina (basic) eluted with toluene. The volume of the solution was reduced and acetonitrile was added. The mixture was allowed to stand at RT overnight. The product was filtered, washed with acetonitrile and dried under vacuum to give 3.1 g product as a light yellow crystalline material in 98% purity by UPLC analysis. The structure of the product was confirmed by NMR and LC/MS analysis.

(c) 1,6-dibromo-2,7-bis(4-butylphenyl)naphtho[1,2-b:5,6-b']difuran

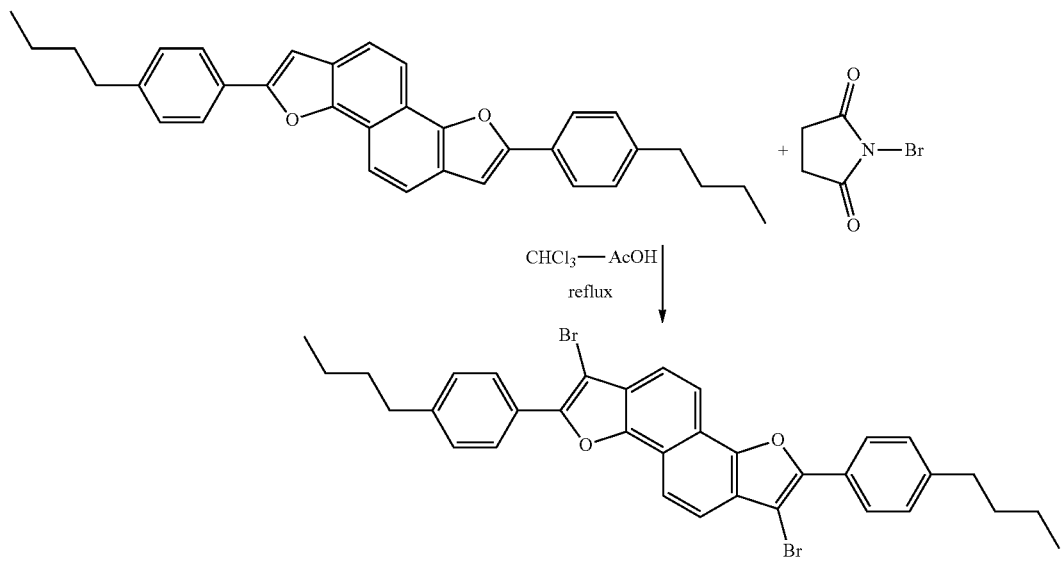

Into a RBF (250 mL) was added 2,7-bis(4-butylphenyl)naphtho[1,2-b:5,6-b']difuran (2.1 g, 4.44 mmole), chloroform (100 mL), acetic acid (20 mL) and N-bromosuccinimide (1.66 g, 9.33 mmol). The reaction was stirred and heated to gentle refluxing stirring for 1 hour. First, a clear solution was formed. Then a light yellow precipitate came out. UPLC analysis indicated that the reaction was completed.

After cooling, water was added and the organic phase was separated. The solution washed with water, saturated brine and dried with $MgSO_4$ before being passed through a Silica gel plug. The solvent was evaporated and the residue was crystallized from chloroform/hexane to give 1.7 g light yellow powder in 94% purity by UPLC analysis. The structure of the product was confirmed by NMR and LC/MS analysis.

(d) 2,7-bis(4-butylphenyl)-$N^1$,$N^6$-bis(4'-propyl-[1,1'-biphenyl]-4-yl)-$N^1$,$N^6$-di-p-tolylnaphtho[1,2-b:5,6-b']difuran-1,6-diamine, Compound 3

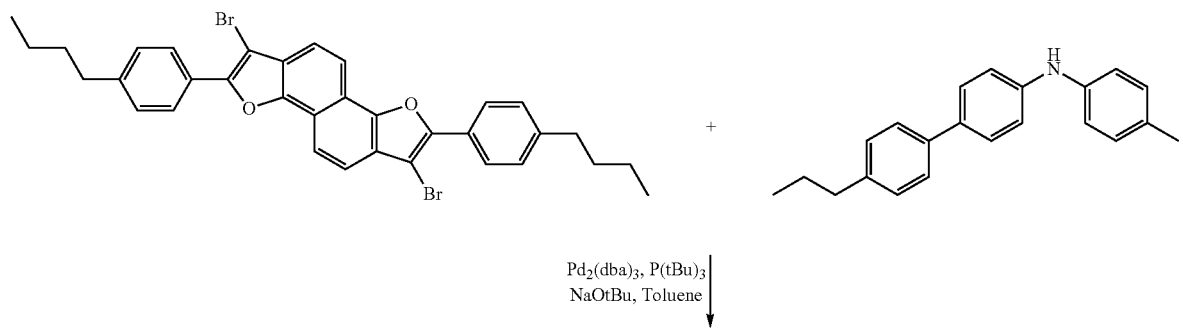

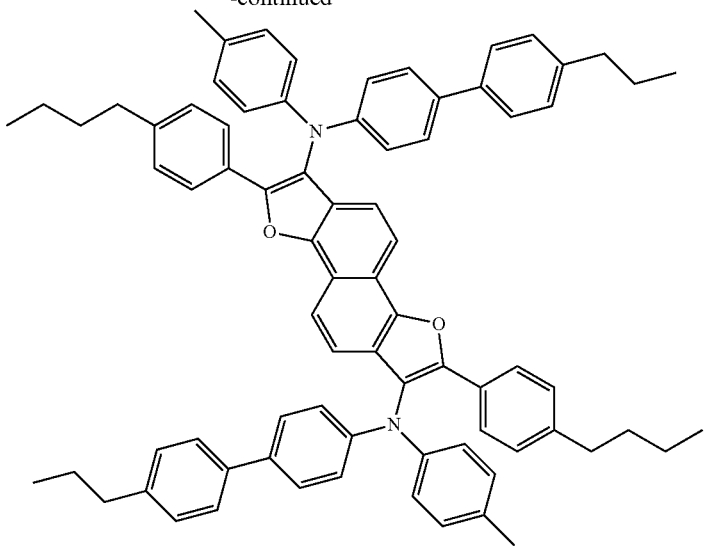

In drybox, 1,6-dibromo-2,7-bis(4-butylphenyl)naphtho[1,2-b:5,6-b']difuran (387 mg, 0.61 mmol), 4'-propyl-N-(p-tolyl)-[1,1'-biphenyl]-4-amine (379 mg, 1.26 mmol), Pd$_2$(DBA)$_3$ (17 mg, 0.02 mmol) and anhydrous toluene (33 ml) were taken in a 100 mL flask and stirred for 5 min. NaOtBu (141 mg, 1.46 mmol) was added in small portions. The reaction was allowed to stir at 50° C. for 2 hours and the progress was monitored by UPLC analysis. After which the mixture was passed through a plug with Celite and Silica gel eluted with toluene. The solvent was removed and the residue was dissolved in a small volume of DCM. The solution was added dropwise to MeOH with stirring. After setting at ambient temperature under nitrogen overnight, the precipitate was collected by filtration. The product was separated by flush chromatography, eluted with chloroform/hexane gradient. Product containing fractions were identified by UPLC analysis and combined. The solvent was removed and the residue was re-dissolved in a small volume of DCM (5 mL). The product was precipitated from acetonitrile (50 mL), filtered off and dried under vacuum overnight to give 275 mg of pale yellow amorphous material in 99.9% purity. The structure of the product was confirmed by NMR and LC/MS analysis.

Synthesis Example 4

This example illustrates the preparation of a compound having Formula I, Compound 2-4.

(a) 2,7-dibromo-3,8-diphenylnaphtho[2,1-b:6,5-b']difuran

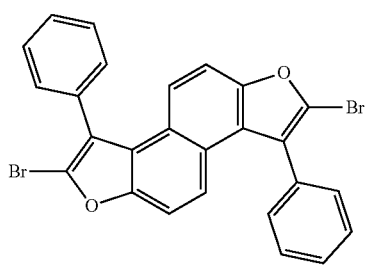 [SMILES: Brc1oc2ccc3c(ccc4oc(Br)c(-c5ccccc5)c43)c2c1-c1ccccc1]

This compound was synthesized as in U.S. Pat. No. 8,247,810.

(b) 4,4'-(3,8-Diphenylnaphtho[2,1-b:6,5-b']difuran-2,7-diyl)bis(N,N-diphenylaniline), Compound 4

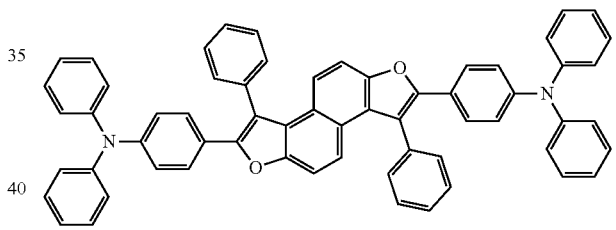

Into a 100-mL 2-neck round-bottom flask containing a stir bar were added 2,7-dibromo-3,8-diphenylnaphtho[2,1-b:6,5-b']difuran (0.50 g, 0.96 mmol), [4(diphenylamino)phenyl]boronic acid (0.58 g, 2.03 mmol) and potassium phosphate tribasic monohydrate (1.18 g, 5.02 mmol). Toluene (5 mL) and ethanol (5 mL) were added. The mixture was sparged with nitrogen for 20 min. Inside a glovebox, tetrakis(triphenylphosphine)palladium (0.120 g, 0.104 mmol) was added to a 50-mL flask followed by toluene (15 mL). The flask was sealed with a rubber septum, and brought out of the glovebox. The catalyst solution was transferred to the reaction flask via a cannula. The reaction mixture was stirred at 115° C. for 20 h. The crude product was purified by flash silica chromatography to yield a yellow powder (0.080 g, 10%) $^1$H NMR (CD$_2$Cl$_2$, 499.8 MHz) δ 7.64-7.55 (m, 6H), 7.47 (s, 1H), 7.40 (m, 2H), 7.29-7.25 (m, 4H), 7.10-7.03 (m, 6H), 6.90 (m, 2H). UPLC-MS APCI$^+$ (m/z) Calcd for C$_{62}$H$_{42}$N$_2$O$_2$ ([M+H]$^+$) 847.33. Found 847.15.

Synthesis Example 5

This example illustrates the preparation of a compound having Formula I, Compound 1-1.

Step a.

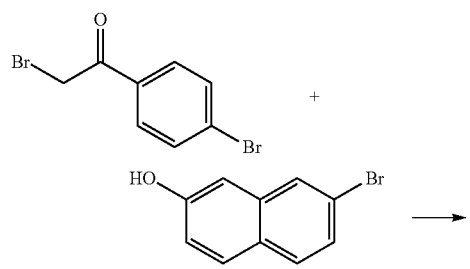

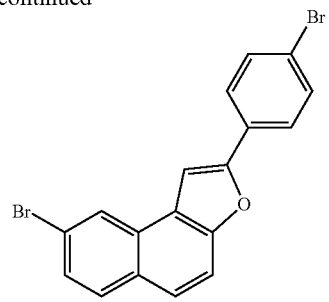

4.42 g bromonaphthol was dissolved into 100 mL toluene and to this was added 8.0 g dibromoacetophenone. 13 g basic alumina was added and the mixture was refluxed for 16 h under air. The slightly orange clear solution generated a white solid overnight which densified on cooling. The hot toluene solution was filtered to remove alumina and a white solid was collected with cooling.

Step b.

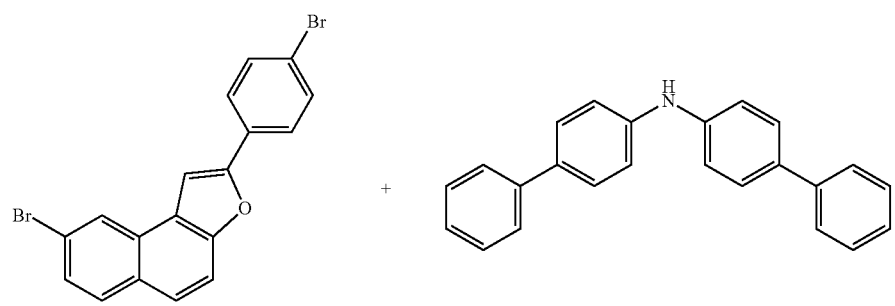

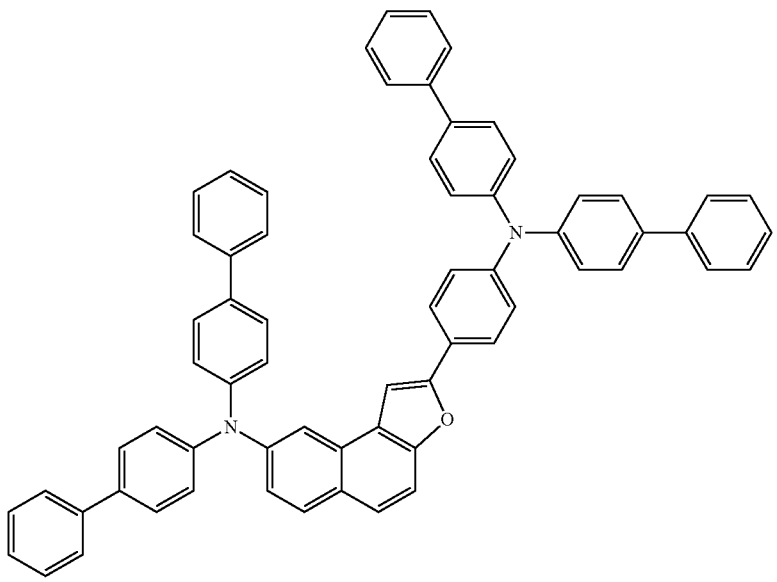

1.0 g of the material from Step a was reacted with 1.6 g bis-diphenylamine using amination conditions (0.2 g Pd$_2$(DBA)$_3$, 0.09 g P(t-Bu)$_3$ and 0.5 g t-BuONa) and dissolved into 50 mL toluene. Upon addition of catalyst materials, the solution was dark purple. The mixture was heated at 95 C under nitrogen for 2 hrs. The solution became dark with a grey opalescent precipitate after 3 hrs. The solution was evaporated to dryness and then extracted through a bed of alumina using methylene chloride in soxhlet. This generated an orange solution which precipitated a pale yellow solid with bright blue photoluminescence. The solid was recrystallized from hot toluene (~0.45 g in ~50 mL boiling toluene). A flocculent solid was slowly generated as the solution cooled.

Synthesis Example 6

This example illustrates the preparation of a compound having Formula I, Compound 1-2.

Step a. Intermediate INT-1

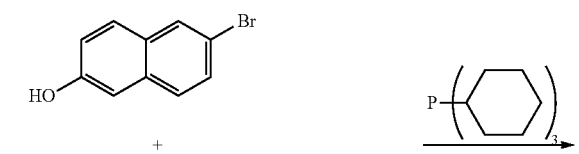

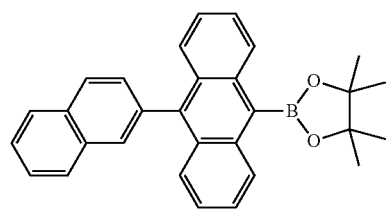

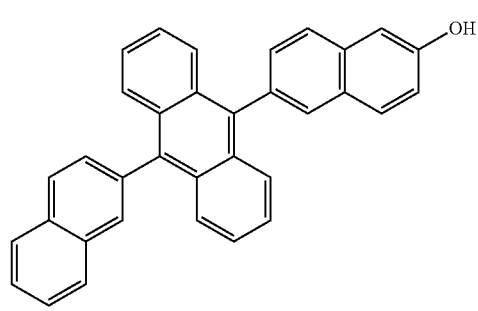

INT-1

In a glove box, 1.2 g 2-bromo-6-naphthol was added to 2.15 g of anthracene boronic ester. To this was added 0.12 g Pd$_2$(DBA)$_3$, 0.07 g tricyclohexylphosphine and 1.9 g potassium phosphate and all was dissolved into 60 mL 1,4-dioxane and 30 mL water. This was mixed and heated in glove box in mantle at 75° C. under nitrogen over 16 hrs. At end of heating time the solution was clear dark reddish. The solution was evaporated and the solid extracted with acetone/DCM multiple times to collect orange red solution which on evaporation precipitated a grey yellow solid in ~1.0 g yield.

Step b. Compound 1-2

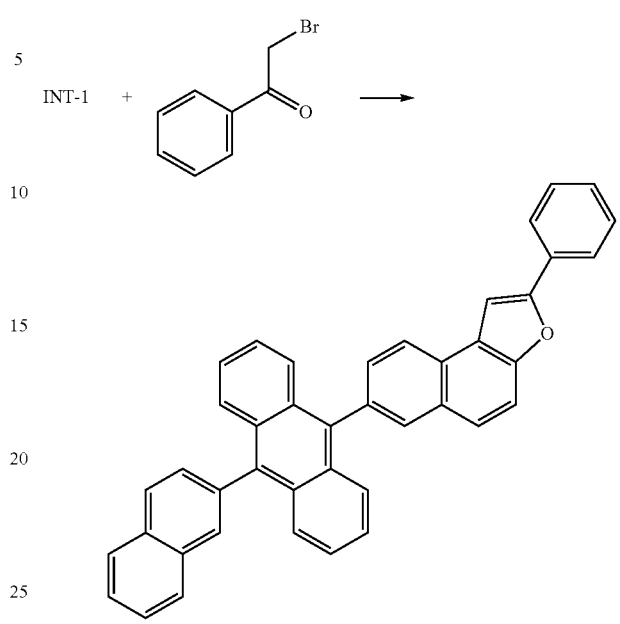

1 g of INT-1 from Step a and 0.4 g of bromoacetophenone in 50 mL toluene with 2.5 g basic alumina was refluxed overnight in air. On cooling there was ppt. suspended above the alumina. The lighter ppt was decanted from the alumina and filtered to collect the solid. This was recrystallized from boiling toluene, filtered and cooled to collect pale yellow flocculent crystals. These were washed with acetonitrile, methanol and suctioned dry to ~0.55 g.

Synthesis Example 7

This example illustrates the preparation of a compound having Formula I, Compound 2-14.

(a) N-([1,1'-biphenyl]-4-yl)-6-bromo-N-(4-(tert-butyl)phenyl) naphthalene-2-amine

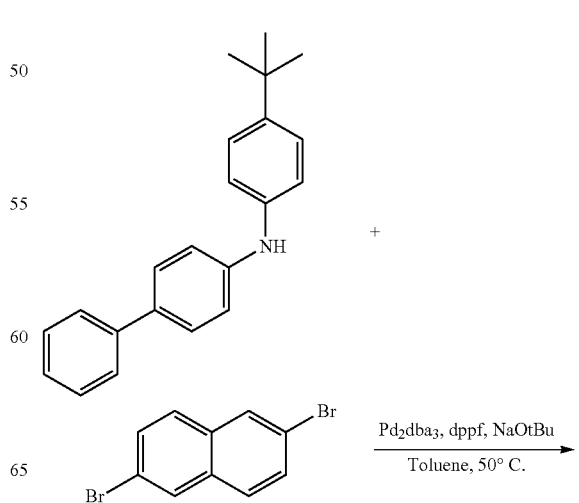

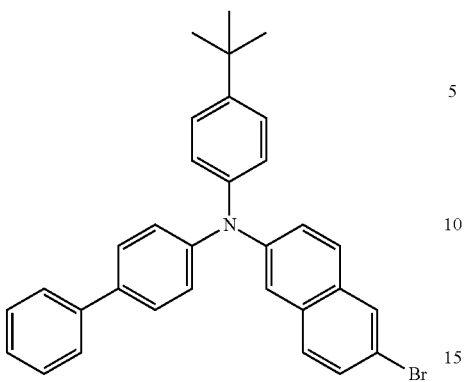

In the glovebox, Pd₂(DBA)₃ (0.14 g, 0.15 mmol), 1,1'-ferrocenediyl-bis(diphenylphosphine) (0.085 g, 0.15 mmol) and anhydrous toluene (10 mL) were added to a 100-mL round-bottom flask. The mixture was stirred for 10 minutes. The catalyst mixture was diluted with anhydrous toluene (40 mL), followed by the addition of 2,6-dibromonaphthalene (2.82 g, 9.86 mmol), N-(4-(tert-butyl)phenyl)-[1,1'-biphenyl]-4-amine (2.3 g, 7.63 mmol) and NaOtBu (2.30 g, 23.9 mmol). The flask was sealed with rubber septa and heated at 55° C. for 19 h, then at 70° C. for 3 h and then 80° C. for 1 h. The reaction mixture was purified by flash column chromatography to give a colorless solid (2.50 g, 65%). UPLC-MS APCI⁺ (m/z) Calcd for C₃₂H₂₈BrN ([M+H]⁺) 506.15. Found 506.00, 508.01.

(b) N-([1,1'-biphenyl]-4-yl)-N-(4-(tert-butyl)phenyl)-6-(4,4,5,5-tetramethyl-1,3,2-dioxaborolan-2-yl)naphthalen-2-amine

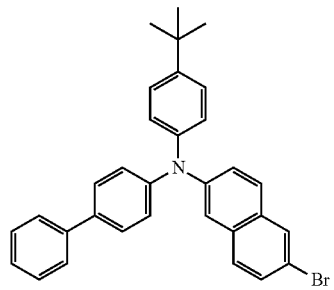

Exact Mass: 505.14
Molecular Weight: 506.49

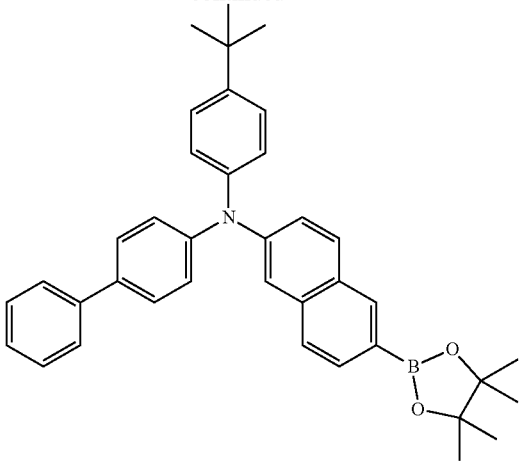

Exact Mass: 553.32
Molecular Weight: 553.55

N-([1,1'-biphenyl]-4-yl)-6-bromo-N-(4-(tert-butyl)phenyl)naphthalen-2-amine (2.5 g, 4.9 mmol), B₂pin₂ (1.90 g, 7.40 mmol), potassium acetate (1.46 g, 14.8 mmol) and Pd(ddpf)Cl₂—CH₂Cl₂ adduct (0.201 g, 0.246 mmol) were added to a 100-mL 2-neck round-bottom flask, which was then fitted with a reflux condenser attached to a manifold, and a septum was placed over the side tubing adapter. Then 3 cycles of vacuum and nitrogen venting were performed. Anhydrous 1,4-dioxane (24 mL) was transferred to the reaction flask via syringe. The mixture was sparged with nitrogen for 20 minutes. The reaction mixture was stirred at 110° C. for 3 h. After cooling to room temperature, the reaction mixture was passed through a plug of Celite® 60 g. The filtrate was concentrated to a dark brown oil (4.7 g). The oil was purified by flash column chromatography to yield a colorless solid (2.1 g, 78%). ¹H NMR (CD₂Cl₂, 499.8 MHz) δ 8.22 (s, 1H), 7.76 (d, J=8.8 Hz, 1H), 7.68 (d, J=8.2 Hz, 1H), 7.60 (d, J=7.4 Hz, 2H), 7.57-7.51 (m, 3H), 7.43 (t, J=7.7 Hz, 2H), 7.39 (m, 1H), 7.35 (d, J=8.5 Hz, 2H), 7.33-7.27 (m, 2H), 7.19 (d, J=8.5 Hz, 2H), 7.12 (d, J=8.5 Hz, 2H), 1.36 (s, 12H), 1.34 (s, 9H).

(c) 2,7-dibromonaphtho[2,1-b:6,5-b']difuran

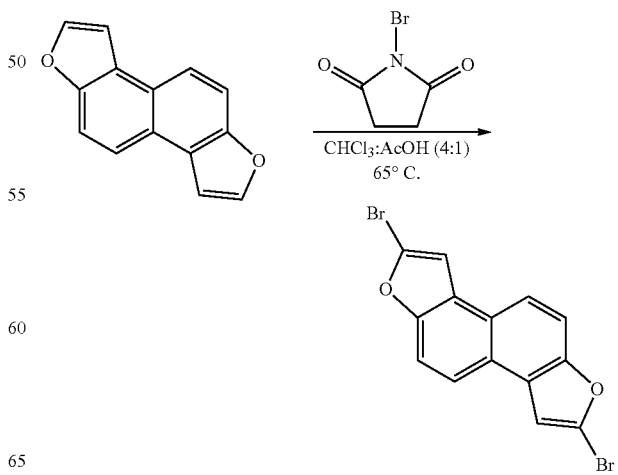

Naphtho[2,1-b:6,5-b']difuran (0.600 g, 2.88 mmol) was combined with acetic acid (6 mL) in a 100-mL 2-neck round-bottom flask. The mixture was stirred. Then N-bromosuccinimide (1.06 g, 5.96 mmol) was added slowly. The mixture was stirred at 65° C. The solution turned from light yellow to red. After 50 minutes, a dark gray suspension was observed. The reaction mixture was allowed to cool to room temperature. The reaction mixture was purified by flash column chromatography followed by recrystallization to give a colorless powder (0.770 g, 73%). $^1$H NMR (CD$_2$Cl$_2$, 499.8 MHz) δ 7.96 (d, J=8.5 Hz, 2H), 7.75 (d, J=8.5 Hz, 2H), 7.29 (m, 2H).

(d) N,N'-(naphtho[2,1-b:6,5-b']difuran-2,7-diyl-dinaphthalene-6,2-diyl)bis[N-(4-tert-butylphenyl)biphenyl-4-amine]

phenyl-4-amine (0.875 g, 1.58 mmol) and sodium carbonate (0.301 g, 2.84 mmol). Tetrahydrofuran (8 mL) and water (1.5 mL) were added. The mixture was sparged with nitrogen for 15 min. Inside a glovebox, tetrakis(triphenylphosphine)palladium (0.097 g, 0.084 mmol) was added to a 25-mL flask followed by tetrahydrofuran (5 mL). The flask was sealed with a rubber septum, and brought out of the glovebox. The catalyst solution was transferred to the reaction flask via a cannula. The reaction mixture was stirred at 85° C. for about 17 h. The crude product was purified by flash silica chromatography to yield a yellow powder (0.060 g, 8%). $^1$H NMR (CD$_2$Cl$_2$, 499.8 MHz) δ 8.37 (s, 2H), 8.13 (d, J=8.8 Hz, 2H), 7.96 (d, J=8.5 Hz, 2H), 7.87-7.85 (m, 4H),

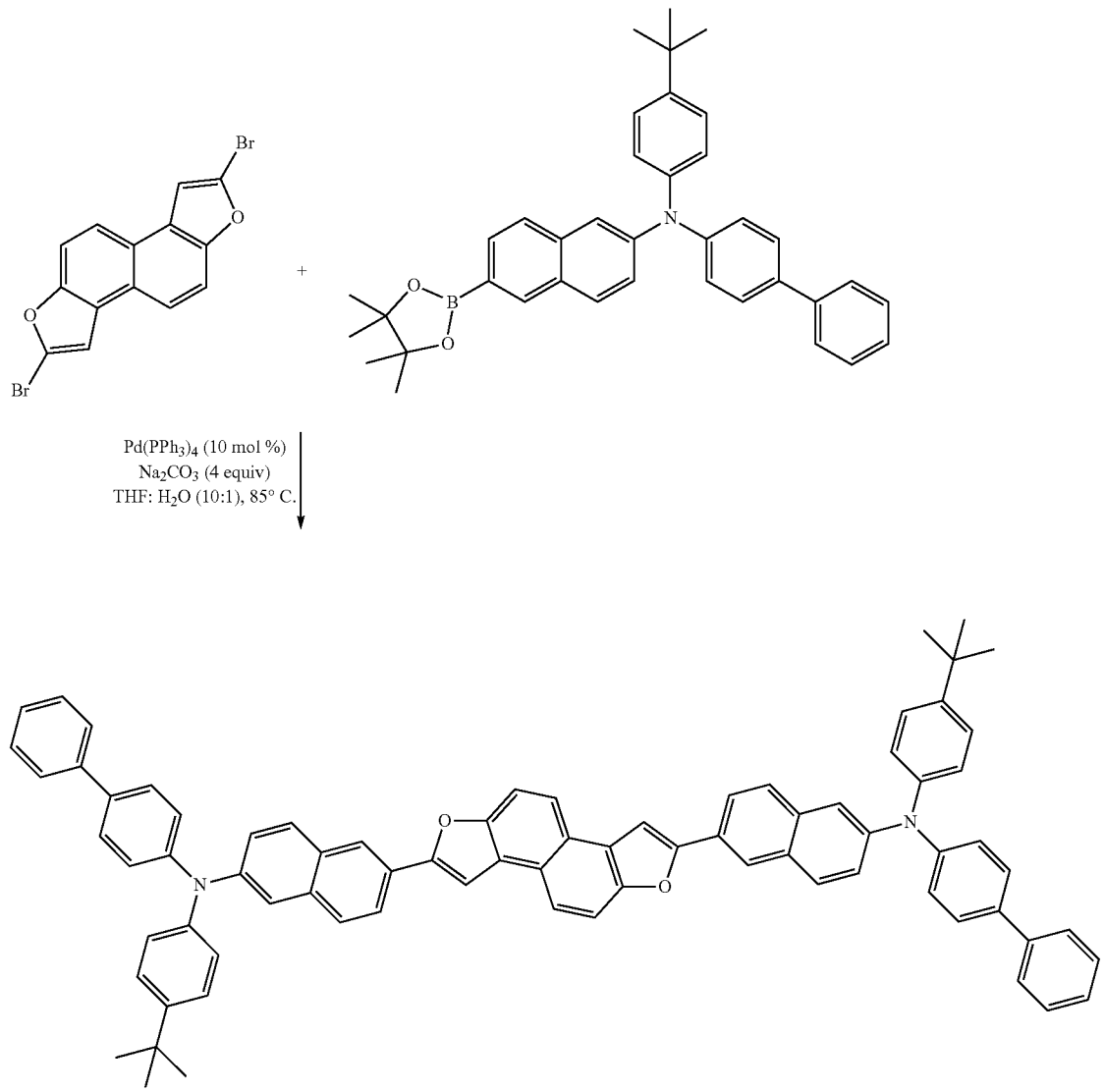 [SMILES: Brc1cc2c(ccc3c4cc(Br)oc4ccc23)o1 ; CC(C)(C)c1ccc(N(c2ccc(-c3ccccc3)cc2)c2ccc3cc(B4OC(C)(C)C(C)(C)O4)ccc3c2)cc1 ; CC(C)(C)c1ccc(N(c2ccc(-c3ccccc3)cc2)c2ccc3cc(-c4cc5c(ccc6c7cc(-c8ccc9cc(N(c%10ccc(-c%11ccccc%11)cc%10)c%10ccc(C(C)(C)C)cc%10)ccc9c8)oc7ccc56)o4)ccc3c2)cc1]

Into a 50-mL 2-neck round-bottom flask containing a stir bar were added 2,7-dibromonaphtho[2,1-b:6,5-b']difuran (0.250 g, 0.683 mmol), N-(4-tert-butylphenyl)-N-[6-(4,4,5,5-tetramethyl-1,3,2-dioxaborolan-2-yl)naphthalen-2-yl]bi- 7.71 (d, J=8.6 Hz, 2H), 7.68 (s, 2H), 7.63 (m, 4H), 7.56 (m, 4H), 7.47-7.43 (m, 6H), 7.40-7.362 (m, 8H), 7.23 (m, 4H), 7.16 (m, 4H), 1.37 (s, 18H). UPLC-MS APCI$^+$ (m/z) Calcd for C$_{78}$H$_{62}$N$_2$O$_2$ ([M+H]$^+$) 1059.49. Found 1061.16.

Synthesis Example 8

This example illustrates the preparation of a compound having Formula I, Compound 2-17, N,N'-(naphtho[1,2-b:5,6-b']difuran-2,7-diyldinaphthalene-6,2-diyl)bis[N-(4-tert-butylphenyl)biphenyl-4-amine].

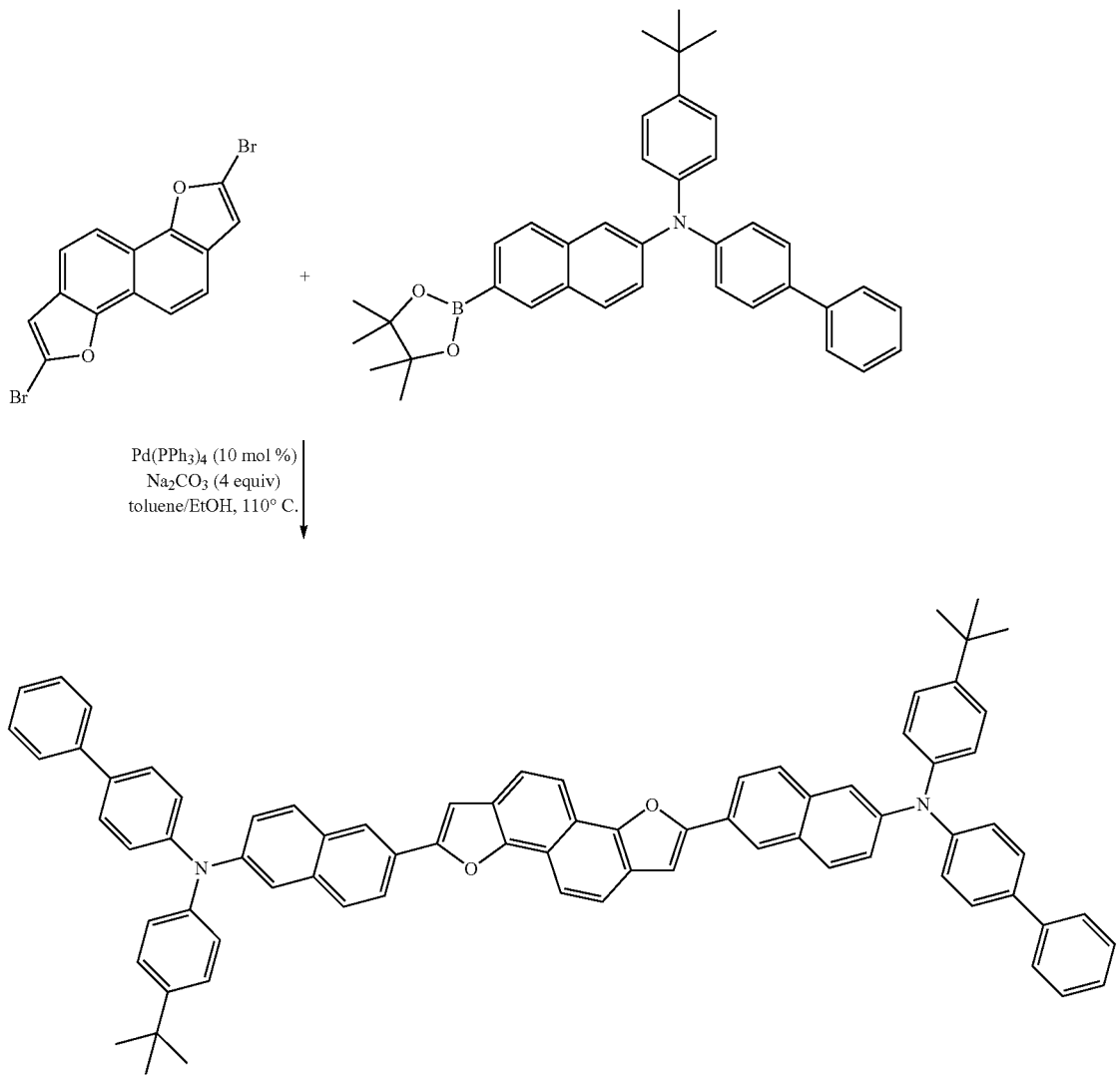 [SMILES: Brc1cc2ccc3c(ccc4cc(Br)oc43)c2o1 ; CC(C)(C)c1ccc(N(c2ccc(-c3ccccc3)cc2)c2ccc3cc(B4OC(C)(C)C(C)(C)O4)ccc3c2)cc1 ; CC(C)(C)c1ccc(N(c2ccc(-c3ccccc3)cc2)c2ccc3cc(-c4cc5ccc6c(ccc7cc(-c8ccc9cc(N(c%10ccc(-c%11ccccc%11)cc%10)c%10ccc(C(C)(C)C)cc%10)ccc9c8)oc76)c5o4)ccc3c2)cc1]

Into a 50-mL 2-neck round-bottom flask containing a stir bar were added 2,7-dibromonaphtho[1,2-b:5,6-b']difuran (0.253 g, 0.690 mmol), N-(4-tert-butylphenyl)-N-[6-(4,4,5,5-tetramethyl-1,3,2-dioxaborolan-2-yl)naphthalen-2-yl]biphenyl-4-amine (0.815 g, 1.47 mmol) and sodium carbonate (0.310 g, 2.92 mmol). Ethanol (1 mL) and water (0.8 mL) were added. The mixture was sparged with nitrogen for 20 min. Inside a glovebox, tetrakis(triphenylphosphine)palladium (0.167 g, 0.144 mmol) was added to a 25-mL flask followed by toluene (5 mL). The flask was sealed with a rubber septum, and brought out of the glovebox. The catalyst solution was transferred to the reaction flask via a cannula. The reaction mixture was stirred at 100° C. for about 15.5 h. LC analysis showed incomplete conversion of the starting materials. A 6.25:5 ethanol:water mixture was sparged with nitrogen in a sealed pear-shape flask for 20 min. Inside the glovebox, tetrakis(triphenylphosphine)palladium (0.178 g, 0.154 mmol) was added to a 25-mL pear shape flask, which was sealed with a septum. The ethanol:water mixture (1 mL) was added the reaction mixture via a syringe, followed immediately by the catalyst solution. The reaction mixture was stirred at 10° C. for another 23.75 h. Then the crude product was purified by flash silica chromatography to yield a yellow powder (0.350 g, 48%). $^{1}$H NMR (CD$_2$Cl$_2$, 499.8 MHz) δ 8.44 (s, 2H), 8.34 (d, J=8.3 Hz, 2H), 7.97 (dd, J=8.3 Hz, 2H), 7.88 (d, J=8.3 Hz, 4H), 7.72 (d, J=8.6 Hz, 2H), 7.63 (m, 4H), 7.57 (m, 4H), 7.48-7.43 (m, 6H), 7.40-7.37 (m, 6H), 7.34 (m, 4H), 7.24 (d, J=8.6 Hz, 4H), 7.16 (d, J=8.6 Hz, 4H), 1.37 (s, 18H). UPLC-MS APCI$^+$ (m/z) Calcd for C$_{78}$H$_{62}$N$_2$O$_2$ ([M+H]$^+$) 1059.49. Found 1058.23.

Synthesis Example 9

This example illustrates the preparation of a compound having Formula I, Compound 2-35, N-([1,1'-biphenyl]-4-yl)-6-(7-(4-([1,1'-biphenyl]-4-yl(3-(tert-butyl)phenyl)amino)phenyl)naphtho[1,2-b:5,6-b']difuran-2-yl)-N-(4-(tert-butyl)phenyl)naphthalen-2-amine.

101

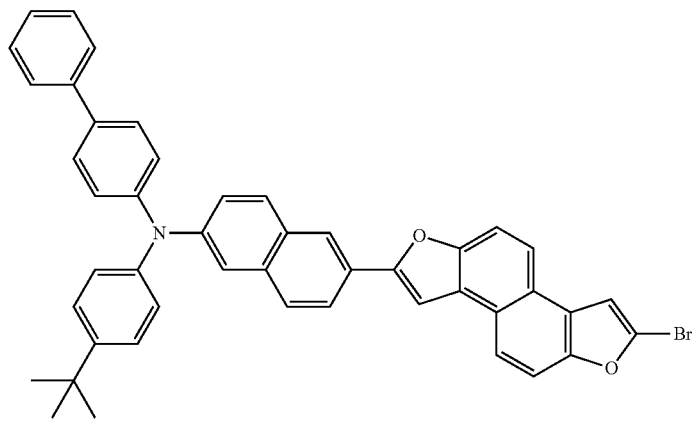

+

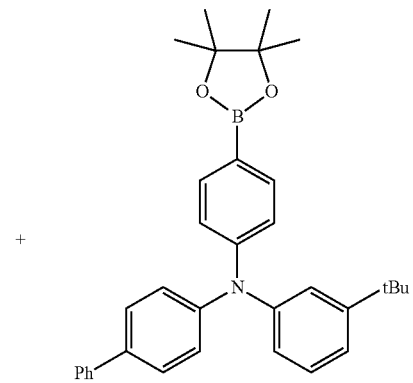

Exact Mass: 503.30
Molecular Weight: 503.49
Pd(PPh$_3$)$_4$, Na$_2$CO$_3$
Toluene, Ethanol, H$_2$O, 110° C.

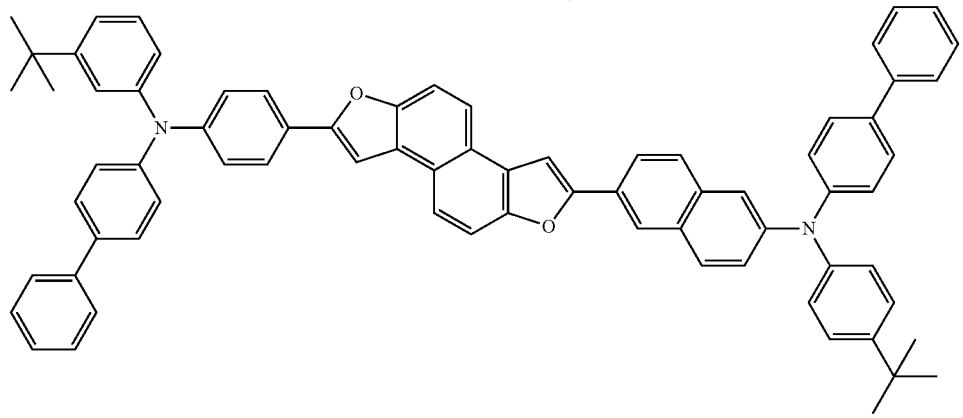

N-([1,1'-biphenyl]-4-yl)-6-(7-bromonaphtho[1,2-b:5,6-b']difuran-2-yl)-N-(4-(tert-butyl)phenyl)naphthalen-2-amine (0.240 g, 0.337 mmol), (N-(3-(tert-butyl)phenyl)-N-(4-(4,4,5,5-tetramethyl-1,3,2-dioxaborolan-2-yl)phenyl)-[1,1'-biphenyl]-4-amine (0.259 g, 0.514 mmol) and sodium carbonate (0.154 g, 1.45 mmol) were added to a 2-neck 50-mL round-bottom flask containing a stir bar. Toluene (8 mL), water (0.7 mL) and ethanol (2.0 mL) were added. The mixture was sparged with N$_2$ for 20 min. Inside a glovebox, tetrakis(triphenylphosphine)palladium (0.020 g, 0.017 mmol) and toluene (4 mL) were added to a 20-mL flask. The flask was sealed with a rubber septum, and brought out of the glovebox, and was slightly heated to form a solution. The catalyst solution was transferred to the reaction flask via a cannula. The reaction mixture was stirred at 110° C. for 16 h. The reaction mixture was allowed to cool to room temperature and purified by flash silica chromatography to yield a yellow powder (0.192 g, 56%). UPLC-MS APCI$^+$ (m/z) Calcd for C$_{74}$H$_{60}$N$_2$O$_2$ ([M+H]$^+$) 1009.47. Found 1009.61.

Synthesis Example 10

This example illustrates the preparation of a compound having Formula I, Compound 2-36.

102

(a) 3,7-bis[(4-chlorophenyl)ethynyl]naphthalene-2,6-diyl diacetate

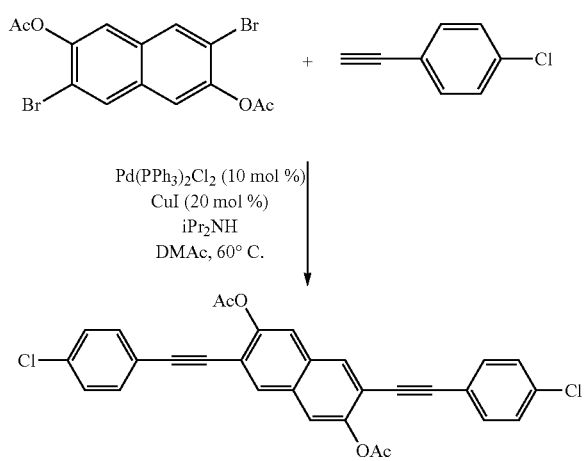

Inside a glovebox, Pd(PPh$_3$)$_2$Cl$_2$ (0.350 g, 0.497 mmol), N,N-diisopropylamine (50 mL), N,N-dimethylacetamide (50 mL) followed by CuI (0.190 g, 1.00 mmol), 3,7- dibromonaphthalene-2,6-diyl diacetate (2.00 g, 4.97 mmol) and 1-chloro-4-ethynylbenzene (0.466 g). The reaction mixture (a light yellow suspension) was stirred at 60° C. The rest of the alkyne (0.954 g) was added in portions over a period of about 3 min. The mixture was stirred at 60° C. for 6 h. The reaction mixture was diluted with chloroform (2×250 mL). The resulting suspension was washed with water (300 mL) with HCl (10 mL, 1N). The organic layer was separated and concentrated under the rotavap to give a sludge. The sludge was redissolved in DCM (200 mL) and washed with water (300 mL). The organic layer was passed through a plug of sodium sulfate. The dark brown solution was concentrated on the rotavap to give ~9 g of a solid. The solid was purified by flash column chromatography to give a brown solid (1.39 g, 54%).

(b) 2,7-bis(4-chlorophenyl)naphtho[2,3-b:6,7-b']difuran 3,7-Bis[(4-chlorophenyl)ethynyl] naphthalene-2,6-diyl diacetate (0.630 g, 1.23 mmol) was added to a 2-neck 100-mL round-bottom flask, followed by N,N-Dimethylacetamide (20 mL) and cesium carbonate (4.002 g, 12.3 mmol) and deionized water (4 mL). The mixture was sparged for 20 min. It was stirred at 80° C. overnight. After cooling to room temperature, deionized water (40 mL) was added. The precipitate was filtered and washed with deionized water (20 mL), methanol (20 mL) and finally chloroform (20 mL). the precipitate was dried under reduced pressure (130 mTorr for 30 min) to give a yellow solid (0.495 g, 94%). The product was not soluble in most organic solvents at high temperature. No characterization was conducted.

(c) N,N'-(naphtho[2,3-b:6,7-b']difuran-2,7-diyldibenzene-4,1-diyl)bis[N-(3-tert-butylphenyl)biphenyl-4-amine]

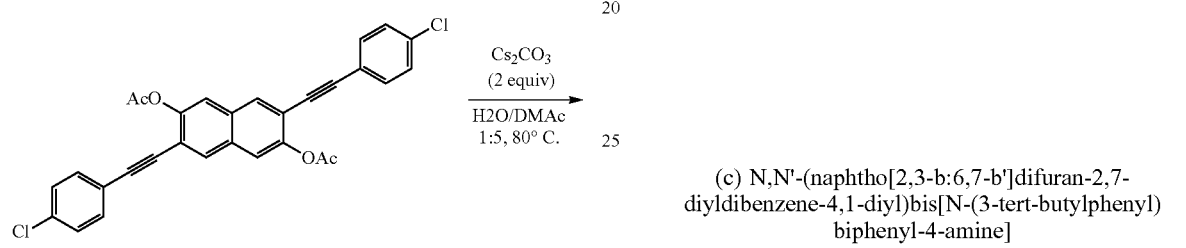

Inside a glove box, $Pd_2(DBA)_3$ (0.024 g, 0.026 mmol) and tri-tert-butylphosphine (0.023 g, 0.11 mmol) and toluene (3 mL) were combined in a 50-mL 2-neck round-bottom flask containing a stir bar. The mixture was stirred at 23° C. for 10 min. Sodium tert-butoxide (0.300 g, 3.12 mmol) was then added, followed by N-(3-(tert-butyl)phenyl)-[1,1'-biphenyl]-4-amine hydrochloride (0.433 g, 1.28 mmol), toluene (7 mL), and 2,7-bis(4-chlorophenyl)naphtho[2,3-b:6,7-b']difuran (0.242 g, 0.564 mmol). The reaction mixture was stirred at 100° C. for 15 h. The crude product was purified by flash silica chromatography to yield a yellow powder (0.270 g, 48%). $^1$H NMR ($CD_2Cl_2$, 499.8 MHz) δ 8.08 (s, 2H), 7.97 (s, 2H), 7.83 (d, J=8.7 Hz, 4H), 7.63 (m, 4H), 7.57 (m, 4H), 7.45 (m, 4H), 7.34 (m, 2H), 7.31-7.27 (m, 4H), 7.24-7.18 (m, 10H), 7.07 (s, 2H), 6.99 (m, 2H), 1.30 (s, 18H). UPLC-MS APCI$^+$ (m/z) Calcd for $C_{70}H_{58}N_2O_2$ ([M+H]$^+$) 959.46. Found 960.09.

Synthesis Example 11

This example illustrates the preparation of a compound having Formula I, Compound 2-37, N,N'-(naphtho[2,3-b:6,7-b']difuran-2,7-diyldibenzene-4,1-diyl)bis[N-(3-tert-butylphenyl)biphenyl-3-amine].

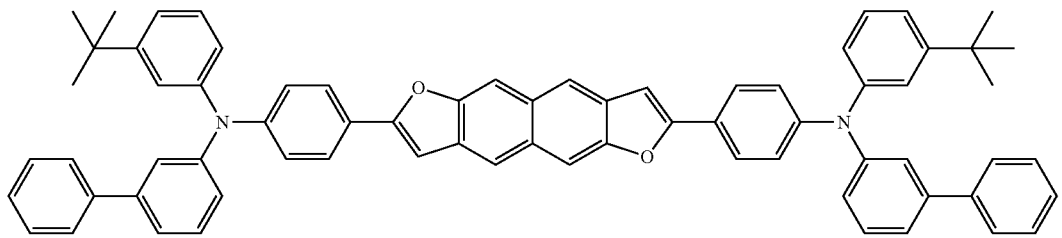 [SMILES: CC(C)(C)c1cccc(N(c2ccc(-c3cc4cc5cc6oc(-c7ccc(N(c8cccc(-c9ccccc9)c8)c8cccc(C(C)(C)C)c8)cc7)cc6cc5cc4o3)cc2)c2cccc(-c3ccccc3)c2)c1]

Inside a glove box, $Pd_2(DBA)_3$ (0.024 g, 0.026 mmol) and tri-tert-butylphosphine (0.016 g, 0.079 mmol) and toluene (3 mL) were combined in a 50-mL 2-neck round-bottom flask containing a stir bar. The mixture was stirred at 23° C. for 10 min. Sodium tert-butoxide (0.141 g, 1.46 mmol) was then added, followed by N-(3-tert-butylphenyl)biphenyl-3-amine (0.350 g, 1.28 mmol), toluene (7 mL), and 2,7-bis(4-chlorophenyl)naphtho[2,3-b:6,7-b]difuran (0.239 g, 0.556 mmol). The reaction mixture was stirred at 100° C. for 13 h. The crude product was purified by flash silica chromatography to yield a yellow powder (0.150 g, 28%). $^1H$ NMR ($CD_2Cl_2$, 499.8 MHz) δ 8.07 (s, 2H), 7.96 (s, 2H), 7.83 (d, J=8.8 Hz, 4H), 7.55 (m, 4H), 7.44-7.37 (m, 8H), 7.35-7.31 (m, 6H), 7.29-7.25 (m, 2H), 7.21-7.17 (m, 6H), 7.13 (m, 2H), 7.06 (s, 2H), 7.00 (m, 2H), 1.30 (s, 18H). UPLC-MS $APCI^+$ (m/z) Calcd for $C_{70}H_{58}N_2O_2$ ($[M+H]^+$) 959.46. Found 959.47.

Synthesis Example 12

This example illustrates the preparation of a compound having Formula I, Compound 2-38, N,N'-(naphtho[2,3-b:6,7-b']difuran-2,7-diyldibenzene-4,1-diyl)bis[3-methyl-N-(2-methylphenyl)biphenyl-4-amine].

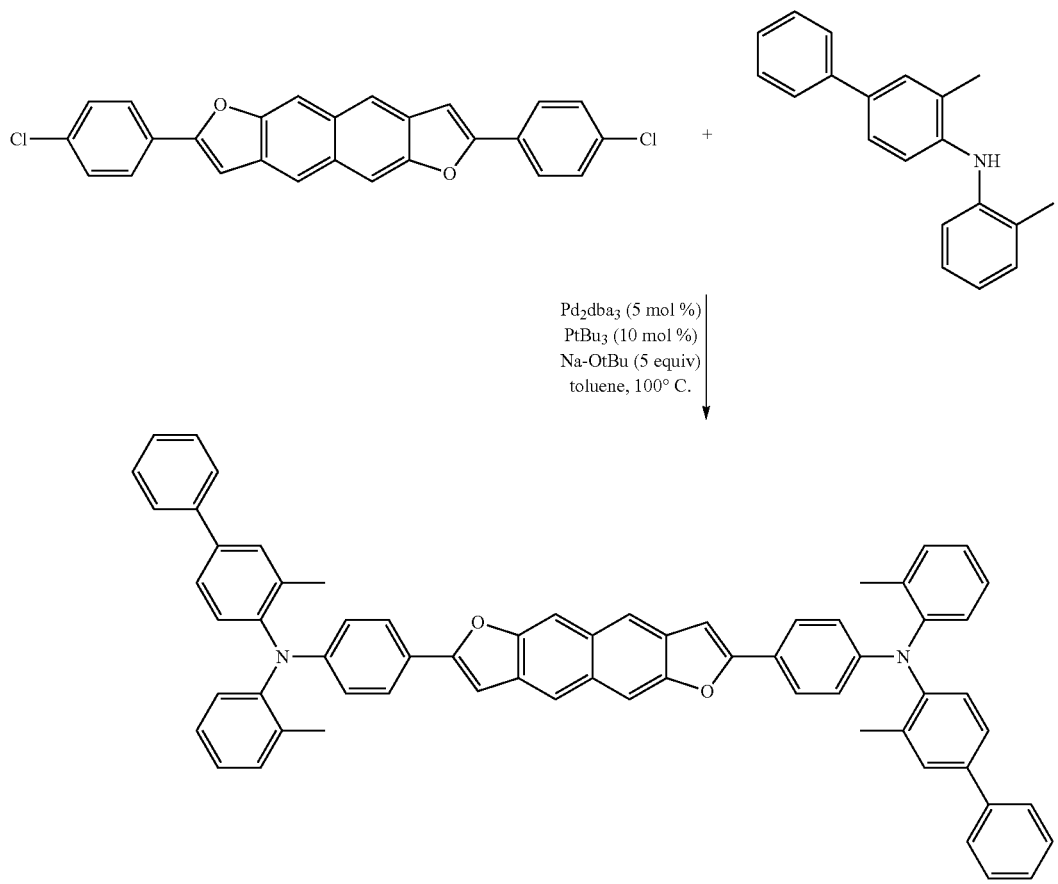

Inside a glove box, Pd$_2$(DBA)$_3$ (0.028 g, 0.031 mmol) and tri-tert-butylphosphine (0.018 g, 0.089 mmol) and toluene (3 mL) were combined in a 50-mL 2-neck round-bottom flask containing a stir bar. The mixture was stirred at 23° C. for 10 min. Sodium tert-butoxide (0.142 g, 1.46 mmol) was then added, followed by 3-methyl-N-(2-methylphenyl)biphenyl-4-amine (0.334 g, 1.22 mmol), toluene (11 mL), and 2,7-bis(4-chlorophenyl)naphtho[2,3-b:6,7-b']difuran (0.250 g, 0.582 mmol). The reaction mixture was stirred at 100° C. for 21 h. The crude product was purified by flash silica chromatography to yield a yellow powder (0.040 g, 8%). $^1$H NMR (CD$_2$Cl$_2$, 499.8 MHz) δ 8.04 (s, 2H), 7.94 (s, 2H), 7.78 (d, J=8.6 Hz, 4H), 7.64 (d, J=8.6 Hz, 4H), 7.53 (m, 2H), 7.47-7.43 (m, 6H), 7.37-7.33 (m, 2H), 7.30 (d, 2H), 7.24-7.16 (m, 4H), 7.12-7.09 (m, 4H), 7.00 (s, 2H), 6.79 (d, J=8.6 Hz, 4H), 2.17 (s, 6H), 2.14 (s, 4H). $^{13}$C NMR (CD$_2$Cl$_2$, 125.69 MHz) δ 159.3, 154.0, 150.0, 146.0, 145.4, 141.3, 138.7, 135.9(7), 135.9(2), 132.6, 131.2, 130.9(6), 129.8, 129.6, 128.7, 128.6, 127.9(6), 127.9(3), 127.6, 127.1, 126.4, 126.3, 122.6, 119.9, 117.9, 106.2, 99.3, 19.7, 19.5. UPLC-MS APCI$^+$ (m/z) Calcd for C$_{66}$H$_{50}$N$_2$O$_2$ ([M+H]$^+$) 751.33. Found 751.40.

Synthesis Example 13

This example illustrates the preparation of a compound having Formula I, Compound 2-39, N,N'-(naphtho[2,3-b:6,7-b']difuran-2,7-diyldibenzene-4,1-diyl)bis[2-methyl-N-(2-methylphenyl)aniline].

mmol) were added to a 20-mL vial, followed by 1,4-dioxane (5 mL). This mixture was was added to the reaction mixture. Sodium tert-butoxide (0.088 g, 0.92 mmol) was also added. The mixture was stirred at 100° C. for a total of 39 h. The crude product was purified by flash silica chromatography to yield a yellow powder (0.058 g, 16%). $^1$H NMR (CD$_2$Cl$_2$, 499.8 MHz) δ 8.03 (br, 2H), 7.93 (br, 2H). 7.76 (d, J=8.6 Hz, 4H), 7.28 (m, 4H), 7.21-7.13 (m, 8H), 7.05 (m, 4H), 6.99 (br, 2H), 6.72 (d, J=8.6 Hz, 4H), 2.10 (s, 12H). UPLC-MS APCI$^+$ (m/z) Calcd for C$_{54}$H$_{42}$N$_2$O$_2$ ([M+H]$^+$) 751.33. Found 751.40.

Synthesis Example 14

This example illustrates the preparation of a compound having Formula I, Compound 2-40.

(a) 3-[(4-chloro-2-methylphenyl)ethynyl][tri(propan-2-yl)]silane

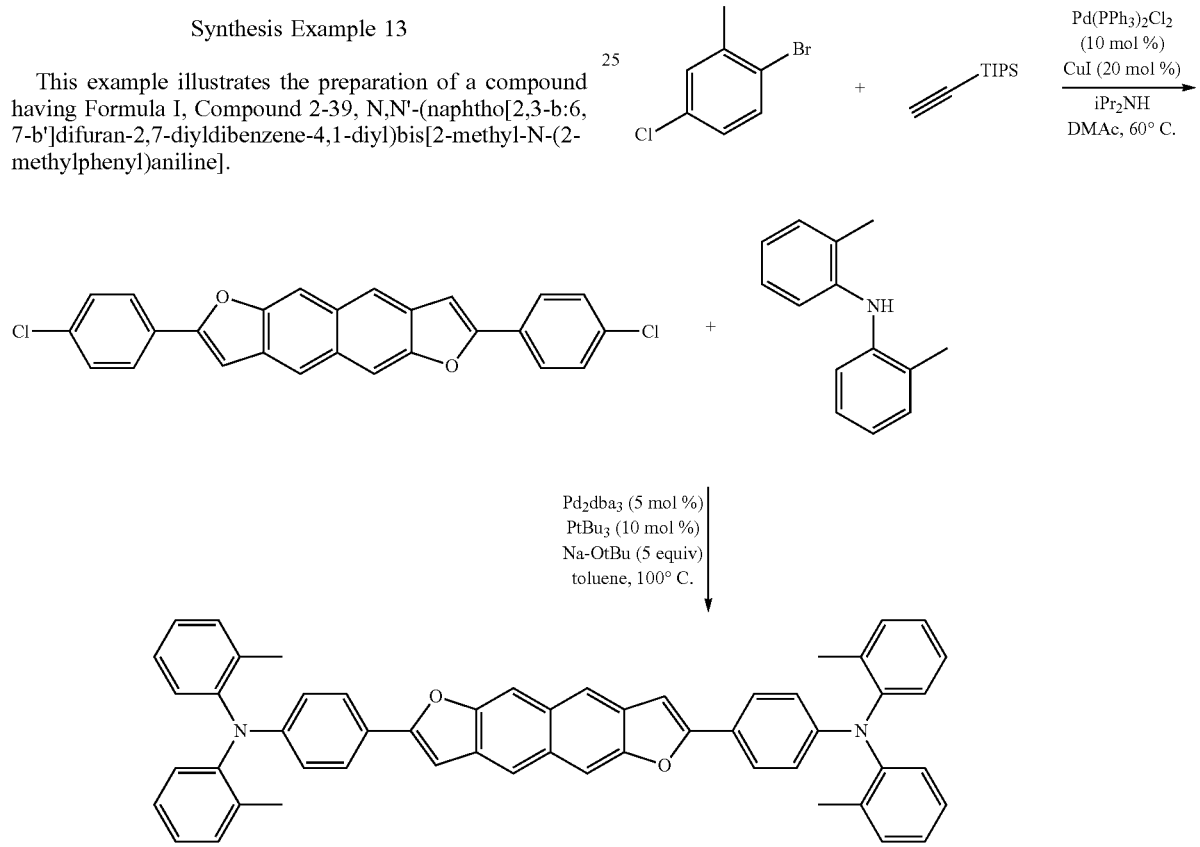

Inside a glove box, Pd$_2$(DBA)$_3$ (0.033 g, 0.036 mmol) and tri-tert-butylphosphine (0.019 g, 0.090 mmol) and toluene (3 mL) were combined in a 50-mL 2-neck round-bottom flask containing a stir bar. The mixture was stirred at 23° C. for 10 min. Sodium tert-butoxide (0.152 g, 1.58 mmol) was then added, followed by 2-methyl-N-(2-methylphenyl)benzamine (0.225 g, 1.15 mmol), toluene (7 mL), and 2,7-bis(4-chlorophenyl)naphtho[2,3-b:6,7-b']difuran (0.200 g, 0.466 mmol). The reaction mixture was stirred at 100° C. for 16 h. Then in the same glove box, Pd$_2$(DBA)$_3$ (0.030 g, 0.033 mmol) and tri-tert-butylphosphine (0.025 g, 0.123

Tetrakis(triphenylphosphine)palladium (1.73 g, 1.50 mmol), N,N-diisopropylamine (100 mL), N,N-dimethylacetamide (100 mL), CuI (1.15 g, 6.04 mmol), 2-bromo-5-chlorotoluene (6.17 g, 30.0 mmol), and (triisopropylsilyl) acetylene (1.97 g) were added to a 500-mL round-bottom flask containing a stir bar. The reaction mixture (a light yellow suspension) was sealed and plate set to 60° C. The reaction mixture was dark brown. The rest of the alkyne (4.12 g) was added in a period of 5 minutes. The reaction mixture (a dark brown suspension) was stirred for 7 h. After cooling to room temperature, the resulting suspension was added to aqueous HCl (100 mL, 1N). Dichloromethane was then added. The organic layer was separated and passed through plug of sodium sulfate.

The filtrate was then concentrated under the rotavap to give a sludge. Ethyl acetate (200 mL) and deionized water (200 mL) were added to the sludge, and the mixture was transferred to a separatory funnel and shaken well. The organic layer was separated and the black precipitate filtered off. The organic layer was washed deionized water (2×200 mL), dried over anhydrous MgSO$_4$, and filtered. It was concentrated on a rotavap to give dark brown oil (11.7 g). This oil was added used for flash column chromatography to give a light yellow oil (8.44 g, 92%). $^1$H NMR (CD$_2$Cl$_2$, 499.8 MHz) δ 7.37 (d, J=8.2 Hz, 1H), 7.22 (d, J=1.2 Hz, 1H), 7.12 (dd, J=1.2, 8.2 Hz, 1H), 2.44 (s, 3H), 1.14 (m, 18H), 1.10 (m, 3H).

(b) 4-chloro-1-ethynyl-2-methylbenzene

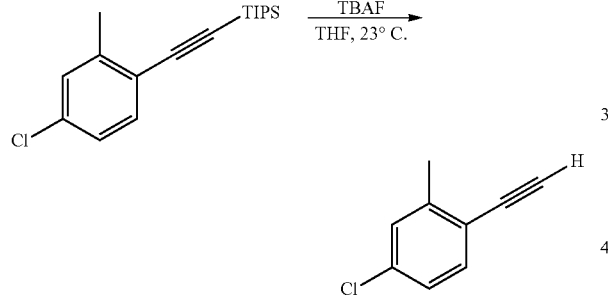

A 250-mL flask containing ((4-chloro-2-methylphenyl) ethynyl)triisopropylsilane (4.0 g, 13 mmol) was sealed with a rubber septum. The flask was evacuated and fill with N$_2$ 3× via a needle connected to the Schlenk line. Anhydrous tetrahydrofuran (20 mL) was added via a syringe, and the mixture was purged with N$_2$ via a needle immersed in the solution. Tetrabutylammonium fluoride (19 mL, 1 M, 19 mmol) was added drop-wise via a syringe over 20 minutes. A red solution was observed after a couple of drops, then a dark maroon color was observed. The reaction mixture was stirred at 23° C. for 1 h. The dark maroon solution was quenched with 20 mL of deionized water; a dark brown precipitate was observed. It was filtered and diethyl ether (100 mL) was added to the filtrate, and the mixture was stirred for 5 minutes. It was transferred to a separatory funnel and was added saturated aqueous NH$_4$Cl (10 mL). The organic layer was separated, dried over anhydrous MgSO$_4$, filtered to give a dark maroon solution. It was concentrated down on a rotavap with pump pressure (set to 405 mbar, 30° C.) in order not to lose the product. The dark maroon oil was passed through a plug of silica, and was eluted with 400 mL of hexanes to give a light yellow solution. This was concentrated down on a rotavap (pressure set to 280 mbar, 40° C.) to a give a light yellow oil (4.24 g).

By $^1$H NMR integration (desired product, hexanes and fluorotriisopropylsilane salt (1.0:1.2:1.0 mole ratio) 37% by mass of isolated material (1.56 g). The compound was used in the next step without further purification.

(c) 3,7-bis((4-chloro-2-methylphenyl)ethynyl)naphthalene-2,6-diyl diacetate

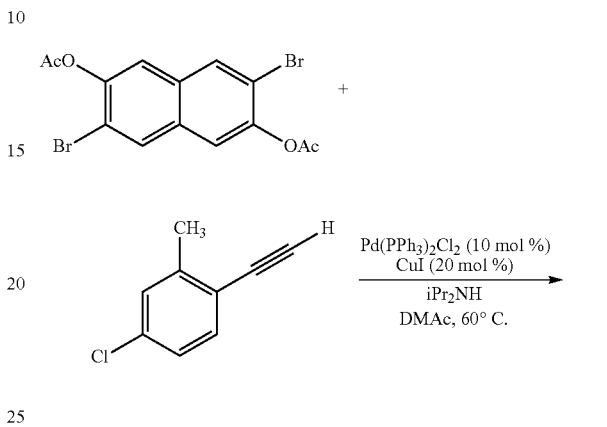

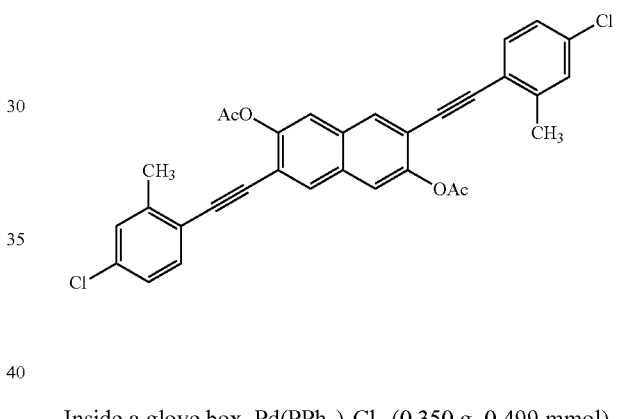

Inside a glove box, Pd(PPh$_3$)$_2$Cl$_2$ (0.350 g, 0.499 mmol), N,N-diisopropylamine (50 mL) and N,N-dimethylacetamide (50 mL), and CuI (0.192 g, 1.01 mmol) were added to a 300-mL round-bottom flask containing a stir bar. 3,7-Dibromonaphthalene-2,6-diyl diacetate (2.1 g, 5.22 mmol) was added. 4-Chloro-1-ethynyl-2-methylbenzene (1.87 g, 12.4 mmol) was added in portions over a period of 3 minutes. The reaction mixture was stirred at 60° C. for 4 h. The reaction mixture was removed from the glove box and diluted with 200 mL 4:1 hexanes:dichloromethane and passed through a plug of silica, followed by washing with dichloromethane (400 mL) to give a dark brown solution. This solution was concentrated down to give ~200 mL of dark brown solution. It was then diluted with 200 mL of dichloromethane and washed with deionized water (3×200 mL) followed by aqueous HCl (10 mL, 1 N). The organic layer was separated and dried over anhydrous magnesium sulfate. This was concentrated to give a viscous dark brown solid. The brown solid was dried on the high vacuum line at 200 torr to give a brown solid (0.603 g, 22% yield). The solid was used for the next step without further purification. $^1$H NMR (CD$_2$Cl$_2$, 499.8 MHz) δ 8.07 (s, 2H), 7.60 (s, 2H), 7.45 (d, J=8.2 Hz, 2H), 7.29 (m, 2H), 7.20 (m, 2H), 2.52 (s, 6H), 2.39 (s, 6H). UPLC-MS APCI$^+$ (m/z) Calcd for C$_{32}$H$_{22}$Cl$_2$O$_4$ ([M+H]$^+$) 541.10. Found 540.99.

(d) 2,7-Bis(4-chloro-2-methylphenyl)naphtho[2,3-b:6,7-b']difuran

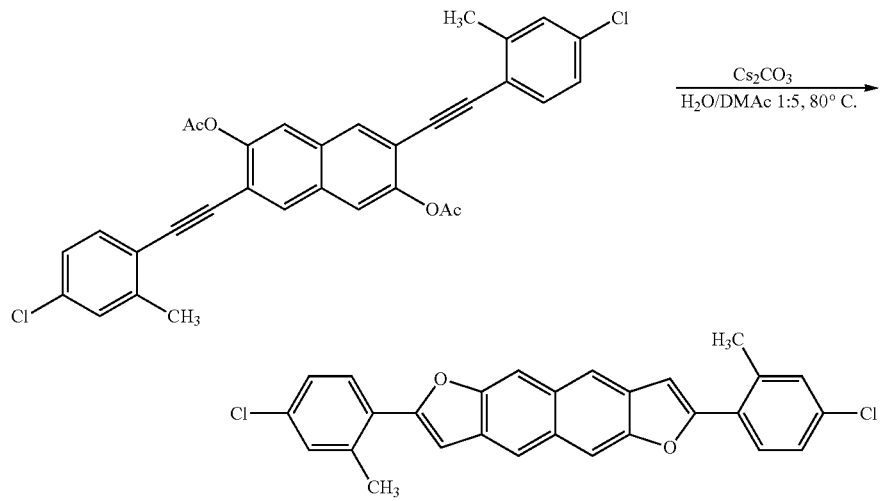

3,7-bis((4-chloro-2-methylphenyl)ethynyl)naphthalene-2,6-diyl diacetate (0.35 g, 0.65 mmol) and $Cs_2CO_3$ (2.1 g, 6.4 mmol) were added to a 100-mL round-bottom flask fitted with a reflux head and a rubber septa on the side arm. N,N-dimethylacetamide (10 mL) and deionized water (2 mL) were added. The resulted brown suspension was purged with $N_2$ for 10 min. The reaction was stirred at 80° C. for 14 h. After cooling, ethyl acetate (150 mL) was added to the reaction mixture. The mixture was filtered through a funnel. The solid was washed with water (50 mL), chloroform (20 mL) and methanol (20 mL). It was dried to constant weight to yield a light brown solid (0.175 g, 63% yield). UPLC-MS $APCI^+$ (m/z) Calcd for $C_{28}H_{18}Cl_2O_2$ ($[M+H]^+$) 457.08. Found 456.98.

(e) N,N'-(naphtho[2,3-b:6,7-t]difuran-2,7-diyldibenzene-4,1-diyl)bis[N-(3-tert-butylphenyl)biphenyl-4-amine]

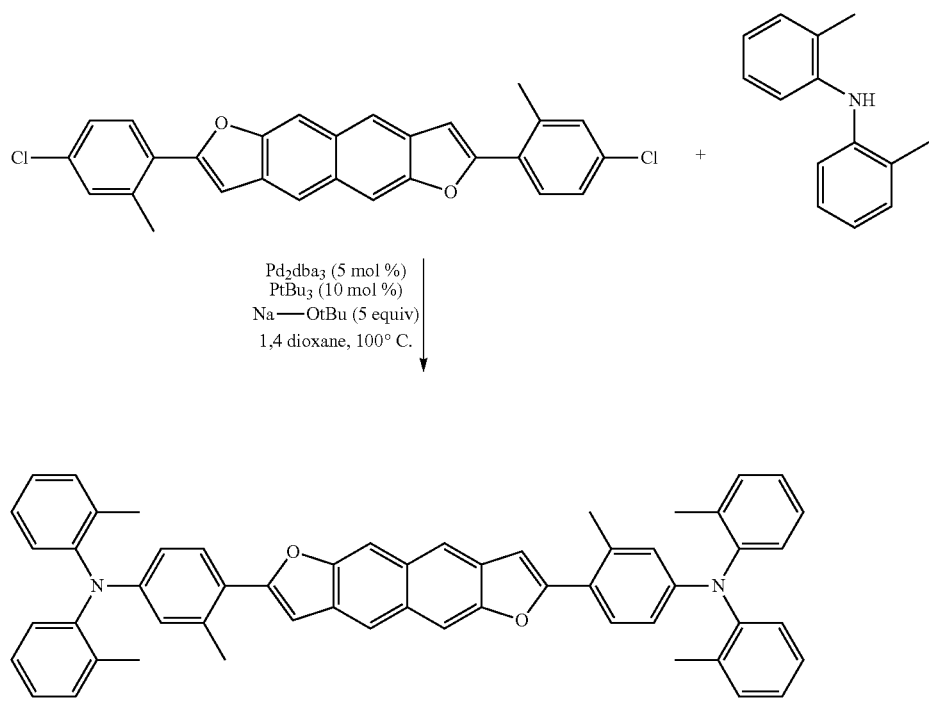

Inside a glove box, Pd$_2$(DBA)$_3$ (0.018 g, 0.019 mmol) and tri-tert-butylphosphine (0.008 g, 0.04 mmol) and 1,4-dioxane (4 mL) were combined in a 50-mL 2-neck round-bottom flask containing a stir bar. The mixture was stirred at 23° C. for 10 min. Sodium tert-butoxide (0.183 g, 1.90 mmol) was then added, followed by di-o-tolylamine (0.170 g, 0.86 mmol), 1,4-dioxane (4 mL), and 2,7-bis(4-chloro-2-methylphenyl)naphtho[2,3-b:6,7-b']difuran (0.175 g, 0.383 mmol). The reaction mixture was stirred at 100° C. for 21 h. The crude product was purified by flash silica chromatography to yield a yellow powder (0.060 g, 20%). $^1$H NMR (CD$_2$Cl$_2$, 499.8 MHz) δ 8.08 (s, 2H), 7.95 (s, 2H), 7.79 (m, 2H), 7.28 (d, 4H), 7.20-7.13 (m, 8H), 7.04 (m, 4H), 6.92 (s, 2H), 6.57-6.59 (m, 4H), 2.52 (s, 6H), 2.10 (s, 12H). UPLC-MS APCI$^+$ (m/z) Calcd for C$_{56}$H$_{46}$N$_2$O$_2$ ([M+H]$^+$) 779.36. Found 779.43.

Synthesis Example 15

This example illustrates the preparation of a compound having Formula I, Compound 2-5.

(a) 1,7-Bis-(4-bromophenyl)naphtha[2,1-b:8,7-b']difuran

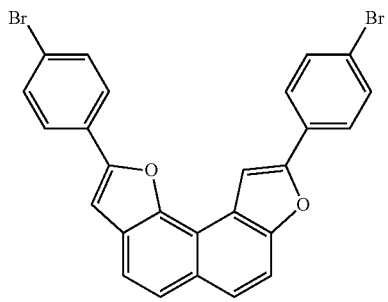 [SMILES: Brc1ccc(-c2cc3c(ccc4ccc5cc(-c6ccc(Br)cc6)oc5c43)o2)cc1]

A 100 mL 3-neck round-bottom flask was charged with 1,7-dihydroxynaphthalene (1.60 g, 10.0 mmol), 2,4'-dibromoacetophenone (8.34 g, 30.0 mmol), neutral alumina (7.14 g, 70.0 mmol) and o-xylene (40.0 mL). The mixture was sparged with nitrogen for 10 minutes and then stirred at 130° C. for 24 hours. The reaction mixture was cooled to room temperature and filtered through Celite® (120 g). The combined filtrate was concentrated under reduced pressure, purified by silica gel column chromatography (1:1 dichloromethane:hexane) followed by crystallization (1:1 toluene:isopropanol) to afford an orange solid (0.13 g, 2.5% yield). $^1$H NMR (CD$_2$Cl$_2$, 499.8 MHz) δ 7.96 (s, 1H), 7.89 (d, J=8.4 Hz, 4H), 7.85 (d, J=8.9 Hz, 1H), 7.79 (d, J=8.6 Hz, 1H), 7.71-7.65 (m, 6H), 7.27 (s, 1H).

(b) 1,7-Bis-[4-(N,N-diphenylamino)phenyl]naphtha[2,1-b:8,7-b']difuran, Compound 2-5

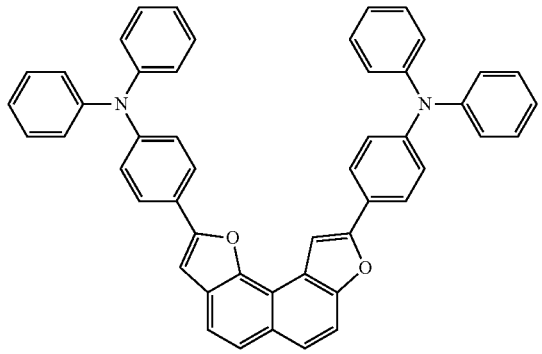 [SMILES: c1ccc(N(c2ccccc2)c2ccc(-c3cc4c(ccc5ccc6cc(-c7ccc(N(c8ccccc8)c8ccccc8)cc7)oc6c54)o3)cc2)cc1]

Inside a glovebox, 1,7-bis-(4-bromophenyl)naphtha[2,1-b:8,7-b']difuran (0.10 g, 0.20 mmol), diphenylamine (0.07 g, 0.40 mmol), sodium t-butoxide (0.06 g, 0.6 mL), tri-t-butylphosphine (0.01 g, 0.04 mmol), and tris(dibenzylideneacetone) dipalladium(0) (0.02 g, 0.02 mmol) were mixed with dry toluene (1.3 mL). The reaction mixture was stirred at room temperature for 17 hours, filtered through Celite® (50 g), and concentrated under reduced pressure. The crude product obtained was purified by silica gel column chromatography (1:4 dichloromethane:hexane). The purified product was then passed through a 3-layered plug of basic alumina (60 g), Florisil® (60 g), and silica gel (60 g), then eluted with toluene (700 mL). The collected filtrate was concentrated under reduced pressure to ~30 mL and to the concentrated solution was added acetonitrile (60 mL) slowly. The resulting crystalline solid was isolated, rinsed with methanol (30 mL), and dried under reduced pressure to afford a white solid (0.10 g, 98% yield, 98% purity). $^1$H NMR (CD$_2$Cl$_2$, 499.8 MHz) δ 7.88 (d, J=8.6 Hz, 2H), 7.87-7.84 (m, 3H), 7.81 (d, J=9.0 Hz, 1H), 7.77 (d, J=8.5 Hz, 1H), 7.69-7.66 (m, 2H), 7.33-7.29 (m, 8H), 7.19-7.13 (m, 13H), 7.12-7.05 (m, 4H).

Synthesis Example 16

This example illustrates the preparation of a compound having Formula I, Compound 2-6.

(a) 2,7-Bis-(1,1-dimethoxyethoxy)naphthalene

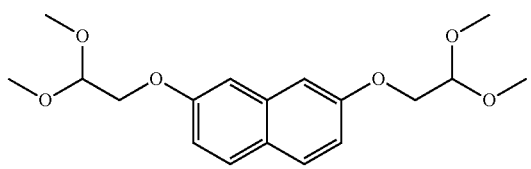

Inside a glovebox, 2,7-dihydroxynaphthalene (1.61 g, 10.0 mmol) was dissolved in N,N-dimethylformamide (33.3 mL). To the solution was added sodium hydride (0.48 g, 20.0 mmol) portionwise. The reaction mixture was stirred for 30 minutes. 2-Bromo-1,1-dimethoxyethane (3.72 g, 22.0 mmol) was added dropwise. After the completion of addition the reaction mixture was stirred at 130° C. for 18 hours. The reaction mixture was cooled to room temperature, brought out of glovebox, and quenched into water (200 mL). The quenched mixture was extracted with ethyl acetate (3×100 mL), dried over MgSO$_4$, and concentrated under reduced pressure. The crude product obtained was crystallized with isopropanol (60 mL) to afford a white solid (2.30 g, 68% yield). $^1$H NMR (CD$_2$Cl$_2$, 499.8 MHz) δ 7.68 (d, J=9.0 Hz, 2H), 7.07 (d, J=2.0 Hz, 2H), 7.01 (dd, J=8.9, 2.3 Hz, 2H), 4.75 (t, J=5.2 Hz, 2H), 4.09 (d, J=5.2 Hz, 4H), 3.46 (s, 12H).

(b) Naphtha[2,1-b:7,8-b']difuran

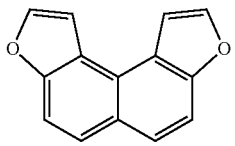 [SMILES: c1cc2c(ccc3ccc4occc4c32)o1]

A 100 mL 3-neck round-bottom flask was charged with 2,7-bis-(1,1-dimethoxyethoxy)naphthalene (1.01 g, 3.00 mmol) dissolved in chlorobenzene (30.0 mL). To the chlorobenzene solution was added polyphosphoric acid (10.0 g). The reaction mixture was heated at reflux with stirring for 19 hours then cooled to room temperature, passed through a filter and the filtrate was saved. The isolated greyish solid was rinsed with hot toluene (3×100 mL), dissolved in water (200 mL) and further extracted with toluene (3×50 mL). All organic filtrates and extract layers were combined, washed with brine (3×50 mL), dried over magnesium sulfate, and concentrated under reduced pressure. The crude product obtained was purified by silica gel column chromatography (8:92 dichloromethane:hexane) to afford a white solid (0.28 g, 33% yield). $^1$H NMR (CD$_2$Cl$_2$, 499.8 MHz) δ 7.89-7.87 (m, 4H), 7.69 (d, J=9.0 Hz, 2H), 7.48 (d, J=1.9 Hz, 2H).

(c) 2,7-Dibromonaphtha[2,1-b:7,8-b']difuran

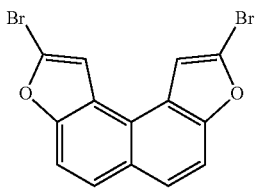 [SMILES: Brc1cc2c(ccc3ccc4oc(Br)cc4c32)o1]

A 100 mL 3-neck round-bottom flask was charged with naphtha[2,1-b:7,8-b']difuran (0.21 g, 1.00 mmol), acetic acid (3.0 mL) and chloroform (3.0 mL). A solution of N-bromosuccinimide (0.36 g, 2.00 mmol) in chloroform (12.0 mL) was added dropwise over 30 minutes. After the addition, the reaction mixture was stirred at 50° C. for 4 hours, then 60° C. for 18 hours. The reaction was cooled to room temperature and sodium bisulfite solution (1.0 M, 50 mL) was added with stirring. The organic layer was extracted with chloroform (3×30 mL), dried over MgSO$_4$, and concentrated under reduced pressure. The crude product was purified by silica gel column chromatography (2:98 dichloromethane:hexane) to afford a white solid (0.36 g, 98% yield). $^1$H-NMR (CD$_2$Cl$_2$, 499.8 MHz) δ 7.83 (d, J=9.0 Hz, 2H), 7.65 (d, J=9.0 Hz, 2H), 7.33 (s, 2H).

(d) N,N-Diphenyl-N-(6-bromo-2-naphthyl)amine

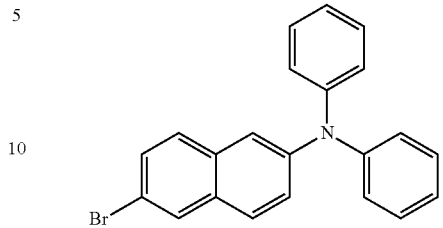

Inside a glovebox, 2,6-dibromonaphthalene (1.86 g, 6.50 mmol), diphenylamine (0.85 g, 5.00 mmol), sodium t-butoxide (0.72 g, 7.50 mmol), 1,1'-bis(diphenylphosphino)ferrocene (0.06 g, 0.10 mmol), and tris(dibenzylideneacetone) dipalladium(0) (0.09 g, 0.10 mmol) were mixed with dry toluene (33.3 mL). The reaction mixture was stirred in 35° C. for 18 hours, 45° C. for 4 hours, and then 60° C. for 19 hours. The reaction mixture was cooled to room temperature, filtered through Celite® (60 g) and concentrated under reduced pressure. The crude product was purified by silica gel column chromatography (5:95 dichloromethane:hexane) to afford a white solid (1.50 g, 80% yield). $^1$H NMR (CD$_2$Cl$_2$, 499.8 MHz) δ 7.91 (s, 1H), 7.62 (d, J=8.9 Hz, 1H), 7.45 (t, J=8.7 Hz, 2H), 7.34 (d, J=1.5 Hz, 1H), 7.29 (app. t, J=7.6 Hz, 5H), 7.11 (d, J=8.3 Hz, 4H), 7.08 (t, J=7.4 Hz, 2H).

(e) N,N-Diphenyl-N-[6-(4,4,5,5-tetramethyl-1,3,2-dioxaborolan-2-yl)-2-naphthyl]amine

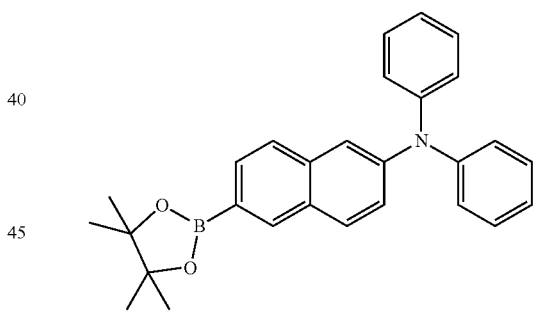

A 100 mL 3-neck round-bottom flask was charged with N,N-diphenyl-N-(6-bromo-2-naphthyl)amine (0.75 g, 2.00 mmol), bis(pinacolato)diboron (0.76 g, 3.00 mmol), potassium acetate (0.59 g, 6.00 mmol) and 1,4-dioxane (15.4 mL). The mixture was sparged with nitrogen for 20 minutes then [1,1'-bis(diphenylphosphino)-ferrocene]dichloropalladium(II), complex with dichloromethane (1:1) (0.05 g, 0.06 mmol) was added to the reaction mixture. The reaction mixture was stirred at 80° C. for 17 hours, cooled to room temperature, filtered through Celite® (60 g) and concentrated under reduced pressure. The crude product obtained was purified by silica gel column chromatography (4:96 ethyl acetate:hexane) to afford a colorless oil (0.60 g, 71% yield). $^1$H NMR (CD$_2$Cl$_2$, 499.8 MHz) δ 8.21 (s, 1H), 7.74 (d, J=8.9 Hz, 1H), 7.67 (d, J=8.2 Hz, 1H), 7.52 (d, J=8.2 Hz, 1H), 7.34 (d, J=1.4 Hz, 1H), 7.29 (t, J=7.8 Hz, 4H), 7.23 (dd, J=8.8, 2.1 Hz, 1H), 7.13 (d, J=7.7 Hz, 4H), 7.07 (t, J=7.3 Hz, 2H), 1.36 (s, 12H).

(f) 2,7-Bis-[(N,N-diphenylamino)-6-naphth-2-yl]naphtho[2,1-b:7,8-b']difuran, Compound 2-6

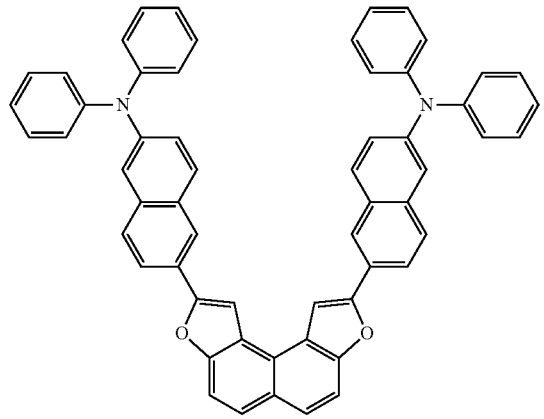 [SMILES: c1ccc(N(c2ccccc2)c2ccc3cc(-c4cc5c(ccc6ccc7oc(-c8ccc9cc(N(c%10ccccc%10)c%10ccccc%10)ccc9c8)cc7c65)o4)ccc3c2)cc1]

A 100 mL 3-neck round-bottom flask was charged with sodium carbonate (0.66 g, 6.25 mmol) and Aliquat™ 336 (0.04 g, 0.10 mmol) and a biphasic mixture of toluene (6.25 mL) and water (3.12 mL). 2,7-dibromonaphtha[2,1-b:7,8-b']difuran (0.18 g, 0.50 mmol) and N,N-diphenyl-N-[6-(4,4,5,5-tetramethyl-1,3,2-dioxaborolan-2-yl)-2-naphthyl]amine (0.51 g, 1.20 mmol) were added to the biphasic mixture which was sparged with nitrogen for 30 minutes. Finally, tetrakis(triphenylphosphine)palladium(0) (0.03 g, 0.03 mmol) was added into the reaction mixture. The reaction mixture was heated to reflux and stirred for 30 hours. The reaction was cooled to room temperature and extracted with ethyl acetate (3×50 mL). The combined organic layer was washed with brine (2×100 mL), dried over $MgSO_4$, and concentrated under reduced pressure. The crude product obtained was purified by silica gel column chromatography (1:4 dichloromethane:hexane) followed by passing through a 3-layered plug of basic alumina (60 g), Florisil® (60 g), and silica gel (60 g), eluted with toluene (700 mL), then an acidic alumina plug (120 g), and finally, crystallization (1:2 toluene:acetonitrile) to afford a yellow solid (0.12 g, 31% yield, 99.6% purity). $^1$H NMR ($CD_2Cl_2$, 499.8 MHz) δ 8.43 (s, 2H), 8.03 (dd, J=8.7, 1.3 Hz, 2H), 7.91-7.85 (m, 6H), 7.77 (d, J=9.0 Hz, 2H), 7.72 (d, J=8.8 Hz, 2H), 7.42 (d, J=1.2 Hz, 2H), 7.35-7.30 (m, 10H), 7.17 (d, J=7.8 Hz, 8H), 7.10 (t, J=7.3 Hz, 4H).

Synthesis Example 17

This example illustrates the preparation of a compound having Formula I, Compound 2-7.

(a) 1,7-Bis-(1,1-dimethoxyethoxy)naphthalene

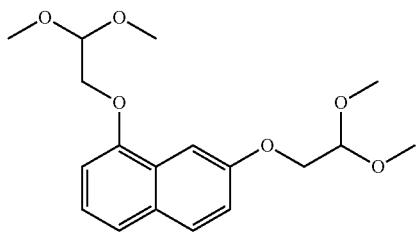

1,7-bis-(1,1-dimethoxyethoxy)naphthalene was prepared under the same conditions as those used to prepare 2,7-bis-(1,1-dimethoxyethoxy)naphthalene. The crude product was purified by silica gel column chromatography (2:98 dichloromethane:hexane) to afford the desired product as a colorless oil (7.70 g, 76% yield). $^1$H NMR ($CD_2Cl_2$, 499.8 MHz) δ 7.73 (d, J=9.0 Hz, 1H), 7.58 (d, J=2.2 Hz, 1H), 7.39 (d, J=8.2 Hz, 1H), 7.26 (t, J=8.2 Hz, 1H), 7.18 (dd, J=8.9, 2.5 Hz, 1H), 6.85 (d, J=7.6 Hz, 1H), 4.87 (t, J=5.1 Hz, 1H), 4.77 (t, J=5.2 Hz, 1H), 4.17 (d, J=5.1 Hz, 2H), 4.13 (d, J=5.1 Hz, 2H), 3.50 (s, 6H), 3.47 (s, 6H).

(b) Naphtha[2,1-b:8,7-b']difuran

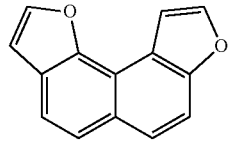 [SMILES: c1cc2c(ccc3ccc4ccoc4c32)o1]

Naphtha[2,1-b:8,7-b']difuran was prepared under the same conditions as those used to prepare naphtha[2,1-b:7,8-b']difuran. The reaction gave the desired product as a white solid (1.20 g, 38% yield). $^1$H NMR ($CD_2Cl_2$, 499.8 MHz) δ 7.93 (d, J=1.9 Hz, 1H), 7.86 (d, J=8.9 Hz, 2H), 7.80 (d, J=8.5 Hz, 1H), 7.69-7.72 (m, 3H), 7.01 (d, J=1.8 Hz, 1H).

(c) 1,7-Dibromonaphtha[2,1-b:8,7-b']difuran

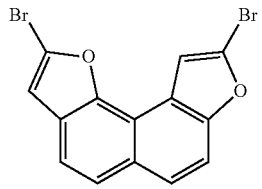 [SMILES: Brc1cc2c(ccc3ccc4cc(Br)oc4c32)o1]

1,7-Dibromonaphtha[2,1-b:8,7-b']difuran was prepared under the same conditions as those used to prepare 2,7-dibromonaphtha[2,1-b:7,8-b']difuran. The desired product was obtained as a white solid (1.46 g, 91% yield). $^1$H NMR ($CD_2Cl_2$, 499.8 MHz) δ 7.81 (d, J=9.0 Hz, 1H), 7.78 (d, J=8.5 Hz, 1H), 7.61-7.66 (m, 3H), 6.96 (s, 1H).

(d) 1,7-Bis-[(N,N-diphenylamino)-6-naphth-2-yl]naphtho[2,1-b:8,7-b']difuran, Compound 2-7

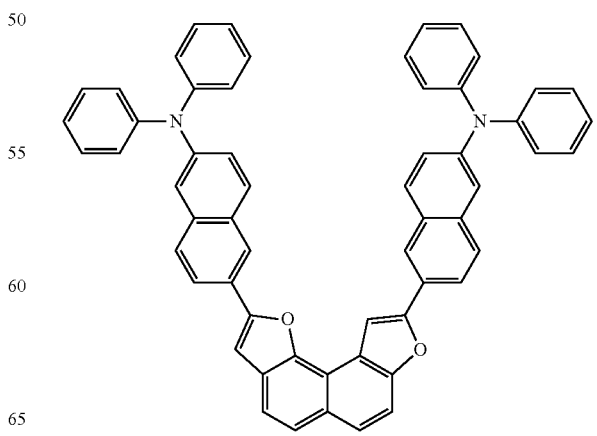

1,7-Bis-[(N,N-diphenylamino)-6-naphth-2-yl]naphtho[2,1-b:8,7-b']difuran was prepared under the same conditions as those used to prepare 2,7-bis-[(N,N-diphenylamino)-6-naphth-2-yl]naphtho[2,1-b:7,8-b']difuran, Compound 2-6 in Synthesis Example 16. The crude product was purified by silica gel column chromatography (1:4 dichloromethane:hexane), followed by purification with a 3-layered plug of basic alumina (60 g), Florisil® (60 g), and silica gel (60 g), eluted with toluene (700 mL), and then crystallization (2:1 acetonitrile:toluene). The crystallized product and the remaining mother liquor were separately repurified by silica gel column chromatography (1:4 dichloromethane:hexane). The purest fractions were combined and concentrated, and the resulting solid was triturated with acetonitrile (30 mL) at 75° C. for 2 hours to afford a yellow solid (0.04 g, 12% yield). $^1$H NMR (CD$_2$Cl$_2$, 499.8 MHz) δ 8.44 (d, J=13.3 Hz, 2H), 8.16 (s, 1H), 8.06 (ddd, J=12.5, 8.6, 1.6 Hz, 2H), 7.92 (d, J=9.0 Hz, 1H), 7.88 (dd, J=8.7, 6.4 Hz, 2H), 7.82 (d, J=8.6 Hz, 1H), 7.75 (d, J=8.6 Hz, 1H), 7.74 (t, J=8.3 Hz, 3H), 7.43 (dd, J=6.7, 1.6 Hz, 2H), 7.37 (dd, J=8.8, 2.2 Hz, 2H), 7.35-7.30 (m, 9H), 7.19-7.16 (m, 8H), 7.10 (dt, J=7.4, 1.2 Hz, 4H).

Synthesis Example 18

This example illustrates the preparation of a compound having Formula I, Compound 2-8.

(a) 1,7-Dimethoxy-6-bromonaphthalene

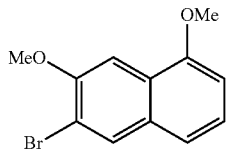 [SMILES: COc1cc2c(OC)cccc2cc1Br]

A 500 mL round-bottom flask, under nitrogen, was charged with a solution of 1,7-dimethoxynaphthalene (9.5 g 50.5 mmol) in THF (150 mL) and cooled −68° C. A 1.6 M solution of n-BuLi in hexanes (70 mL, 112 mmol) was added over 12 minutes. The reaction was warmed to room temperature slowly, and after 3 h 1,2-dibromoethane (26 mL, 302 mmol) was added over 4-minutes. After 21 hours, saturated aqueous NH$_4$Cl was added and the contents extracted with dichloromethane. The combined extracts were dried over sodium sulfate, filtered, and the filtrate was concentrated under reduced pressure. The product was purified by silica gel column chromatography (dichloromethane/hexane) to afford a white solid (7.16 g, 53%). $^1$H NMR (CD$_2$Cl$_2$, 499.8 MHz) δ 8.05 (s, 1H), 7.61 (s, 1H), 7.32 (s, 1H), 7.31 (s, 1H), 6.90-6.85 (m, 1H), 4.03 (s, 3H), 4.03 (s, 3H). UPLC-MS APCI$^+$ (m/z) Calcd for C$_{12}$H$_{11}$BrO$_2$ ([M]$^+$) 265.99. Found 265.94. Calcd for C$_{12}$H$_{11}$BrO$_2$ ([M+2H]$^+$) 268.01. Found 268.00.

(b) 1,7-Dimethoxy-6-phenylnaphthalene

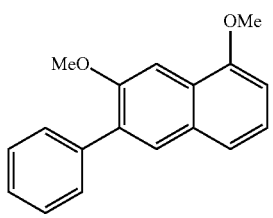 [SMILES: COc1cc2c(OC)cccc2cc1-c1ccccc1]

A 250 mL round-bottom flask was charged with 1,7-dimethoxy-6-bromonaphthalene (3.05 g, 11.2 mmol), phenylboronic acid (1.64 g, 13.5 mmol), 2M aq. sodium carbonate (16.8 mL, 33.6 mmol) toluene (40 mL), ethanol (15 mL), and water (15 mL). The mixture was sparged for 10 minutes with nitrogen. Tetrakis(triphenylphosphine)palladium (0) (712 mg, 0.62 mmol) was added, and the reaction was heated at 90° C. After 17 h, the reaction was cooled and brine was added. The contents were extracted with dichloromethane and the combined extracts were dried over sodium sulfate, filtered, and the filtrate was concentrated under reduced pressure. The product was purified by silica gel column chromatography (dichloromethane/hexane) to afford a colorless oil (2.97 g, quant.). $^1$H NMR (CD$_2$Cl$_2$, 499.8 MHz) δ 7.74 (s, 1H), 7.65 (s, 1H), 7.64-7.60 (m, 2H), 7.49-7.44 (m, 2H), 7.43-7.37 (m, 2H), 7.31 (t, J=7.7 Hz, 1H), 6.88 (d, J=7.7 Hz, 1H), 4.06 (s, 3H), 3.96 (s, 3H). UPLC-MS APCI$^+$ (m/z) Calcd for C$_{18}$H$_{16}$O$_2$ ([M+H]$^+$) 265.13. Found 265.14.

(c) 1,7-Dihydroxy-6-phenylnaphthalene

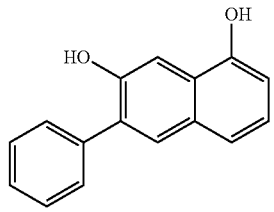 [SMILES: Oc1cc2c(O)cccc2cc1-c1ccccc1]

A 500 mL round-bottom flask was charged with 1,7-dimethoxy-6-phenylnaphthalene (2.97 g, 11.2 mmol) in dichloromethane (150 mL). A 1.0 M solution of boron tribromide in dichloromethane (67.4 mL, 69 mmol) was added at room temperature and the reaction was stirred under nitrogen. After 18 h, saturated aqueous sodium carbonate was added, followed by deionized water. The contents were extracted with dichloromethane and the combined extracts were dried over sodium sulfate, filtered, and the filtrate was concentrated under reduced pressure. The product was purified by silica gel column chromatography (dichloromethane) to afford a tan solid (2.23 g, 84%). $^1$H NMR (CD$_2$Cl$_2$, 499.8 MHz) δ 7.76 (s, 1H), 7.64-7.60 (m, 3H), 7.58-7.53 (m, 2H), 7.50-7.45 (m, 1H), 7.43 (d, J=8.2 Hz, 1H), 7.21 (t, J=7.8 Hz, 1H), 6.84 (d, J=7.5 Hz, 1H), 5.44 (d, J=1.68 Hz, 2H). UPLC-MS APCI$^+$ (m/z) Calcd for C$_{16}$H$_{12}$O$_2$ ([M+H]$^+$) 237.09. Found 237.07.

(d) 1,7-Bis(dimethoxyethoxy)-6-phenylnaphthalene

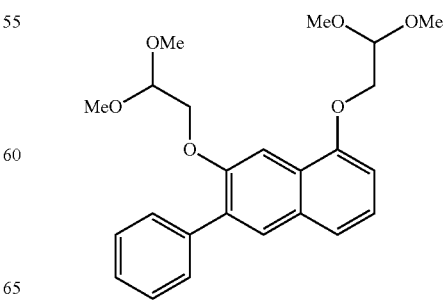

A 40 mL glass vial in a glove box was charged with 1,7-dihydroxy-6-phenylnaphthalene (1.0 g, 4.2 mmol) in N,N-dimethylformamide (10 mL) at room temperature. Sodium hydride (60% dispersion in mineral oil) (390 mg, 9.7 mmol) was added and after 1 h stirring, a solution of bromoacetaldehyde dimethyl acetal (1.65 g, 9.7 mmol) in N,N-dimethylformamide (5 mL) was added and the reaction was stirred at an external temperature=115° C. After 6 h, the reaction was cooled to room temperature. Brine was added, and the mixture was extracted with dichloromethane. The combined extracts were dried over sodium sulfate, filtered, and the filtrate was concentrated under reduced pressure. The product was purified by silica gel column chromatography (ethyl acetate/hexane) as eluent to afford a gold colored oil (1.08 g, 62%). $^1$H NMR (CD$_2$Cl$_2$, 499.8 MHz) δ 7.78 (s, 1H), 7.70-7.65 (m, 3H), 7.49-7.43 (m, 3H), 7.42-7.37 (m, 1H), 7.30 (t, J=7.9 Hz, 1H), 6.89 (d, J=7.7 Hz, 1H), 4.91 (t, J=5.3 Hz, 1H), 4.70 (t, J=5.1 Hz, 1H), 4.22 (d, J=5.3 Hz, 2H), 4.16 (d, J=5.2 Hz, 2H), 3.54 (s, 6H), 3.43 (s, 6H).

(e) 7-Phenylnaphtho[1,2-b:7,8-b']difuran

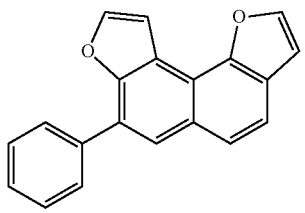 [SMILES: c1ccc(-c2cc3ccc4ccoc4c3c3ccoc23)cc1]

A 250 mL round-bottom flask was charged with 1,7-bis (dimethoxyethoxy)-6-phenylnaphthalene (1.26 g, 3.06 mmol) in chloroform (91 mL) at room temperature. Methanesulfonic acid (1.95 g, 20.5 mmol) was added and the mixture was heated under reflux. After 80 minutes, the reaction was cooled to room temperature. Saturated aqueous sodium carbonate was added, and the contents were extracted with dichloromethane. The combined extracts were dried over sodium sulfate, filtered, and the filtrate was concentrated under reduced pressure. The product was purified by silica gel column chromatography (dichloromethane/hexane) to afford a white solid (370 mg, 43%). $^1$H NMR (CD$_2$Cl$_2$, 499.8 MHz) δ 8.05-7.96 (m, 3H), 7.96 (m, 3H), 7.99-7.96 (m, 2H), 7.89 (d, J=8.6 Hz, 1H), 7.82-7.81 (d, J=2.0 Hz, 1H), 7.76 (d, J=8.6 Hz, 1H), 7.62-7.56 (m, 2H), 7.50-7.46 (m, 1H), 7.05 (d, J=2.0 Hz, 1H). Calcd for C$_{20}$H$_{12}$O$_2$ ([M+H]$^+$) 285.09. Found 285.17.

(f) 2,9-Dibromo-7-phenylnaphtho[1,2-b:7,8-b']difuran

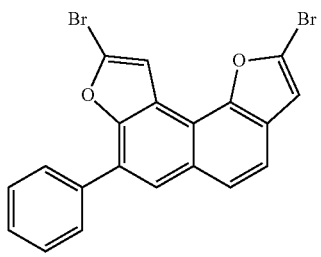 [SMILES: Brc1cc2c(o1)c(-c1ccccc1)cc1ccc3cc(Br)oc3c12]

A 40 mL glass vial was charged with 7-phenylnaphtho[1,2-b:7,8-b'] difuran (370 mg, 1.30 mmol), chloroform (12 mL), glacial acetic acid (2.4 mL) and N-bromosuccinimide (463 mg, 2.60 mmol) at room temperature. The reaction was heated at an external temp.=65° C. After 2.75 h, the reaction was cooled to room temperature. Deionized water and 2M aqueous sodium carbonate were added until the pH was between 7-9. The mixture was extracted with dichloromethane. The combined extracts were dried over sodium sulfate, filtered, and the filtrate was concentrated under reduced pressure. The product was purified by silica gel column chromatography (dichloromethane/hexane) to afford a white solid (390 mg, 68%). $^1$H NMR (CD$_2$Cl$_2$, 499.8 MHz) δ 7.99-7.94 (m, 3H), 7.63 (d, J=8.6 Hz, 1H), 7.71 (s, 1H), 7.67 (d, J=8.5 Hz, 1H), 7.62-7.56 (m, 2H), 7.52-7.47 (m, 1H), 6.99 (s, 1H).

(g) 2,9-Bis[4-(diphenylamino)phenyl]-7-phenylnaphtho[1,2-b:7,8-b']difuran, Compound 2-8

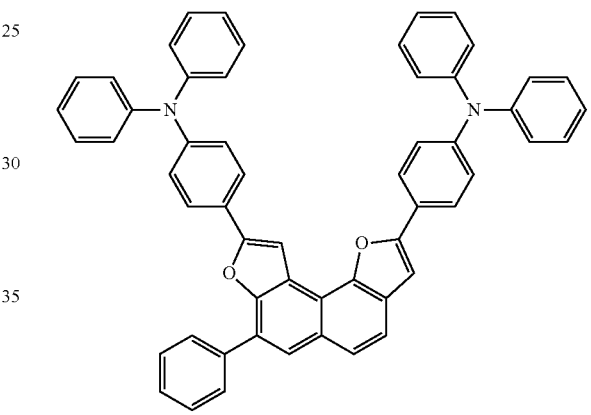

A 40 mL glass vial charged with 2,9-dibromo-7-phenylnaphtho[1,2-b:7,8-b']difuran (390 mg, 0.88 mmol), 4-(diphenylamino)phenylboronic acid (556 mg, 2.11 mmol), 2M aq. sodium carbonate (2.11 mL, 4.22 mmol), 1,4-dioxane (16 mL) and water (3.2 mL) was sparged for 15 minutes with nitrogen. Tetrakis(triphenylphosphine)palladium (0) (102 mg, 0.088 mmol) was added, and the reaction was heated at an external temp.=90° C. After 2 h, additional 2M aq. sodium carbonate (0.13 mL, 0.26 mmol) and 4-(diphenylamino)phenylboronic acid (69 mg, 0.26 mmol) were added. After heating at an external temp.=90° C. for an additional 30 minutes, the reaction was cooled and deionized water and brine were added. The contents were extracted with dichloromethane and the combined extracts were dried over sodium sulfate, filtered, and the filtrate was concentrated under reduced pressure. The product was purified by silica gel column chromatography (dichloromethane/hexane) followed by recrystallization from dichloromethane/hexane to afford a white solid (277 mg, 41%). $^1$H NMR (CD$_2$Cl$_2$, 499.8 MHz) δ 8.11-8.07 (m, 2H), 7.97 (s, 1H), 7.93-7.90 (m, 3H), 7.88-7.85 (m, 2H), 7.83 (d, J=8.6 Hz, 1H), 7.69 (d, J=8.5 Hz, 1H), 7.62-7.57 (m, 2H), 7.51-7.46 (m, 1H), 7.38-7.30 (m, 8H), 7.22-7.08 (m, 17H). UPLC-MS APCI$^+$ (m/z) Calcd for C$_{56}$H$_{38}$N$_2$O$_2$ ([M+H]$^+$) 771.30. Found 771.68.

Synthesis Example 19

This example illustrates the preparation of a compound having Formula I, Compound 2-9.

(a) N,N-Diphenyl-N-(7-bromo-9,9'-dimethylfluoren-2-yl)amine

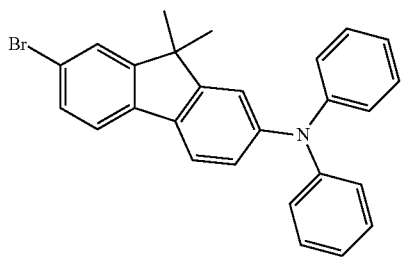 [SMILES: CC1(C)c2cc(Br)ccc2-c2ccc(N(c3ccccc3)c3ccccc3)cc21]

N,N-diphenyl-N-(7-bromo-9,9'-dimethylfluoren-2-yl)amine was prepared under the same conditions as those used to prepare N,N-diphenyl-N-(6-bromo-2-naphthyl)amine. The desired product was obtained as a white foam (1.46 g, 91% yield). $^1$H NMR (CD$_2$Cl$_2$, 499.8 MHz) δ 7.55 (d, J=8.2 Hz, 1H), 7.53-7.50 (m, 2H), 7.42 (dd, J=8.0, 1.7 Hz, 1H), 7.26 (t, J=8.2 Hz, 4H), 7.17 (d, J=1.8 Hz, 1H), 7.10 (d, J=7.6 Hz, 4H), 7.03 (dt, J=7.3, 1.1 Hz, 2H), 6.98 (dd, J=8.2, 1.9 Hz, 1H), 1.39 (s, 6H).

(b) N,N-Diphenyl-N-[7-(4,4,5,5-tetramethyl-1,3,2-dioxaborolan-2-yl)-9,9-dimethyl-fluoren-2-yl]amine

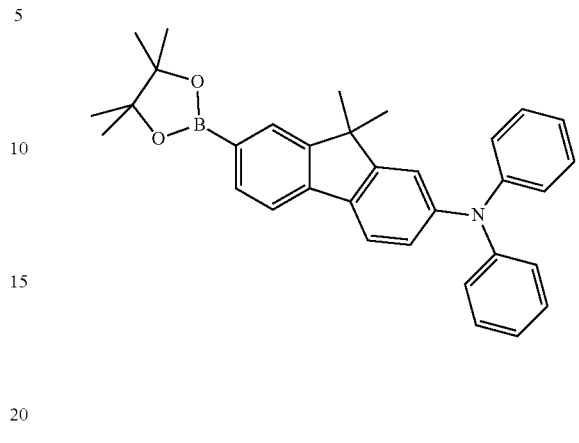

N,N-Diphenyl-N-[7-(4,4,5,5-tetramethyl-1,3,2-dioxaborolan-2-yl)-9,9-dimethyl-fluoren-2-yl]amine was prepared under the same conditions as those used to prepare N,N-diphenyl-N-[6-(4,4,5,5-tetramethyl-1,3,2-dioxaborolan-2-yl)-2-naphthyl]amine. The desired product was obtained as a colorless oil (3.40 g, 99.6% yield). $^1$H NMR (CD$_2$Cl$_2$, 499.8 MHz) δ 7.79 (s, 1H), 7.72 (dd, J=7.5, 0.7 Hz, 1H), 7.63 (d, J=7.5 Hz, 1H), 7.60 (d, J=8.2 Hz, 1H), 7.27 (t, J=8.3 Hz, 4H), 7.20 (d, J=1.9 Hz, 1H), 7.11 (d, J=7.6 Hz, 4H), 7.03 (dt, J=7.3, 0.9 Hz, 2H), 6.99 (dd, J=8.2, 2.0 Hz, 1H), 1.41 (s, 6H), 1.35 (s, 12H).

(c) 2,6-Bis-[(N,N-diphenylamino)-9,9-dimethyl-fluoren-2-yl]naphtho[2,1-b:6,5-b']difuran, Compound 2-9

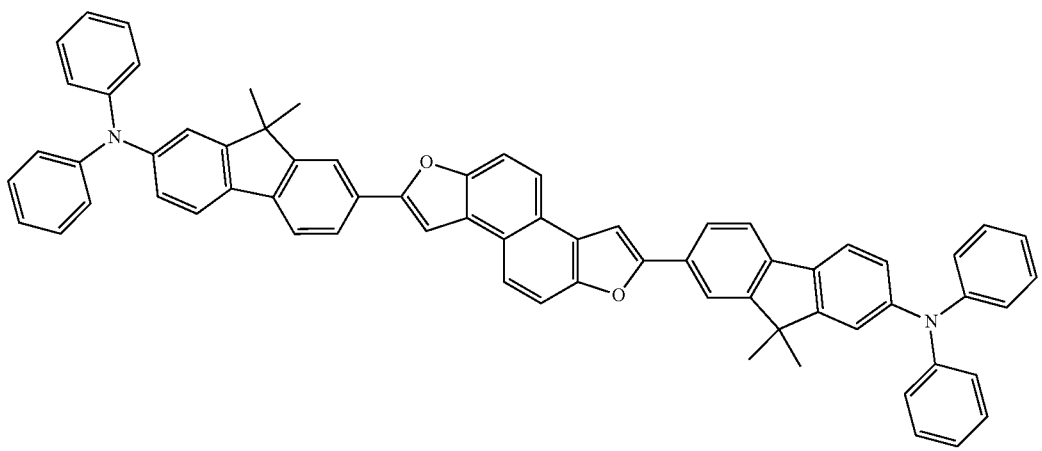 [SMILES: CC1(C)c2cc(-c3cc4c(ccc5c6cc(-c7ccc8c(c7)C(C)(C)c7cc(N(c9ccccc9)c9ccccc9)ccc7-8)oc6ccc45)o3)ccc2-c2ccc(N(c3ccccc3)c3ccccc3)cc21]

2,6-Bis-[(N,N-diphenylamino)-9,9-dimethyl-fluoren-2-yl]naphtho[2,1-b:6,5-b']difuran was prepared under the same conditions as those used to prepare 2,7-bis-[(N,N-diphenylamino)-6-naphth-2-yl]naphtho[2,1-b:7,8-b']difuran, Compound 2-6 in Synthesis Example 16. The crude product was purified by passing through a 3-layered plug of basic alumina (60 g), Florisil® (60 g), and silica gel (60 g), eluted with hot dichlorobenzene (300 mL) inside a modified (frit installed) Soxhlet extraction chamber. The collected filtrate was concentrated and triturated with 1,4-dioxane (100 mL) at 90° C. for 2 hours to afford a pale yellow solid (0.16 g, 25% yield). This compound has a poor solubility with common solvents. $^1$H NMR spectrum was not obtained. Purity: 98% (UPLC).

Synthesis Example 20

This example illustrates the preparation of a compound having Formula I, Compound 2-41.

(a) 2,6-Dimethoxy-3,7-diphenylnaphthalene

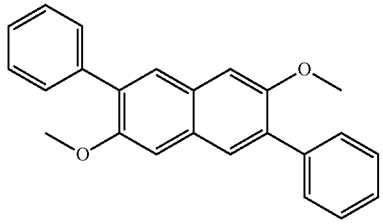 [SMILES: COc1cc2cc(-c3ccccc3)c(OC)cc2cc1-c1ccccc1]

A 250 mL 3-neck round-bottom flask was charged with 2,6-dichloro-3,7-dimethoxynaphthalene (2.06 g, 8.00 mmol), phenylboronic acid (2.34 g, 19.2 mmol) and a suspension of tribasic potassium phosphate (5.09 g, 24.0 mmol) in 1,4-dioxane (100 mL). The reaction mixture was sparged with nitrogen for 30 minutes, and then 2-dicyclohexylphosphino-2',4',6'-triisopropyl-1,1'-biphenyl (0.15 g, 0.32 mmol) and tris(dibenzylideneacetone) dipalladium(0) (0.07 g, 0.08 mmol) were added. The reaction mixture was heated to reflux and stirred for 31 hours. The reaction mixture was cooled to room temperature, filtered through Celite® (60 g), and concentrated under reduced pressure. The crude product obtained was purified by silica gel column chromatography (3:7 dichloromethane:hexane) followed by 2 crystallizations (2:1 isopropanol:ioluene) to afford a white solid (0.51 g, 23% yield). $^1$H NMR (CD$_2$Cl$_2$, 499.8 MHz) δ 7.69 (s, 2H), 7.60 (dd, J=9.0, 1.3 Hz, 4H), 7.45 (t, J=7.4 Hz, 4H), 7.38 (dt, J=7.3, 1.2 Hz, 2H), 7.24 (s, 2H), 3.90 (s, 6H).

(b) 2,6-Dibromo-3,7-bis-(1,1-dimethoxyethoxy)naphthalene

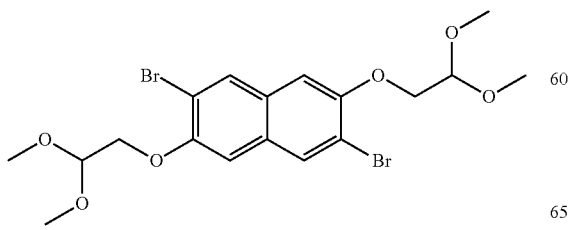

2,6-Dibromo-3,7-bis-(1,1-dimethoxyethoxy)naphthalene was prepared under the same conditions as those used to prepare 2,7-bis-(1,1-dimethoxyethoxy)naphthalene. The reaction gave the desired product as an orange solid (1.96 g, 40% yield). $^1$H NMR (CD$_2$Cl$_2$, 499.8 MHz) δ 7.95 (s, 2H), 7.06 (s, 2H), 4.78 (t, J=5.1 Hz, 2H), 4.10 (d, J=5.1 Hz, 4H), 3.30 (s, 12H).

(c) 3,7-Dibromonaphtho[2,1-b:6,5-b']difuran

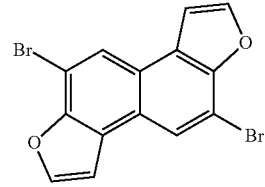 [SMILES: Brc1cc2c3ccoc3c(Br)cc2c2ccoc12]

3,7-Dibromonaphtho[2,1-b:6,5-b']difuran was prepared under the same conditions as those used to prepare 2,7-dibromonaphtha[2,1-b:7,8-b']difuran. The resulting brown solid (1.20 g, 82% yield) was carried to the next step without further purification. $^1$H NMR (CD$_2$Cl$_2$, 499.8 MHz) δ 8.21 (s, 2H), 7.90 (d, J=2.0 Hz, 2H), 7.36 (d, J=2.0 Hz, 2H).

(d) 3,7-Diphenylnaphtho[2,1-b:6,5-b']difuran

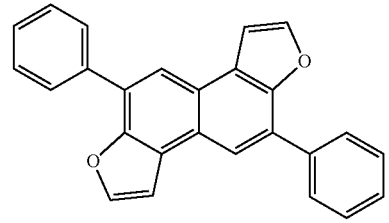 [SMILES: c1ccc(-c2cc3c4ccoc4c(-c4ccccc4)cc3c3ccoc23)cc1]

3,7-Diphenylnaphtho[2,1-b:6,5-b']difuran was prepared under the same conditions as those used to prepare 2,6-dimethoxy-3,7-diphenylnaphthalene. The desired product was obtained as a yellow solid (1.50 g, 83% yield). $^1$H NMR (CD$_2$Cl$_2$, 499.8 MHz) δ 8.20 (s, 2H), 8.03 (dd, J=8.3, 1.2 Hz, 4H), 7.91 (d, J=2.0 Hz, 2H), 7.58 (t, J=7.5 Hz, 4H), 7.49-7.45 (m, 4H).

(e) 2,6-Dibromo-3,7-diphenylnaphtha[2,1-b:6,5-b']difuran

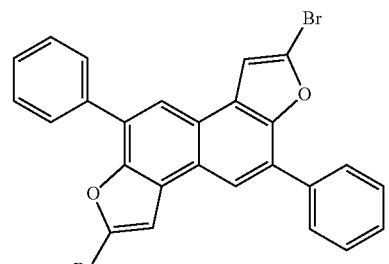

2,6-Dibromo-3,7-diphenylnaphtha[2,1-b:6,5-b']difuran was prepared under the same conditions as those used to prepare 2,7-dibromonaphtha[2,1-b:7,8-b']difuran. The desired product was obtained as an off-white solid (0.20 g, 35% yield). $^1$H-NMR (CD$_2$Cl$_2$, 499.8 MHz) δ 8.06 (s, 2H), 7.96 (dd, J=8.4, 1.2 Hz, 4H), 7.59 (t, J=7.4 Hz, 6H), 7.39 (s, 2H).

(f) N-(4-biphenyl)-N-(3-t-butylphenyl)-N-[4-(4,4,5,5-tetramethyl-1,3,2-dioxaborolan-2-yl)-1-phenyl]amine

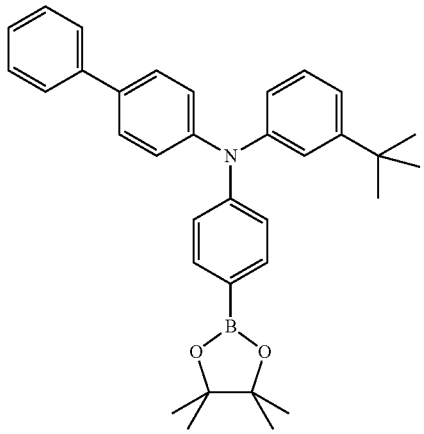 [SMILES: CC(C)(C)c1cccc(N(c2ccc(B3OC(C)(C)C(C)(C)O3)cc2)c2ccc(-c3ccccc3)cc2)c1]

N-(4-biphenyl)-N-(3-t-butylphenyl)-N-[4-(4,4,5,5-tetramethyl-1,3,2-dioxaborolan-2-yl)-1-phenyl]amine was prepared under the same conditions as those used to prepare N,N-diphenyl-N-[6-(4,4,5,5-tetramethyl-1,3,2-dioxaborolan-2-yl)-2-naphthyl]amine. The desired product was obtained as a white foam (1.80 g, 89% yield). $^1$H NMR (CD$_2$Cl$_2$, 499.8 MHz) δ 7.60 (t, J=8.4 Hz, 4H), 7.51 (d, J=8.6 Hz, 2H), 7.42 (t, J=7.4 Hz, 2H), 7.31 (dt, J=7.4, 1.3 Hz, 1H), 7.25-7.21 (m, 2H), 7.16-7.13 (m, 3H), 7.03 (d, J=8.5 Hz, 2H), 6.90 (ddd, J=7.8, 2.4, 1.3 Hz, 1H), 1.32 (s, 12H), 1.26 (s, 9H).

(g) 2,6-Bis-[(N,N-diphenylamino)-9,9-dimethyl-fluoren-2-yl]naphtho[2,1-b:6,5-b']difuran, Compound 2-41

2,6-Bis-[(N,N-diphenylamino)-9,9-dimethyl-fluoren-2-yl]naphtho[2,1-b:6,5-b']difuran was prepared under the same conditions as those used to prepare 2,7-bis-[(N,N-diphenylamino)-6-naphth-2-yl]naphtho[2,1-b:7,8-b']difuran, Compound 2-6 in Synthesis Example 16. The crude product was purified by silica gel column chromatography (1:4 dichloromethane:hexane), passed through a plug of basic alumina (100 g) eluted with hot toluene (900 mL), and finally crystallization (1:2 toluene:acetonitrile) to afford a yellow solid. All impure fractions and crystallization mother liquors were recombined and repurified in the same manner to give the desired product (0.07 g, 22% yield). $^1$H NMR (CD$_2$Cl$_2$, 499.8 MHz) δ 8.20 (s, 2H), 8.13 (dd, J=8.3, 1.1 Hz, 4H), 7.83 (d, J=8.7 Hz, 4H), 7.62-7.59 (m, 10H), 7.54 (d, J=8.6 Hz, 4H), 7.48 (dt, J=7.4, 1.2 Hz, 2H), 7.44 (t, J=7.5 Hz, 4H), 7.32 (dt, J=7.3, 1.3 Hz, 2H), 7.29-7.25 (m, 4H), 7.22-7.16 (m, 10H), 6.97 (ddd, J=7.9, 2.2, 1.0 Hz, 2H), 1.29 (s, 18H).

Synthesis Example 21

This example illustrates the preparation of a compound having Formula I, Compound 2-42.

(a) 1,7-Dihydroxy-6-iodonaphthalene

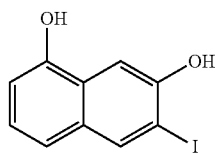

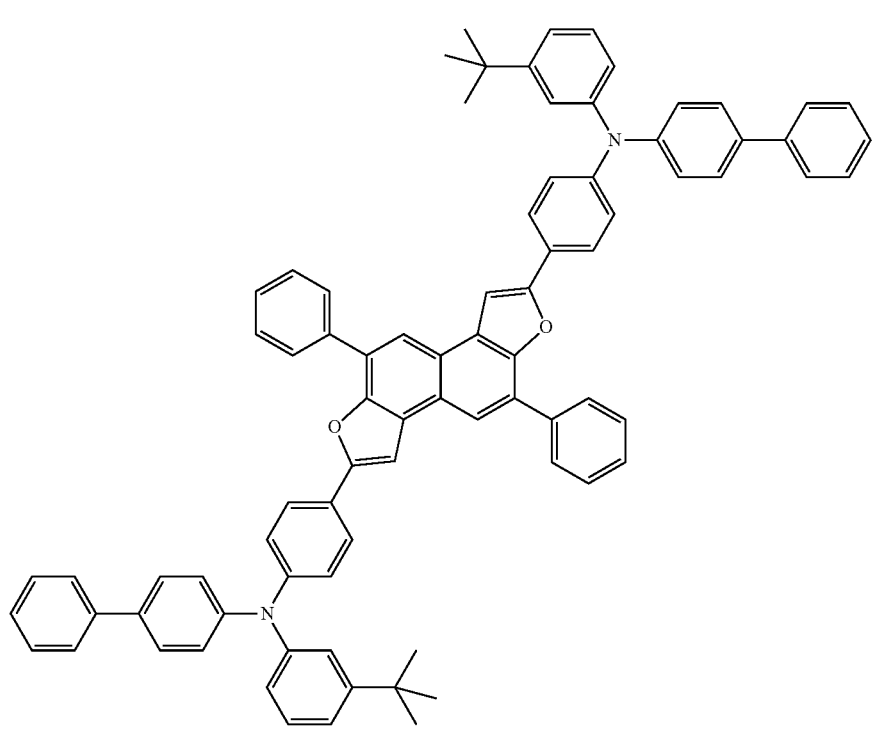 [SMILES: CC(C)(C)c1cccc(N(c2ccc(-c3ccccc3)cc2)c2ccc(-c3cc4c(o3)c(-c3ccccc3)cc3c5cc(-c6ccc(N(c7ccc(-c8ccccc8)cc7)c7cccc(C(C)(C)C)c7)cc6)oc5c(-c5ccccc5)cc43)cc2)c1]

To a 500 mL round-bottom flask charged with 1,7-dimethoxy-6-iodnaphthalene (1.50 g, 4.8 mmol) in dichloromethane (50 mL) at room temperature was added a 1.0 M solution of boron tribromide in dichloromethane (19.1 mL, 19.1 mmol), and the reaction was stirred at room temperature under nitrogen. After 21 h, methanol was added cautiously until all the boron tribromide was quenched. Deionized water was added, and the contents were extracted with dichloromethane. The combined extracts were dried over sodium sulfate, filtered, and the filtrate was concentrated under reduced pressure. The product was purified by passing the crude product through a pad of silica gel using dichloromethane and then dichloromethane/methanol (98/2) as eluent to afford a white solid (1.0 g, 73%). $^1$H NMR (CD$_2$Cl$_2$, 499.8 MHz) δ 8.29 (s, 1H), 7.65 (s, 1H), 7.31 (d, J=8.3 Hz, 1H), 7.20 (t, J=7.7 Hz, 1H), 6.84 (d, J=7.4 Hz, 1H), 5.57 (s, 1H), 5.44 (s, 1H).

(b) 2-(4-chlorophenyl)-8-hydroxynaphthalene

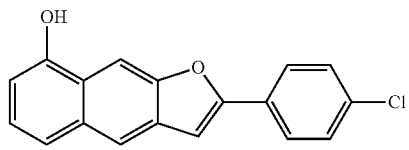 [SMILES: Oc1cccc2cc3cc(-c4ccc(Cl)cc4)oc3cc12]

Inside a glove box, a 250-mL round-bottom flask was charged with 1,7-dihydroxy-6-iodonaphthalene (1.0 g, 3.5 mmol), trans-dichlorobis(triphenylphosphine)-palladium (II) (125 mg, 0.175 mmol), and copper (I) iodide (65 mg, 0.35 mmmol) in N,N-dimethylformamide (17.5 mL) and triethylamine (17.5 mL). 4-chlorophenylacetylene (575 mg, 3.2 mmol) was added portionwise at room temperature to the mixture. The reaction was heated at an external temperature of 100° C. for 2 hours. The reaction was cooled, water and 1M HCl (30 mL) was added and the contents were extracted with chloroform. The combined extracts were dried over sodium sulfate, filtered, and the filtrate was concentrated under reduced pressure. The product was purified by silica gel column chromatography (dichloromethane/hexane) to afford two batches of differing purities of a yellow solid. Trituration with dichloromethane/hexane afforded two batches of a yellow solid (180 mg and 65 mg, 26%) possessing 97.3 and 93.4% purity, respectively. $^1$H NMR (CD$_2$Cl$_2$, 499.8 MHz) δ 8.28 (s, 1H), 8.06 (s, 1H), 7.93 (d, J=8.3 Hz, 2H), 7.57 (d, J=8.8 Hz, 1H), 7.51 (d, 8.2 Hz, 2H), 7.29 (t, J=7.5 Hz, 1H), 7.21 (s, 1H), 6.85 (d, J=7.3 Hz, 1H), 5.50 (s, 1H). UPLC-MS APCI$^+$ (m/z) Calcd for C$_{18}$H$_{11}$ClO$_2$ ([M+H]$^+$) 295.05. Found 295.34.

(c) 2-(4-chlorophenyl)-8-(4-bromophenyl)naphtho[1,2-b'][7,6-b']difuran

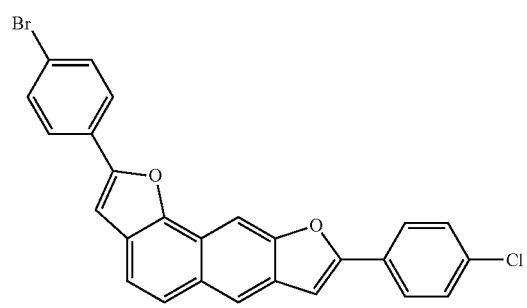 [SMILES: Clc1ccc(-c2cc3cc4ccc5cc(-c6ccc(Br)cc6)oc5c4cc3o2)cc1]

Inside a glove box, a 40 mL glass vial was charged with 2-(4-chlorophenyl)-8-hydroxynaphthalene (180 mg, 0.61 mmol), 2,4'-dibromoacetophenone (187 mg, 0.67 mmol), and basic alumina (435 mg, 4.27 mmol) in toluene (5 mL) and the mixture was heated at an external temperature of 120° C. After 16 hours, the reaction was cooled, filtered through a 0.45 □m PTFE syringe filter, and washed with warm tetrahydrofuran. The filtrate was concentrated under reduced pressure. The crude product was triturated with dichloromethane/hexane, then dissolved in dichloromethane and passed through a plug of Celite® on top of silica gel, eluting with 5:1 dichloromethane/hexane, then dichloromethane to afford a black, sticky solid (140 mg) of 68% purity. UPLC-MS APCI$^+$ (m/z) Calcd for C$_{26}$H$_{14}$BrClO$_2$ ([M]$^+$) 472.99. Found 473.38. Calcd for C$_{26}$H$_{14}$BrClO$_2$ ([M+2H]$^+$) 475.01. Found 475.50.

(d) 2,8-Bis[4-(N-p-biphenyl-N-tert-butylphen-3-yl)phenyl]-naphtho[1,2-b'][7,6-b']difuran, Compound 2-42

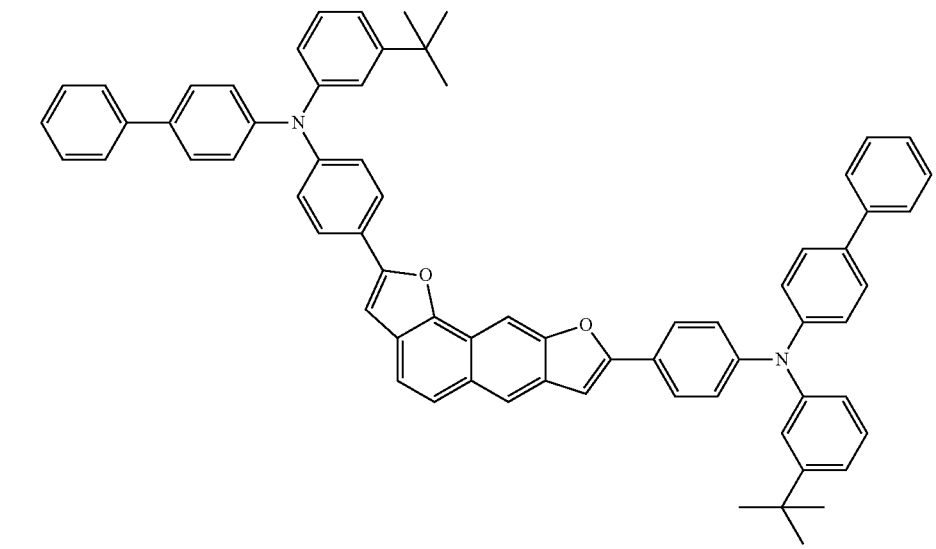 [SMILES: CC(C)(C)c1cccc(N(c2ccc(-c3ccccc3)cc2)c2ccc(-c3cc4cc5ccc6cc(-c7ccc(N(c8ccc(-c9ccccc9)cc8)c8cccc(C(C)(C)C)c8)cc7)oc6c5cc4o3)cc2)c1]

To a 40 mL glass vial charged with 2-(4-chlorophenyl)-8-(4-bromophenyl)naphtho[1,2-b'][7,6-b']difuran (140 mg, 0.20 mmol based on purity), tris(dibenzylideneacetone)dipalladium (0) (16 mg, 0.02 mmol), and tri-tert-butylphosphine (7 mg, 0.03 mmol) in toluene (2 mL) was added, in order, a solution of N-(3-tert-butylphenyl)[1,1'-biphenyl]-4-amine (304 mg, 1.01 mmol) in toluene (1 mL), sodium tert-butoxide (137 mg, 1.43 mmol) and toluene (1 mL). After heating at an external temperature of 120° C. for 3 hours, the reaction was cooled and deionized water, brine, and saturated ammonium chloride were added. The contents were extracted with tetrahydrofuran and the combined extracts were dried over sodium sulfate, filtered, and the filtrate was concentrated under reduced pressure. The product was purified by silica gel column chromatography (dichloromethane/hexane) to afford a white solid. Recrystallization from dichloromethane/hexane afforded a white solid (5 mg, 2.6%). $^1$H NMR (CD$_2$Cl$_2$, 499.8 MHz) δ 8.40 (s, 1H), 8.13 (s, 1H), 7.89 (d, J=8.3 Hz, 2H), 7.86 (d, J=8.3 Hz, 2H), 7.77 (d, J=8.5 Hz, 1H), 7.70-7.54 (m, 8H), 7.46 (t, J=7.4 Hz, 4H), 7.38-7.16 (m, 17H), 7.12 (d, J=4.0 Hz, 2H), 7.01 (d, J=7.8 Hz, 2H), 1.31 (s, 18H). UPLC-MS APCI$^+$ (m/z) Calcd for C$_{56}$H$_{58}$N$_2$O$_2$ ([M+H]$^+$) 959.46. Found 960.41.

Synthesis Example 22

This example illustrates the preparation of a compound having Formula I, Compound 2-10.

(a) 4,4'-dibromo-(naphtho[2,1-b:3,4-b']difuran-2,9-diyl)

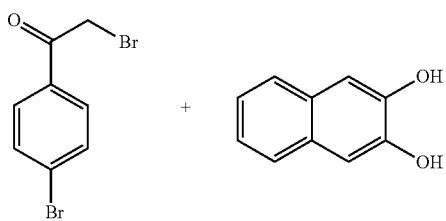

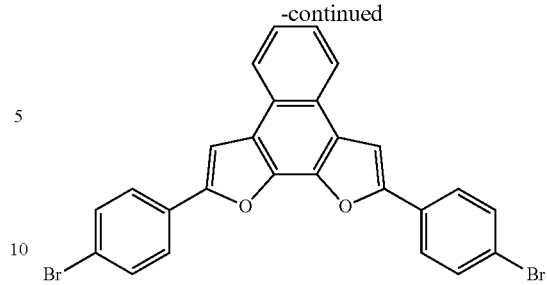

In a nitrogen filled glove box, 4-bromophenacyl-bromide (23.3 mL) and 2,3-naphthalene-diol (4.8 g) were dissolved into 140 mL dry toluene. 50 g basic alumina was added and the slurry stirred at reflux for 16 hrs. The reaction mixture was removed from the glove box and hot filtered at 70 C to remove the alumina which was washed with another 50 mL hot toluene and the resulting solution was reduced in volume to approximately 100 mL. The solution was cooled and allowed to crystallize generating ~1.8 g of the desired product as confirmed by UPLC/MS and 1-H nmr. The solid was collected by filtration, washed with methanol and suction dried.

(b) 4,4'-(naphtho[2,1-b:3,4-b']difuran-2,9-diyl)bis(N,N-diphenylaniline)

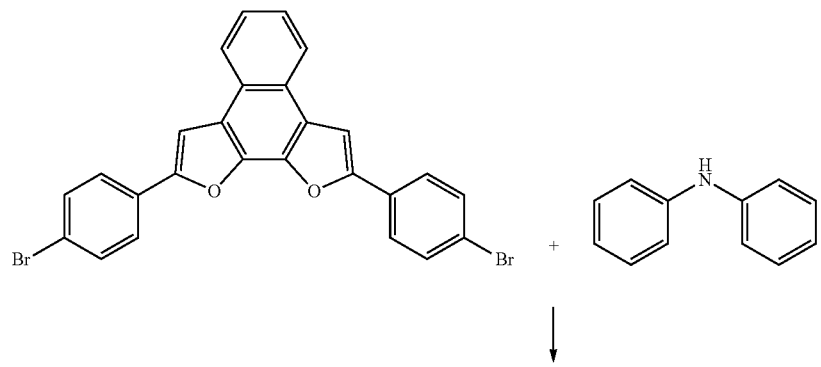

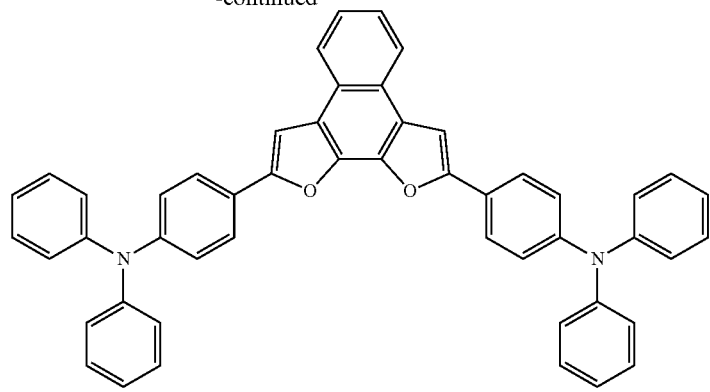

Compound 2-10

Inside a nitrogen filled glove box, a 100 mL round bottom flask was charged with 0.36 g diphenylamine, 0.51 g material from step (a) above, 0.4 g sodium t-butoxide, 0.2 g $Pd_2(DBA)_3$ and 0.1 g tri-t-butyl-phosphine. 40 mL of dry toluene was then added and the mixture warmed and stirred at 100° C. for 3 hrs. The reaction mixture was removed from the glove box and filtered through florisil with toluene washing. The resulting solution was then concentrated to 10 ml and cold acetonitrile, 10 mL, was added. The solution was capped and cooled in a refrigerator overnight. Pale yellow crystals were collected by filtration and washed well with methanol and suction dried. Further recrystallization from hot toluene with added heptane (1:1) yielded 0.35 g pure material as judged by UPLC/MS and 1-H nmr.

Synthesis Example 23

This example illustrates the synthesis of a compound having Formula I, N,N'-(naphtho[2,1-b:3,4-b']difuran-2,9-diyl)bis(4,1-phenylene))bis(N-phenyl-[1,1'-biphenyl]-4-amine), Compound 2-11.

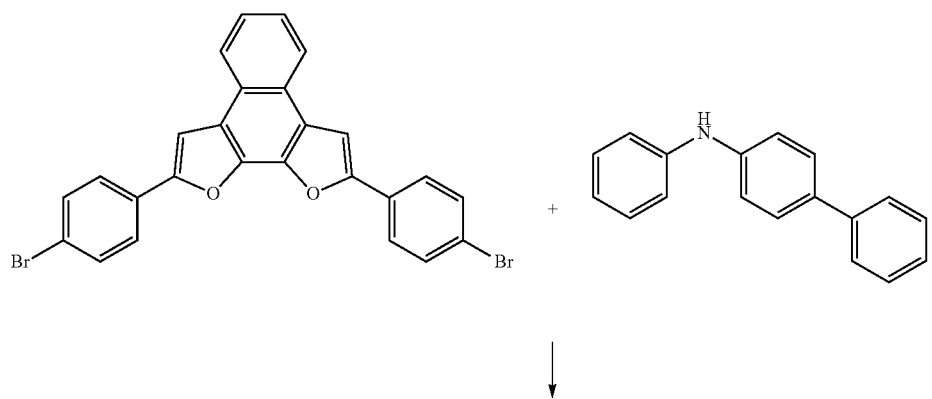

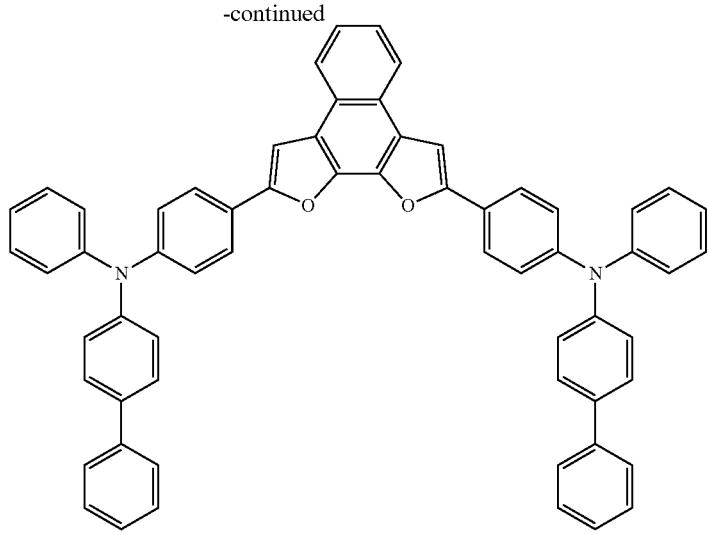

Compound 2-11

Using the same procedure as described above described for Synthesis Example 22 (b), but replacing the diphenylamine with 0.53 g of N-(4-biphenyl)aniline, yielded 0.44 g of the desired material (UPLC/MS and 1-H nmr) after recrystallization from toluene:heptane 1:1.

Synthesis Example 24

This example illustrates the synthesis of a compound having Formula I, N,N'-(naphtho[2,1-b:3,4-b']difuran-2,9-diyl)bis(4,1-phenylene))bis(N-(3-(tert-butyl)phenyl)-[1,1'-biphenyl]-3-amine), Compound 2-43.

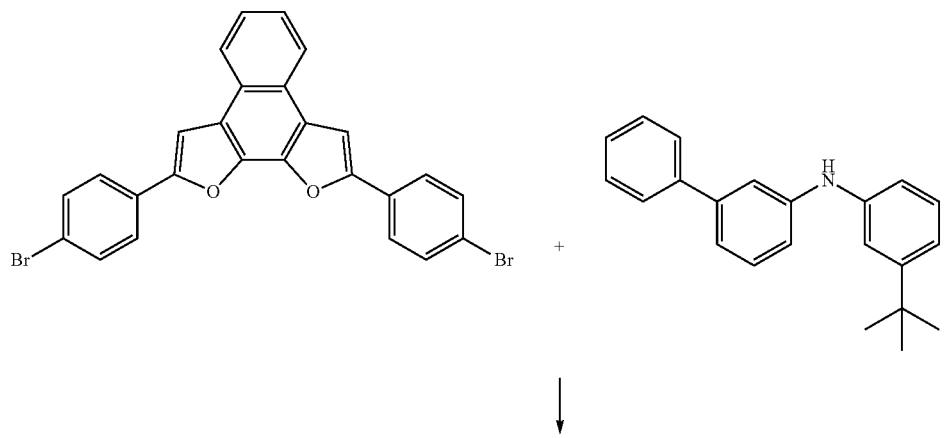

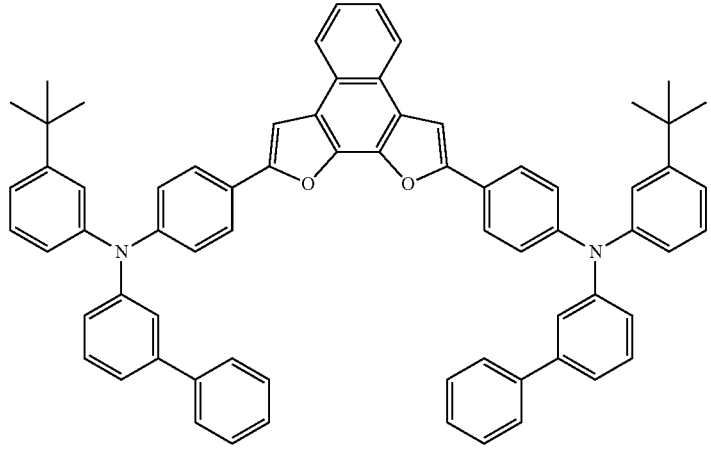

Compound 2-43

Using the same procedure as described above described for Synthesis Example 22 (b), but replacing the diphenylamine with 0.62 g of N-(3-biphenyl),3-t-butyl-aniline, yielded 0.52 g of the desired material (UPLC/MS and 1-H nmr) after silica chromatography eluting with 2:1 toluene:heptane. Final purification was by recrystallization from toluene:heptane 1:1.

Synthesis Example 25

This example illustrates the synthesis of a compound having Formula I, Compound 2-44.

(a) 4,4'-dibromo-(naphtho[1,2-b:4,3-b']difuran-2,5-diyl)

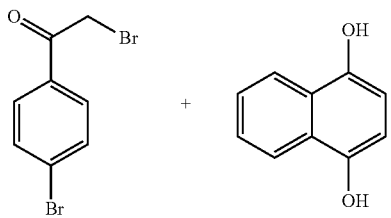

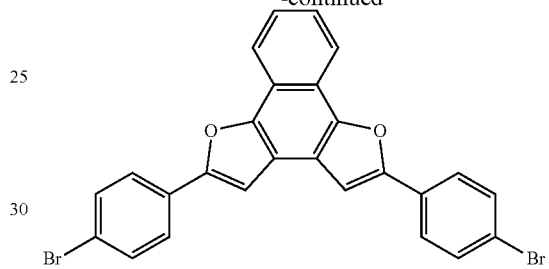

In a nitrogen filled glove box, 4-bromophenacyl-bromide (23.3 mL) and 1,4-naphthalene-diol (4.8 g) were dissolved into 140 mL dry toluene. 50 g basic alumina was added and the slurry stirred at reflux for 16 hrs. The reaction mixture was removed from the glove box and hot filtered at 70 C to remove the alumina which was washed with another 50 mL hot toluene and the resulting solution was reduced in volume to approximately 100 mL. The solution was cooled and allowed to crystallize generating ~1.5 g of the desired product as confirmed by UPLC/MS and 1-H nmr. The solid was collected by filtration, washed with methanol and suction dried. Further purification was effected by extensive washing with THF and toluene followed by vacuum drying.

(b) 4,4'-(naphtho[1,2-b:4,3-b']difuran-2,5-diyl)bis(N-(4-(benzofuran-2-yl)phenyl)-N-(4-isopropylphenyl)aniline)

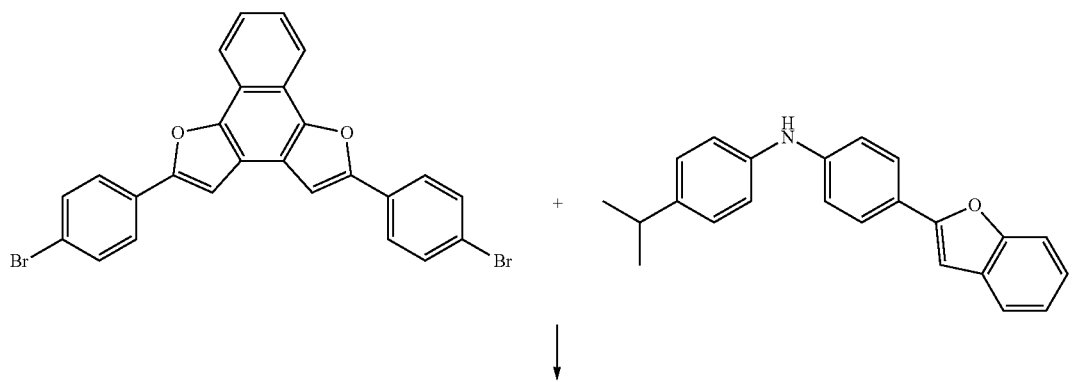

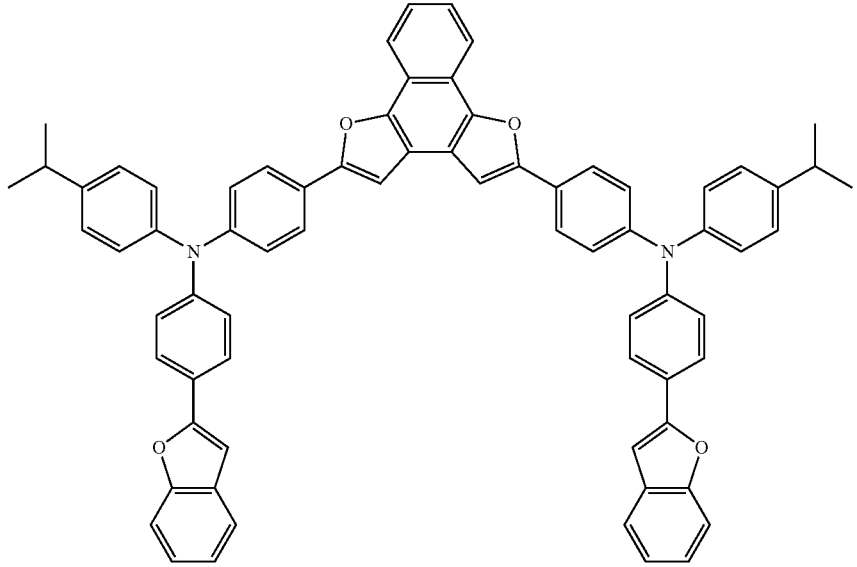

Compound 2-44

The same procedure as described above described for Synthesis Example 22 (b) was used to react 0.51 g 4,4'-dibromo-(naphtho[1,2-b:4,3-b']difuran-2,5-diyl) with 0.68 g of N-(4-(benzofuran-2-yl)phenyl),4-i-propyl-aniline, yielded 0.47 g of the desired material (UPLC/MS and 1-H nmr) after silica chromatography eluting with 1:4 toluene:heptane. Final purification was by recrystallization from toluene:methanol 1:4.

Synthesis Example 26

This example illustrates the synthesis of a compound having Formula I, Compound 2-45.

(a) 4,4'-dibromophenyl-(naphtho[1,2-b:5,6-b']difuran-2,7-diyl)

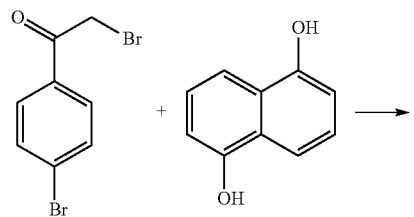

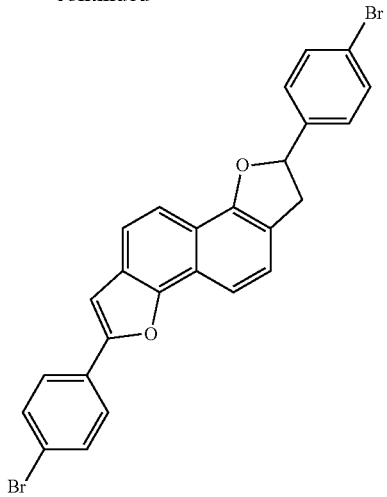

Following the same procedure as described in Synthesis Example 25 (a) but substituting 1,5-naphthalene-diol for 1,4-naphthalene-diol yielded the desired compound 4,4'-dibromophenyl-(naphtho[1,2-b:5,6-b']difuran-2,7-diyl) as identified by UPLC/MS and 1-H nmr spectroscopy.

(b) 4,4'-(naphtho[1,2-b:5,6-b']difuran-2,7-diyl)bis(N-(4-(benzofuran-2-yl)phenyl)-N-(4-isopropylphenyl)aniline)
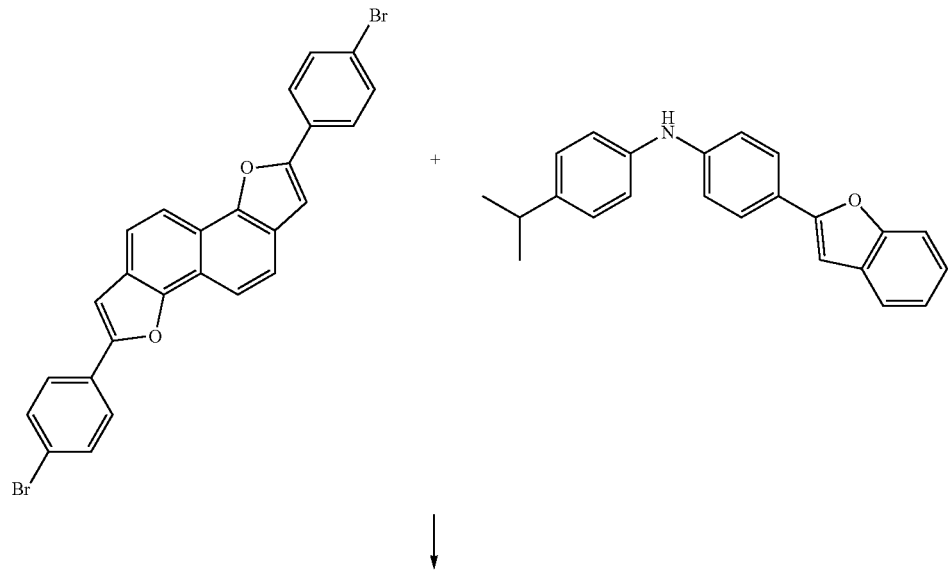
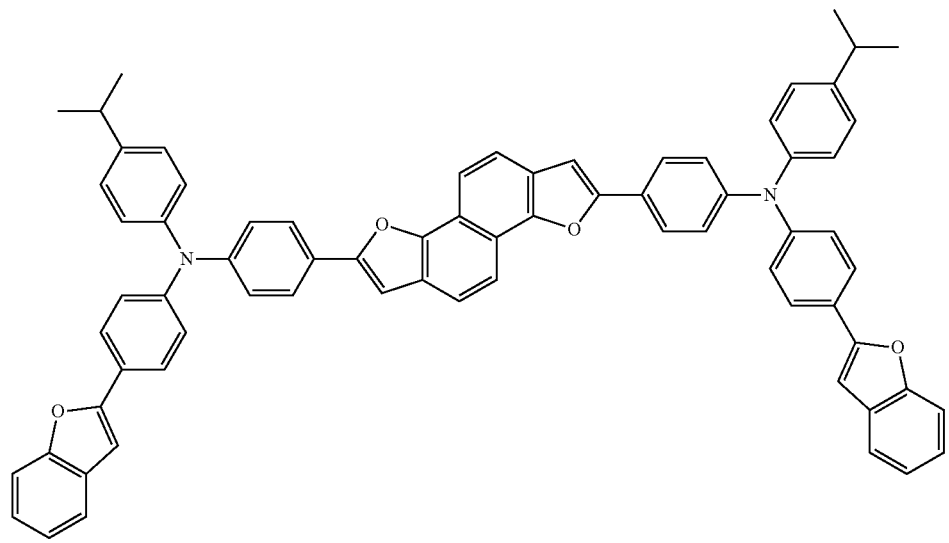
Compound 2-45

The same procedure as described above described for Synthesis Example 22 (b) was used to react 0.51 g 4,4'-dibromophenyl-(naphtho[1,2-b:5,6-b']difuran-2,7-diyl) with 0.68 g of N-(4-(benzofuran-2-yl)phenyl),4-i-propyl-aniline, yielded 0.43 g of the desired material (UPLC/MS and 1-H nmr) after silica chromatography eluting with 1:4 toluene: heptane. Final purification was by recrystallization from toluene:acetonitrile 1:4.

Synthesis Example 27

This example illustrates the synthesis of a compound having Formula I, Compound 2-46.

(a) 4,4'-dichlorophenyl-(naphtho[2,3-b:7,6-b']difuran-2,7-diyl)

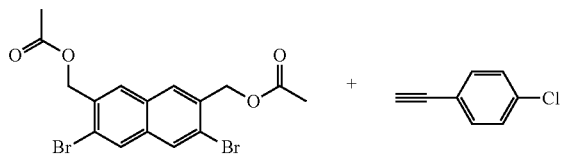

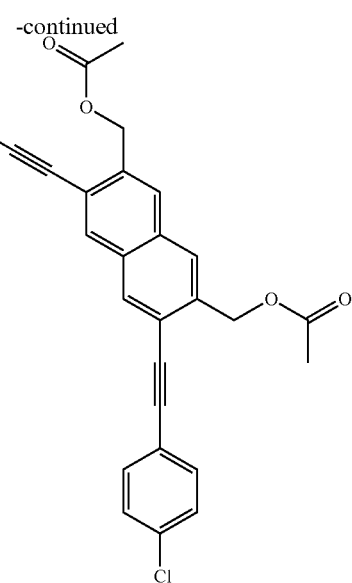

Following the same procedure as described in Synthesis Example 10 (a) and (b) but substituting 3,6-dibromonaphthalene-2,7-diyl diacetate for 3,7-dibromonaphthalene-2,6-diyl diacetate gave the isomeric compound 4,4'-dichlorophenyl-(naphtho[2,3-b:7,6-b']difuran-2,7-diyl) as identified by UPLC/MS and 1-H nmr spectroscopy.

(b) N,N'-(naphtho[2,3-b:7,6-b']difuran-2,7-diylbis(4,1-phenylene))bis(N-(3-(tert-butyl)phenyl)-[1,1'-biphenyl]-3-amine)

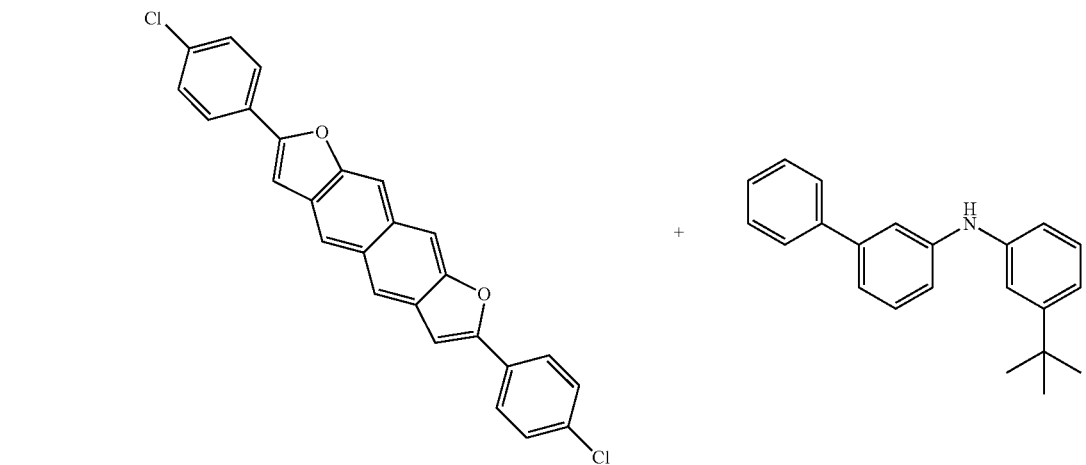

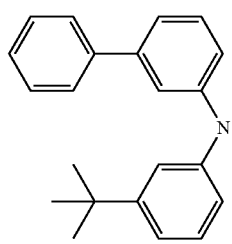
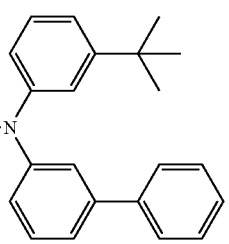

Compound 2-46

The same procedure as described above described for Synthesis Example 22 (b) was used to react 0.115 g 4,4'-dichlorophenyl-(naphtho[2,3-b:7,6-b']difuran-2,7-diyl) with 0.19 g of N-(3-biphenyl),3-t-butyl-aniline, and yielded 0.14 g of the desired material (UPLC/MS and 1-H nmr) after silica chromatography eluting with 5:1 heptane:methylene chloride and a final purification by recrystallization from toluene:acetonitrile 1:4.

Synthesis Example 28

This example illustrates the synthesis of a compound having Formula I, 4,4'-(naphtho[2,3-b:7,6-b']difuran-2,7-diyl)bis(N-(4-(benzofuran-2-yl)phenyl)-N-phenylaniline), Compound 2-47.

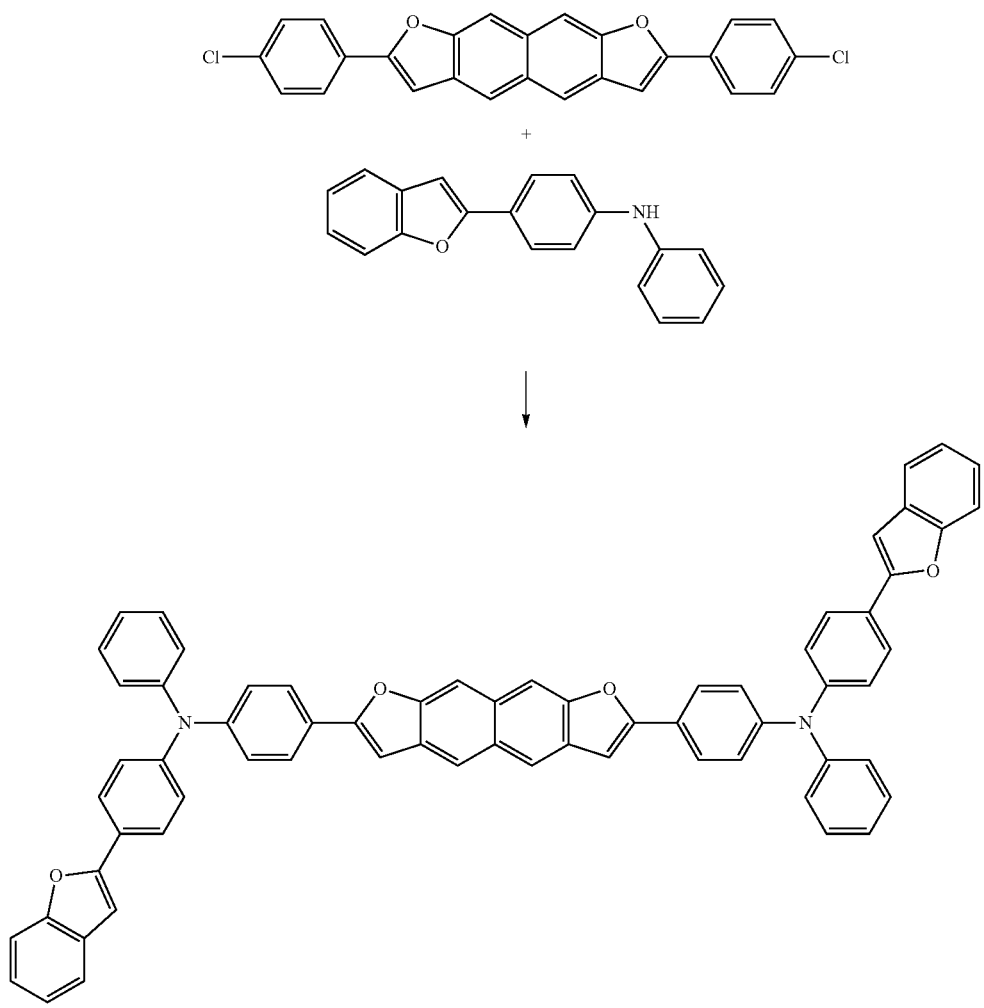

Compound 2-47

The same procedure as described above described for Synthesis Example 22 (b) was used to react 0.207 g 4,4'-dichlorophenyl-(naphtho[2,3-b:7,6-b']difuran-2,7-diyl) with 0.306 g of N-(4-(benzofuran-2-yl)phenyl)aniline, and yielded 0.07 g of the desired material (UPLC/MS and 1-H nmr) after neutral alumina chromatography eluting with methylene chloride and final purification by two recrystallizations from hot xylenes.

Synthesis Example 29

This example illustrates the synthesis of a compound having Formula I, 6,6'-(naphtho[2,3-b:7,6-b']difuran-2,7-diyl)bis(N-(4-(benzofuran-2-yl)phenyl)-N-phenylnaphthalen-2-amine), Compound 2-48.

(a) 2,7-dibromo-1,6-diphenylnaphtho[1,2-b:5,6-b']difuran

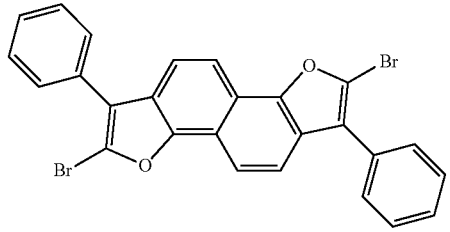

Chemical Formula: $C_{26}H_{14}Br_2O_2$
Molecular Weight: 518.20

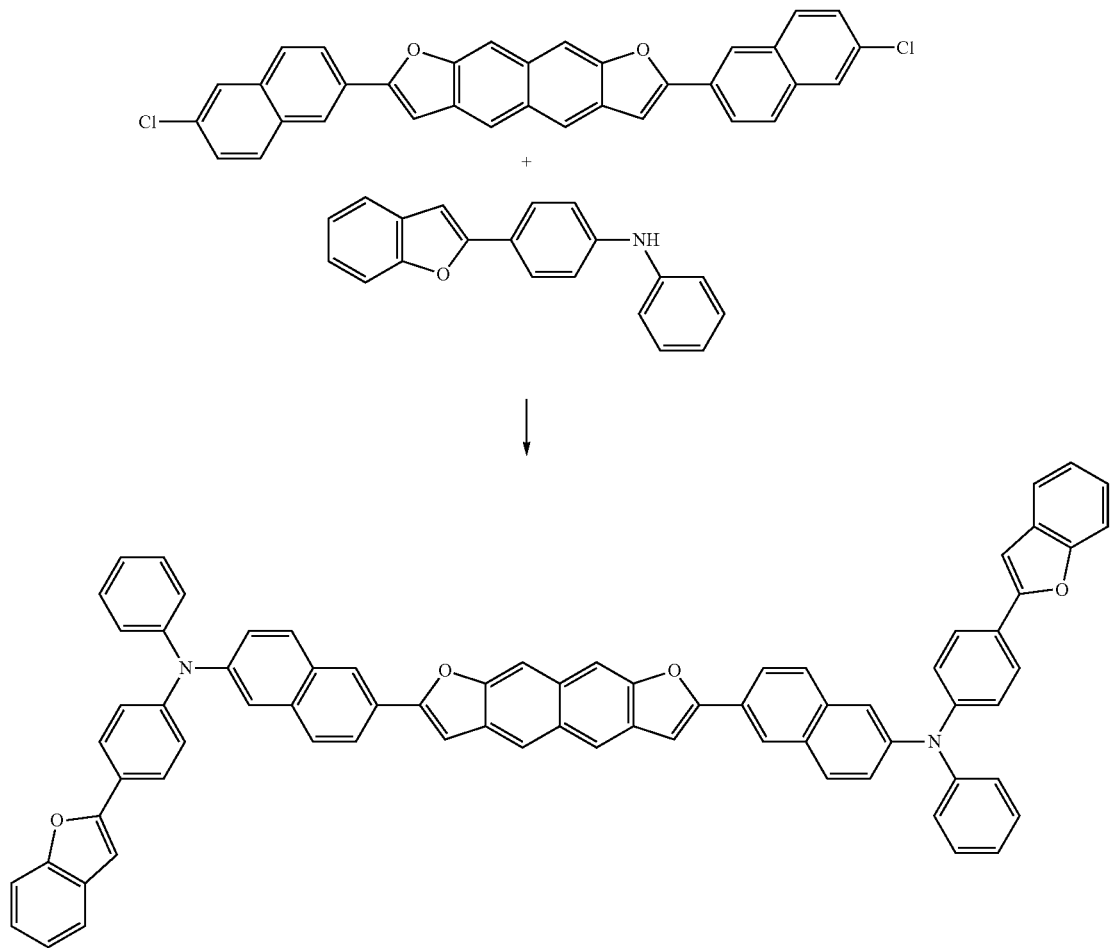

Compound 2-48

The same procedure as described above described for Synthesis Example 22 (b) was used to react 0.142 g 2,2'-dichloro-bisnaphth-6,6'-yl-(naphtho[2,3-b:7,6-b']difuran-2,7-diyl) with 0.170 g of N-(4-(benzofuran-2-yl)phenyl)aniline, and yielded 0.04 g of the desired material (UPLC/MS and 1-H nmr) after basic alumina chromatography eluting with a gradient of toluene in hexanes and final purification by recrystallization from hot methylene chloride.

Synthesis Example 30

This example illustrates the synthesis of a compound having Formula I, Compound 2-20.

Into a RBF (500 mL) was added 1,6-diphenylnaphtho[1,2-b:5,6-b']difuran (4.72 g, 10.00 mmole), chloroform (150 mL), acetic acid (30 mL) and N-bromosuccinimide (3.73 g, 21.00 mmol) in one portion. The reaction was stirred and heated to gentle refluxing stirring for 1 hour. First, a clear solution was formed. Then a light-yellow precipitate came out. UPLC analysis indicated that all starting 1,6-diphenylnaphtho[1,2-b:5,6-b']difuran had been reacted and the product formed.

After cooling down to ambient temperature, water was added. The organic phase was separated, washed with water (50 mL), saturated brine (50 mL) and dried over $MgSO_4$.

The solution was passed through a Silica gel plug and the solvent was evaporated. The residue was crystallized from chloroform/hexane to give the product as light yellow powder (3.36 g, yield 65% in 99.9% purity). NMR spectrum was in consistence with the structure of the product.

(b) 4,4'-(1,6-diphenylnaphtho[1,2-b:5,6-b']difuran-2,7-diyl)bis(N,N-diphenylaniline)

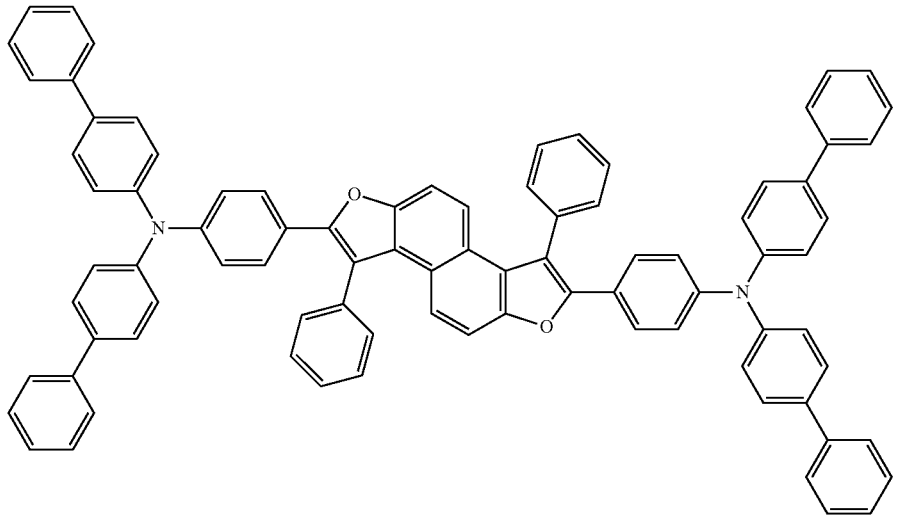 [SMILES: c1ccc(-c2ccc(N(c3ccc(-c4ccccc4)cc3)c3ccc(-c4oc5ccc6c(ccc7oc(-c8ccc(N(c9ccc(-c%10ccccc%10)cc9)c9ccc(-c%10ccccc%10)cc9)cc8)c(-c8ccccc8)c76)c5c4-c4ccccc4)cc3)cc2)cc1]

A 100 mL 3-neck round-bottom flask was charged with 2,7-dibromo-1,6-diphenylnaphtho[1,2-b:5,6-b']difuran (1.88 g, 3.63 mmol), 4-(diphenylamino)phenyl)boronic acid (2.22 g, 7.62 mmol), aqueous sodium carbonate (2M, 7.3 mL), Aliquat™ 336 (32 mg, 0.07 mmol) and toluene (64 mL). The system was purged with nitrogen for 15 minutes. After which, Pd (AMPHOS)$_2$PdCl$_2$ (26 mg, 0.036 mmol) was added and the system was purged for another 5 min. The reaction was heated to reflux with stirring for 16 hours. UPLC analysis indicated that all 2,7-dibromo-1,6-diphenylnaphtho[1,2-b:5,6-b']difuran had been consumed and the product formed as the major component. More toluene (100 mL) was added while the solution was still warm. The organic phase was separated, washed with diluted HCl (10%, 50 ml) and saturated brine (50 mL). The organic layer was filtered through Celite plug to remove the insoluble that formed during the washing. The solution was dried over magnesium sulfate and passed through a short Alumina (basic) column eluted with toluene. The volume of the solution was reduced to about 10 mL and acetonitrile (30 mL) was added. The mixture was allowed to stand at ambient temperature for 16 hour under nitrogen overnight. The solid was filtered, washed with acetonitrile and dried under vacuum at 50° C. for 6 hours. The material was further purified by preparative chromatography (CombiFlush) using hexane/DCM gradient to give a yellow powder (0.76 g, yield 25% in 99.9% purity). UPLC-MS APCI$^+$ (m/z) Calcd for $C_{86}H_{58}N_2O_2$ 1150.45. Found ([M+H]$^+$) 1151.95.

Synthesis Example 31

This example illustrates the synthesis of a compound having Formula I, 2,2'-(naphtho[1,2-b:5,6-b']difuran-2,7-diyl)bis(N,N-diphenylbenzofuran-6-amine, Compound 2-49.

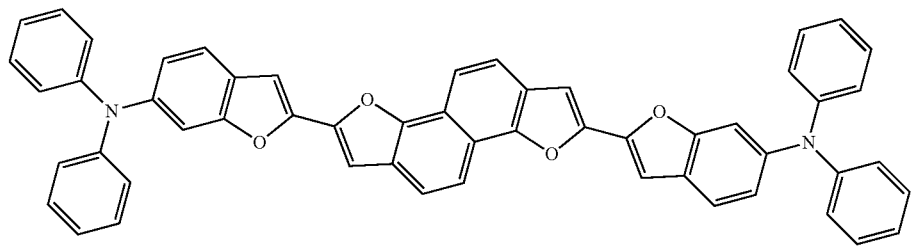 [SMILES: c1ccc(N(c2ccccc2)c2ccc3cc(-c4cc5ccc6c(ccc7cc(-c8cc9ccc(N(c%10ccccc%10)c%10ccccc%10)cc9o8)oc76)c5o4)oc3c2)cc1]

A 100 mL 3-neck round-bottom flask was charged with 2,7-dibromonaphtho[1,2-b:5,6-b']difuran (0.55 g, 1.50 mmol), (6-(diphenylamino) benzofuran-2-yl)boronic acid (1.04 g, 3.15 mmol), aqueous sodium carbonate (2M, 29 mL), Aliquat™ 336 (13 mg, 0.03 mmol) and toluene (116 mL). The system was sparged with nitrogen for 15 minutes. After which, tetrakis(triphenylphosphine)palladium(0) (70 mg, 0.06 mmol) was added and the system was purged for another 5 min. The reaction was stirred with refluxing for 16 hours. UPLC analysis indicated that all, 7-dibromonaphtho[1,2-b:5,6-b']difuran had been consumed and the product formed as the major component. The organic phase was separated, washed with diluted HCl (10%, 50 ml) and saturated brine (50 mL), and dried over magnesium sulfate. The solution was passed through a short Alumina (basic) column eluted with toluene. The solvent was evaporated and the crude product was purified by preparative chromatography (CombiFlush) using hexane/DCM gradient to give a yellow powder (335 mg, yield 29% in 99.4% purity).

Synthesis Example 32

This example illustrates the synthesis of a compound having Formula I, 2,7-bis(4-(10-(m-tolyl)-10H-phenoxazin-3-yl)phenyl)naphtho[2,1-b:6,5-b']difuran, Compound 2-50.

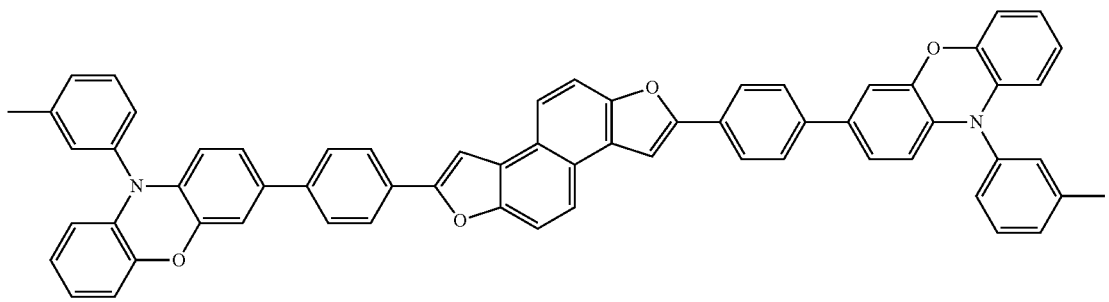

To a 100 mL 3-neck round-bottom flask was charged with 2,7-dibromonaphtho[1,2-b:5,6-b']difuran (0.52 g, 1.00 mmol), 3-(4,4,5,5-tetramethyl-1,3,2-dioxaborolan-2-yl)-10-(m-tolyl)-10H-phenoxazine (0.84 g, 2.10 mmol), aqueous sodium carbonate (2M, 23 mL), Aliquat™ 336 (8 drops) and toluene (90 mL). The system was purged with nitrogen for 15 minutes. After which, tetrakis(triphenylphosphine) palladium(0) (46 mg, 0.04 mmol) was added and the system was purged for another 5 min. The reaction was stirred with refluxing for 16 hours. UPLC analysis indicated that all, 7-dibromonaphtho[1,2-b:5,6-b']difuran had been consumed and the product formed as the major component. After cooling, the mixture was filtered through a Celite/Silica gel/Alumina(basic) plug eluted with toluene. The solvent was evaporated and the crude product was seen precipitated out. It was collected by filtration and washed with toluene/hexane to give 240 mg material. The crude product was dissolved in chloroform (200 mL) under nitrogen with gentle heating until complete dissolution. Celite (2 g) was added and the solvent was removed. The sample was subjected to column separation (CombiFlush) using chloroform/hexane gradient. The product containing fractions were identified by UPLC analysis and combined. The solvent was removed and the product was washed with CDM first then with hexane. The material was dried under vacuum to give three major collections: (1) 31 mg in 99.6% purity; (2) 16 mg in 98.0% in purity; and (3) 23 mg in 98.23% purity by UPLC analysis. MS analysis, M+H 903, in consistence with the structure of the product. UPLC-MS APCI$^+$ (m/z) Calcd for $C_{64}H_{42}N_2O_4$ 902.31. Found ([M+H]$^+$) 903.45.

Synthesis Example 33

This example illustrates the synthesis of a compound having Formula I, Compound 2-51.

(a) 2-chloro-N-phenyl-N-(m-tolyl)benzofuran-6-amine

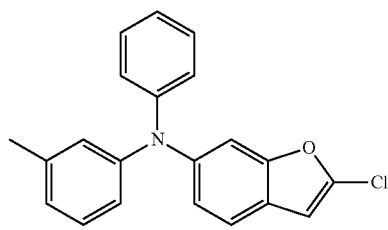 [SMILES: Cc1cccc(N(c2ccccc2)c2ccc3cc(Cl)oc3c2)c1]

Inside dry box, 6-bromo-2-chlorobenzofuran (0.79 g, 3.00 mmol), 3-methylaniline (1.00 g, 5.45 mmol), sodium t-butoxide (1.04 g, 10.82 mmol), tri-t-butylphosphine (87 mg, 0.43 mmol), and tris(dibenzylideneacetone) dipalladium(0) (158 mg, 0.17 mmol) were mixed with dry toluene (50 mL). The reaction mixture was stirred at room temperature for 3 hours, filtered through a Celite® plug, and concentrated under reduced pressure. The crude product obtained was purified by silica gel column chromatography (CombiFlush) eluted with dichloromethane/hexane gradient. The product was obtained as a clear liquid (1.33 g, 92%) in 99% purity by UPLC analysis. UPLC-MS APCI$^+$ (m/z) Calcd for $C_{21}H_{16}ClNO$ 333.09. Found ([M+H]$^+$) 334.23. $^1$H-NMR spectrum was in consistence with the structure of the product.

(b) N-phenyl-2-(4,4,5,5-tetramethyl-1,3,2-dioxaborolan-2-yl)-N-(m-tolyl)benzofuran-6-amine

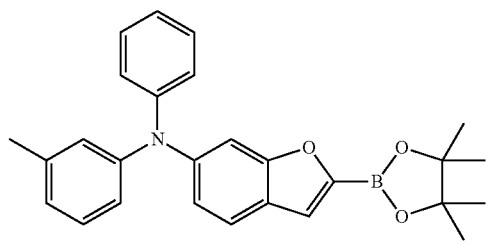

In dry box, to a 250 mL 3-neck round-bottom flask was charged with 2-chloro-N-phenyl-N-(m-tolyl) benzofuran-6-amine (1.33 g, 3.98 mmol), 4,4,4',4',5,5,5',5'-octamethyl-2,2'-bi(1,3,2-dioxaborolane) (1.21 g, 4.78 mmol), potassium acetate (1.05 g, 11.94), Pd$_2$(dba)$_3$ (73 mg, 0.08 mmol), X-Phos™ (76 mg, 0.16 mmol) and 1,4-Dioxane (50 mL). The reaction was stirred at 80° C. for 5 hours. After cooling, the mixture was filtered through a Celite plug eluted with DCM. The solvent was evaporated and the crude product was subjected to column separation (CombiFlush) using chloroform/hexane gradient. The product containing fractions were identified by UPLC analysis and combined to give a white powder (0.95 g, 57%). UPLC-MS APCI$^+$ (m/z) Calcd for $C_{27}H_{28}BNO_3$ 425.22. Found ([M+H]$^+$) 426.13. $^1$H-NMR spectrum was in consistence with the structure of the product.

(c) 2,2'-(naphtho[1,2-b:5,6-b']difuran-2,7-diyl)bis(N-phenyl-N-(m-tolyl)benzofuran-6-amine)

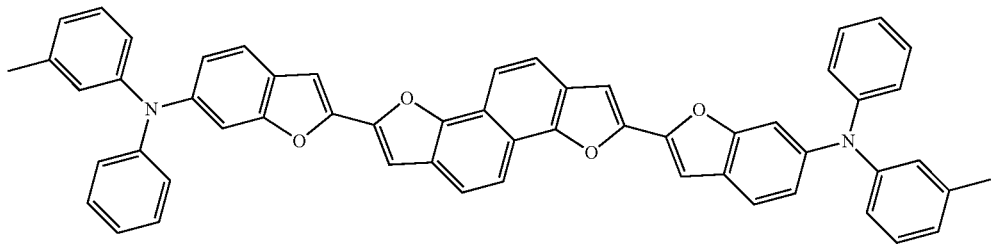

To a 100 mL 3-neck round-bottom flask was charged with 2,7-dibromonaphtho[1,2-b:5,6-b']difuran (0.34 g, 93 mmol), N-phenyl-2-(4,4,5,5-tetramethyl-1,3,2-dioxaborolan-2-yl)-N-(m-tolyl)benzofuran-6-amine (0.95 g, 22.24 mmol), Cs$_2$CO$_3$ (2.42 g, 7.44 mmol), 23 mL), and toluene (40 mL). The system was purged with nitrogen for 15 minutes. After which, tetrakis(triphenylphosphine) palladium(0) (107 mg, 0.09 mmol) was added and the system was purged for another 5 min. The reaction was heated to refluxing and stirred under nitrogen for 16 hours. After cooling, the solid was filtered off, washed with small volume of toluene, water and ethanol. The crude product was dried under vacuum overnight and purified by column chromatography (Combi-Flush) eluted with DCM/hexane gradient. The product containing fractions were identified by UPLC analysis and combined to give three major collections: (1) 15 mg in 99.9% purity; (2) 130 mg, in 98.91% purity; and (3) 95 mg in 97.9% purity. UPLC-MS APCI$^+$ (m/z) Calcd for $C_{56}H_{38}N_2O_4$ 802.28. Found ([M+H]$^+$) 804.26. $^1$H-NMR spectrum was in consistence with the structure of the product.

Photoluminescence Examples

PL Examples 1-15

These examples illustrate the photoluminescence of compounds having Formula I.

The compounds were individually dissolved in toluene. The concentration was adjusted such that the optical density of the solution in a 1-cm quartz cell was preferably in the 0.2-0.4 range, at the excitation wavelengths between 300 and 360 nm. The photoluminescence spectrum was measured with a Spex Fluorolog spectrometer. The results are given in Table 1 below.

TABLE 1

| Example | Compound | Concentration μM | PL peak, nm | PL FWHM, nm |
|---|---|---|---|---|
| PL1 | 2-2 | 10 | 432 | 46 |
| PL2 | 2-5 | 3.75 | 427 | 44 |
| PL3 | 2-6 | 3 | 427 | 43 |
| PL4 | 2-8 | 3 | 437 | 49 |
| PL5 | 2-9 | 30 | 435 | 40 |
| PL6 | 2-14 | 3 | 438 | 42 |
| PL7 | 2-17 | 3 | 439 | 42 |
| PL8 | 2-20 | * | 434 | 43 |
| PL9 | 2-27 | 3.75 | 442 | 49 |
| PL10 | 2-35 | 2.5 | 437 | 43 |
| PL11 | 2-36 | 3.75 | 455 | 46 |
| PL12 | 2-43 | 2 | 440 | 48 |
| PL13 | 2-45 | 2.5 | 435 | 36 |
| PL14 | 2-47 | 1.67 | 437 | 38 |
| PL15 | 2-48 | 1.5 | 443 | 45 |

PL is photoluminescence;
* indicates concentration not determined due to limited solubility.

Device Examples (1) Materials
ET-1 is an aryl phosphine oxide.
ET-2 is lithium quinolate.
ET-3 is a benzimidazole-substituted anthracene.
HIJ-1 is a hole injection material which is made from an aqueous dispersion of an electrically conductive polymer and a polymeric fluorinated sulfonic acid.
HIJ-2 is 1,4,5,8,9,12-hexaazatriphenylenehexacarbonitrile ("HAT-CN").
Host-1 is a deuterated diaryl anthracene. Such materials have been described in published PCT Application WO 2011028216.
HTM-1 is a mono-arylamino phenanthrene.
NPD is N,N'-di(1-naphthyl)-N,N'-diphenyl-(1,1'-biphenyl)-4,4'-diamine.

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Device Type 1: Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent, to form a short reduction layer ("SRL"). The workpieces were then placed in a vacuum chamber. The hole injection material, one or more hole transport materials, the photoactive and host materials, electron transport materials, electron injection material, and the Al cathode were then deposited sequentially by thermal evaporation using the appropriate masks, to form the hole injection layer ("HIL"), one or more hole transport layers ("HTL"), the photoactive layer or emissive layer ("EML"), the electron transport layer ("ETL"), and the electron injection layer ("EIL"), followed by the cathode. The chamber was vented, and the devices were encapsulated using a glass lid, desiccant, and UV curable epoxy.

Device Type 2: Device Type 2 was made the same as Device Type 1, but without an SRL.

All ratios are weight ratios, unless otherwise indicated.

(3) Device Characterization

The OLED devices were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Examples 1-3

This example illustrates the use of a compound having Formula I, Compound 2-2, as the emissive material in the photoactive layer of a device. The device was made as described in Device Type 1.

The devices had the following layers.
Anode=ITO (50 nm)
SRL=HIJ-1 (100 nm)
HIL=HIJ-2 (7 nm)
HTL1=NPD (95 nm)
HTL2=HTM-1 (20 nm)
EML=Host-1:Compound 2-2 in the weight ratios shown below (25 nm)
ETL=ET-3:ET-2 (2:3) (30 nm)
Cathode=Al (100 nm)

The results are given in Table 2 below.

TABLE 2

Device results

| Ex. | Ratio | CE (cd/A) | EQE (%) | CIEX | CIEY | V at 15 mA/cm² | T90 (h) |
|---|---|---|---|---|---|---|---|
| 1 | 20:1 | 6.1 | 5.4 | 0.147 | 0.137 | 4.9 | 300 |
| 2 | 32:1 | 6.0 | 5.6 | 0.148 | 0.124 | 4.9 | 275 |
| 3 | 13:1 | 5.9 | 5.0 | 0.149 | 0.147 | 4.9 | 355 |

All data at 1000 nits, unless otherwise specified. Ratio is the weight ratio of Host-1 to dopant Compound 2-2; CE is the current efficiency; EQE=external quantum efficiency; CIEX and CIEY refer to the x and y color coordinates according to the C.I.E. chromaticity scale (Commission Internationale de L'Eclairage, 1931); V is voltage; T90 is the time in hours to reach 90% of the initial luminance at 50° C. and a current density of 16.5 mA/cm².

Device Examples 4-24

These examples illustrate the use of a compound having Formula I, as the emissive material in the photoactive layer of a device. The device was made as described in Device Type 2.

The devices had the following layers.
Anode=ITO (50 nm)
HIL=HIJ-2 (10 nm)
HTL1=NPD (168 nm)
HTL2=HTM-1 (20 nm)
EML=Host-1 and a compound having Formula I (25 nm); the compound and weight ratio are given in Table 3 below.
ETL=ET-1:ET-2 (1:1) (26.5 nm)
EIL=ET-2 (3.5 nm)
Cathode=Al (100 nm)

The results are given in Table 3 below.

TABLE 3

Device results

| Ex. | Comp. | Ratio | cd/A | EQE (%) | CIEX | CIEY | V | T90 (h) |
|---|---|---|---|---|---|---|---|---|
| 4 | 2-4 | 20:1 | 4.7 | 6.5 | 0.151 | 0.075 | 6.6 | 500 |
| 5 | 2-5 | 20:1 | 4.8 | 5.4 | 0.151 | 0.092 | 5.6 | 500 |
| 6 | 2-20 | 20:1 | 5.9 | 7.5 | 0.149 | 0.081 | 5.8 | 1380 |
| 7 | 2-6 | 32:1 | 4.3 | 6.1 | 0.151 | 0.071 | 5.5 | 90 |
| 8 | 2-8 | 20:1 | 7.6 | 7.6 | 0.148 | 0.112 | 5.8 | 900 |
| 9 | 2-9 | 20:1 | 6.3 | 6.9 | 0.153 | 0.098 | 5.7 | 100 |
| 10 | 2-41 | 30:1 | 13.3 | 9.0 | 0.143 | 0.208 | 6.0 | 2100 |
| 11 | 2-41 | 20:1 | 13.2 | 8.6 | 0.144 | 0.222 | 5.9 | 3000 |
| 12 | 2-36 | 30:1 | 13.0 | 8.7 | 0.145 | 0.213 | 5.7 | 2800 |
| 13 | 2-37 | 30:1 | 11.8 | 8.4 | 0.147 | 0.189 | 5.5 | 1250 |
| 14 | 2-37 | 20:1 | 10.7 | 7.6 | 0.147 | 0.193 | 5.5 | 1800 |
| 15 | 2-40 | 30:1 | 10.9 | 8.7 | 0.147 | 0.156 | 5.6 | 1300 |
| 16 | 2-40 | 40:1 | 11.0 | 8.9 | 0.147 | 0.151 | 5.5 | 1200 |
| 17 | 2-49 | 30:1 | 9.9 | 8.6 | 0.144 | 0.140 | 5.9 | 200 |
| 18 | 2-49 | 40:1 | 10.0 | 8.9 | 0.145 | 0.135 | 5.9 | 400 |
| 19 | 2-47 | 30:1 | 7.0 | 8.6 | 0.146 | 0.091 | 5.3 | 600 |
| 20 | 2-47 | 40:1 | 7.0 | 8.6 | 0.146 | 0.090 | 5.3 | 520 |
| 21 | 2-50 | 32:1 | 12.0 | 9.3 | 0.144 | 0.166 | 5.3 | 20 |
| 22 | 2-43 | 30:1 | 11.6 | 9.0 | 0.148 | 0.163 | 5.1 | 1300 |
| 23 | 2-43 | 40:1 | 11.5 | 9.1 | 0.148 | 0.158 | 5.2 | 1360 |
| 24 | 2-51 | 32:1 | 13.4 | 10.7 | 0.144 | 0.158 | 5.2 | 160 |

All data at 1000 nits, unless otherwise specified. Comp. is the Compound having Formula I; Ratio is the weight ratio of Host-1 to the dopant Com pound having Formula I; CE is the current efficiency; EQE=external quantum efficiency; CIEX and CIEY refer to the x and y color coordinates according to the C.I.E. chromaticity scale (Commission Internationale de L'Eclairage, 1931); V is voltage at 15 mA/cm²; T90 is the time in hours to reach 90% of the initial luminance at 50° C. and a current density of 16.5 mA/cm².

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. An electronic device comprising an anode, a cathode, and a photoactive layer therebetween, wherein the photoactive layer comprises a host material and a dopant having blue emission color, wherein the dopant is a compound selected from the following:

[Compound 2-36]

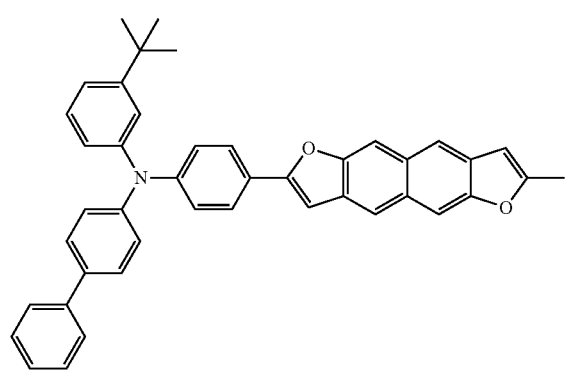

[Compound 2-37]

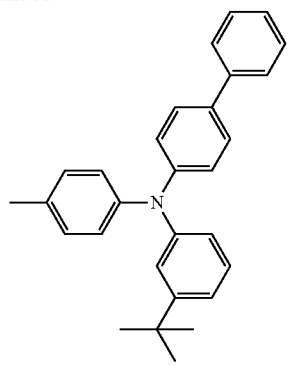

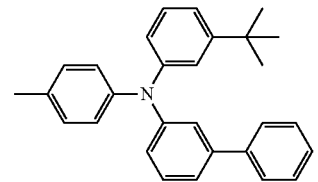

* * * * *

UNITED STATES PATENT AND TRADEMARK OFFICE
CERTIFICATE OF CORRECTION

| | | |
|---|---|---|
| PATENT NO. | : 12,384,796 B2 | Page 1 of 1 |
| APPLICATION NO. | : 16/301483 | |
| DATED | : August 12, 2025 | |
| INVENTOR(S) | : Weiying Gao et al. | |

It is certified that error appears in the above-identified patent and that said Letters Patent is hereby corrected as shown below:

On the Title Page

Item (72), Inventors:
Change "Michael Henry Howard" to "Michael Henry Howard, Jr."

Signed and Sealed this
Seventh Day of October, 2025

John A. Squires
*Director of the United States Patent and Trademark Office*